United States Patent
Talley

Patent Number: 5,859,257
Date of Patent: Jan. 12, 1999

[54] ISOXAZOLE COMPOUNDS AS CYCLOOXYGENASE INHIBITORS

[75] Inventor: John J Talley, Brentwood, Mo.

[73] Assignee: G. D. Searle & Co., Skokie, Ill.

[21] Appl. No.: 702,417

[22] Filed: Aug. 14, 1996

Related U.S. Application Data

[63] Continuation-in-part of PCT/US96/01869, Feb. 12, 1996 which is a continuation-in-part of Ser. No. 473,884, Jun. 7, 1995, Pat. No. 5,633,272, which is a continuation-in-part of Ser. No. 387,680, Feb. 13, 1995, abandoned.

[51] Int. Cl.$^6$ .................................................. C07D 261/06
[52] U.S. Cl. ........................ 548/247; 546/272.1; 548/243; 548/245; 548/248
[58] Field of Search ..................... 546/272.1; 548/243, 548/245, 247, 248

[56] References Cited

U.S. PATENT DOCUMENTS

| | | | |
|---|---|---|---|
| 5,310,926 | 5/1994 | Hagiwara et al. ............... | 548/247 |
| 5,318,970 | 6/1994 | Suzuki et al. ................... | 514/252 |
| 5,633,272 | 5/1997 | Talley et al. ................... | 514/378 |

FOREIGN PATENT DOCUMENTS

| | | |
|---|---|---|
| 93/35480 | 10/1993 | Australia . |
| 026928 | 4/1981 | European Pat. Off. . |
| 549797 | 7/1993 | European Pat. Off. . |
| 623603 | 11/1994 | European Pat. Off. . |
| 633254 | 1/1995 | European Pat. Off. . |
| 4314966 | 11/1994 | Germany . |
| 2223568 | 9/1990 | Japan . |
| 4173780 | 6/1992 | Japan . |
| 92/19604 | 11/1992 | WIPO . |
| 94/17059 | 8/1994 | WIPO . |
| 94/20475 | 9/1994 | WIPO . |
| 95/00501 | 1/1995 | WIPO . |
| 95/12587 | 5/1995 | WIPO . |
| 95/14672 | 6/1995 | WIPO . |

OTHER PUBLICATIONS

Ichiro Yamawaki et al, Chem. Pharm. Bull., 36:3142–3146 (1988).
Umezawa et al, Cbem., vol. 36, No. 9, pp. 1150–1154, Sep. 1963.
Descamps et al, Bull. Soc. Chim. Belg., 73:459–482 (1964).

*Primary Examiner*—Johann Richter
*Assistant Examiner*—Laura L. Stockton
*Attorney, Agent, or Firm*—Joseph W. Bulock

[57] ABSTRACT

A class of substituted isoxazolyl compounds is described for use in treating cyclooxygenase-2 related disorders. Compounds of particular interest are defined by Formula I

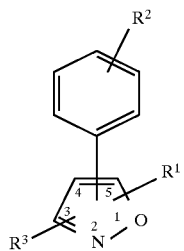

wherein $R^1$, $R^2$, and $R^3$, are described in the specification.

8 Claims, No Drawings

ISOXAZOLE COMPOUNDS AS CYCLOOXYGENASE INHIBITORS

This application is a continuation-in-part of International Application PCT/US96/01869, with an international filing date of Feb. 12, 1996, which is a continuation-in-part of Ser. No. 08/473,884, filed Jun. 7, 1995 now U.S. Pat. No. 5,633,272, which is a continuation-in-part of Ser. No. 08/387,680, filed Feb. 13, 1995, now abandoned.

FIELD OF THE INVENTION

This invention is in the field of antiinflammatory pharmaceutical agents and specifically relates to compounds, compositions and methods for treating inflammation and other cyclooxygenase-2 associated disorders, such as arthritis. In addition, the invention relates to a method of preparing isoxazolyl benzenesulfonamides.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, which limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel isoxazoles disclosed herein are such safe and also effective antiinflammatory agents furthering such efforts. The substituted isoxazolyl compounds disclosed herein preferably selectively inhibit cyclooxygenase-2 over cyclooxygenase-1.

Isoxazoles have been described for various uses, including the treatment of inflammation. DE 4,314,966, published Nov. 10, 1994, describes 3-(2-hydroxyphenyl)isoxazoles for the treatment of inflammatory disorders. WO 92/05162, published Apr. 4, 1992, describes 5-piperazinyl-3,4-diaryl-isoxazoles as having medicinal use.

WO 92/19604, published Nov. 12, 1992, describes 5-alkene-3,4-diaryl-isoxazoles as having cyclooxygenase inhibition activity. EP 26928, published Apr. 15, 1981, describes 3,4-diaryl-isoxazole-5-acetic acids as having anti-inflammatory activity. WO 95/00501, published Jan. 5, 1995, generically describes 3,4-diaryl-isoxazoles as cyclooxygenase-2 inhibitors.

The invention's isoxazolyl compounds are found to show usefulness in vivo as antiinflammatory agents with minimal side effects.

DESCRIPTION OF THE INVENTION

A class of substituted isoxazolyl compounds useful in treating inflammation and other cyclooxygenase-2 related disorders is defined by Formula I:

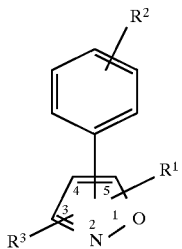

wherein $R^1$ is selected from R-, RO-, RS-, RO-alkyl, RS-alkyl, carboxyl, cyano, hydroxyl, amino, halo, carboxyalkyl, alkoxycarbonylalkyl, aminocarbonyl, aminocarbonylalkyl, alkoxyalkyloxyalkyl, aryl (hydroxylalkyl), haloalkylsulfonyloxy, arylcarbonyloxyalkyl, arylcarbonylthioalkyl, alkoxycarbonyloxyalkyl, alkylaminocarbonyloxyalkyl, alkylaminocarbonylthioalkyl,

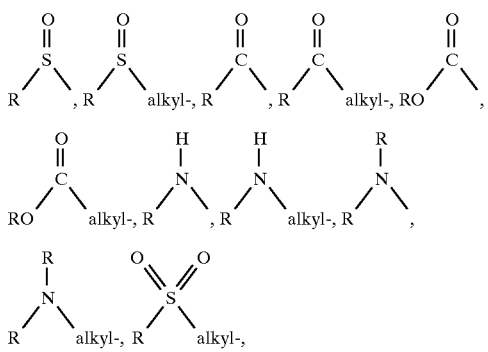

and $R^aO_2CR^b$—X-alkyl-;

wherein R is independently selected from alkyl, haloalkyl, hydroxyalkyl, aryl, cycloalkyl, heterocyclo, aralkyl, cycloalkylalkyl, and heterocycloalkyl;

wherein $R^a$ is selected from hydrido and R;

wherein $R^b$ is selected from a direct bond, alkyl, haloalkyl, hydroxyalkyl, aryl, cycloalkyl, heterocyclo, alkylaryl, aralkyl, cycloalkylalkyl, and heterocycloalkyl;

wherein X is selected from O, S and S(O);

wherein $R^2$ is selected from methylsulfonyl, hydroxysulfonyl, and aminosulfonyl; and wherein $R^3$ is selected from cycloalkyl, cycloalkenyl, aryl and heterocyclo; wherein $R^3$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio;

provided $R^2$ is aminosulfonyl when the $R^2$-substituted phenyl radical is at isoxazole position 3; or a pharmaceutically-acceptable salt thereof.

Compounds of Formula I would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, premature labor, tendinitis, bursitis, skin-related conditions such as psoriasis, eczema, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as retinitis, retinopathies, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional antiinflammatories, such as together with steroids, NSAIDs, 5-lipoxygenase inhibitors, $LTB_4$ receptor antagonists and $LTA_4$ hydrolase inhibitors.

Suitable $LTA_4$ hydrolase inhibitors include RP-64966, (S,S)-3-amino-4-(4-benzyloxyphenyl)-2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(1E,3E-tetradecadienyl)-2-oxiranyl)benzoic acid lithium salt (Searle).

Suitable $LTB_4$ receptor antagonists include, among others, ebselen, linazolast, ontazolast, Bayer Bay-x-1005, Ciba Geigy compound CGS-25019C, Leo Denmark compound ETH-615, Merck compound MAFP, Terumo compound TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

The present invention preferably includes compounds which selectively inhibit cyclooxygenase-2 over cyclooxygenase-1. Preferably, the compounds have a cyclooxygenase-2 $IC_{50}$ of less than about 0.5 μM, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 μM, and more preferably of greater than 20 μM. Such preferred selectivity may indicate an ability to reduce the incidence of common NSAID-induced side effects.

A preferred class of compounds consists of those compounds of Formula I wherein $R^1$ is selected from R-, RO-, RS-, lower RO-alkyl, lower RS-alkyl, carboxyl, cyano, hydroxyl, amino, halo, lower carboxyalkyl, lower alkoxycarbonylalkyl, aminocarbonyl, lower aminocarbonylalkyl, lower alkoxyalkyloxyalkyl, lower aryl (hydroxylalkyl), lower haloalkylsulfonyloxy, lower arylcarbonyloxyalkyl, lower arylcarbonylthioalkyl, lower alkoxycarbonyloxyalkyl, lower alkylaminocarbonyloxyalkyl, lower alkylaminocarbonylthioalkyl,

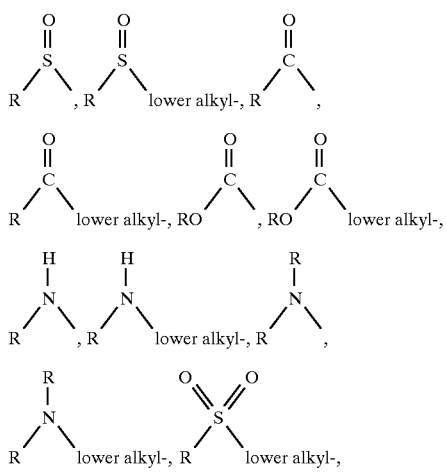

and $R^aO_2CR^b$—X-lower alkyl-;

wherein R is independently selected from lower alkyl, lower haloalkyl, lower hydroxyalkyl, optionally substituted phenyl, lower cycloalkyl, heteroaryl, lower aralkyl, lower cycloalkylalkyl, and lower heteroarylalkyl; wherein R is independently selected from lower alkyl, lower haloalkyl, lower hydroxyalkyl, aryl, lower cycloalkyl, heteroaryl, lower aralkyl, lower cycloalkylalkyl, and lower heteroarylalkyl; wherein $R^a$ is selected from hydrido and R; wherein $R^b$ is selected from direct bond, lower alkyl, lower haloalkyl, lower hydroxyalkyl, phenyl, lower cycloalkyl, heteroaryl, lower alkylphenyl, lower aralkyl, lower cycloalkylalkyl, and lower heteroarylalkyl; wherein x is selected from O, S and S(O); wherein $R^2$ is selected from methylsulfonyl, hydroxysulfonyl, and aminosulfonyl; and wherein $R^3$ is selected from lower cycloalkyl, lower cycloalkenyl, aryl, and heteroaryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, lower alkylsulfonyl, aminosulfonyl, and lower alkylthio; or a pharmaceutically-acceptable salt thereof.

A more preferred class of compounds consists of those compounds of Formula I wherein $R^1$ is selected from hydroxyl, lower alkyl, carboxyl, halo, cyano, lower alkylthio, phenylthio, lower alkylsulfinyl, phenylsulfinyl, lower (hydroxy)alkoxyalkyl, lower haloalkylcarbonylalkyl, lower aryloxyalkyl, lower arylthioalkyl, lower alkoxycarbonylalkylthioalkyl, lower carboxyalkylaryloxyalkyl, lower aralkyl, lower alkoxycarbonylalkylaryloxyalkyl, lower haloalkyl, lower heteroarylthioalkyl, lower carboxyalkyl, lower alkoxycarbonylalkyl, lower alkoxyalkyl, lower alkoxyalkyloxyalkyl, lower aralkoxyalkyl, lower haloalkylsulfonyloxy, lower hydroxylalkyl, lower aryl (hydroxylalkyl), lower carboxyalkoxyalkyl, lower carboxyaryloxyalkyl, lower alkoxycarbonylaryloxyalkyl, lower cycloalkyl and lower cycloalkylalkyl; wherein $R^2$ is selected from methylsulfonyl, hydroxysulfonyl, and aminosulfonyl; and wherein $R^3$ is selected from phenyl and 5–6 membered heteroaryl; wherein $R^3$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, phenylamino, lower aminoalkyl, nitro, halo, lower alkoxy, aminosulfonyl, and lower alkylthio; or a pharmaceutically-acceptable salt thereof.

A class of compounds of particular interest consists of those compounds of Formula I wherein $R^1$ is selected from hydroxyl, methyl, ethyl, propyl, isopropyl, butyl, tert-butyl, isobutyl, pentyl, isopentyl, neopentyl, hexyl, chloro, carboxyl, cyano, carboxypropyl, carboxyisopropyl, carboxymethyl, carboxyethyl, carboxybutyl, carboxypentyl, methoxycarbonylmethyl, methoxycarbonylethyl, methoxycarbonylpropyl, trifluoromethylcarbonylmethyl, methoxy, ethoxy, butoxy, phenoxy, methoxymethyl, phenoxymethyl, 4-fluorophenoxymethyl, pyridinylthiomethyl, phenylthio, methylthio, ethylthio, butylthio, methylsulfinyl, ethylsulfinyl, butylsulfinyl, methoxyethyloxymethyl, benzyloxymethyl, phenylethoxymethyl, fluoromethyl, difluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, 2-hydroxy-2-methylpropoxymethyl, hydroxyethoxymethyl, 2-hydroxy-2-methylpentyl, trifluoromethylsulfonyloxy, 2-(4-chlorophenyl)-2-hydroxylethyl, methoxycarbonylmethylthiomethyl, carboxymethylthiomethyl, carboxymethoxymethyl, (4-carboxyphenyl)oxymethyl, (4-carboxymethylphenyl) oxymethyl, (4-methoxycarbonylphenyl)oxymethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected from benzyl and phenylethyl, wherein the phenyl ring is optionally substituted at a substitutable position with fluoro, chloro, bromo, iodo, methyl, and methoxy; wherein $R^2$ is selected from methylsulfonyl, hydroxysulfonyl, and aminosulfonyl; and wherein $R^3$ is selected from phenyl, pyridyl, thienyl, thiazolyl, oxazolyl and furyl; wherein $R^3$ is optionally substituted at a substitutable position with one or more radicals independently selected from trifluoromethoxy, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, fluoromethyl, difluoroethyl, difluoropropyl, dichloroethyl, dichloropropyl, hydroxyl, hydroxymethyl, fluoro, chloro, bromo, iodo, methoxy, ethoxy, propoxy, n-butoxy, pentoxy, hexyloxy, methylenedioxy, methylthio, ethylthio, and butylthio; or a pharmaceutically-acceptable salt thereof.

Within Formula I there is a subclass of compounds of high interest represented by Formula II:

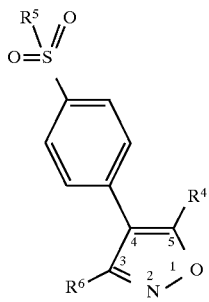

wherein $R^4$ is selected from hydroxyl, lower alkyl, carboxyl, halo, cyano, lower carboxyalkyl, lower alkoxycarbonylalkyl, lower aralkyl, lower alkylthio, phenylthio, lower alkylsulfinyl, lower alkoxyalkyl, lower haloalkylcarbonylalkyl, phenylsulfinyl, lower (hydroxy)alkoxyalkyl, lower aryloxyalkyl, lower arylthioalkyl, lower alkoxycarbonylalkylthioalkyl, lower haloalkyl, lower carboxyalkylaryloxyalkyl, lower alkoxycarbonylalkylaryloxyalkyl, lower hydroxylalkyl, lower heteroarylthioalkyl, lower alkoxyalkyloxyalkyl, lower aralkoxyalkyl, lower haloalkylsulfonyloxy, lower aryl(hydroxylalkyl), lower carboxyalkoxyalkyl, lower carboxyaryloxyalkyl, lower alkoxycarbonylaryloxyalkyl, lower cycloalkyl and lower cycloalkylalkyl; wherein $R^5$ is selected from methyl, hydroxy, and amino; and wherein $R^6$ is selected from aryl and 5–6 membered heteroaryl; wherein $R^6$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, amino, lower haloalkoxy, lower alkylamino, phenylamino, lower aminoalkyl, nitro, halo, lower alkoxy, aminosulfonyl, and lower alkylthio; or a pharmaceutically-acceptable salt thereof.

A class of compounds of particular interest consists of those compounds of Formula II wherein $R^4$ is selected from hydroxyl, methyl, ethyl, propyl, isopropyl, butyl, tert-butyl, isobutyl, pentyl, isopentyl, neopentyl, hexyl, chloro, carboxyl, carboxypropyl, carboxymethyl, carboxyethyl, carboxybutyl, carboxypentyl, methoxycarbonylmethyl, methoxycarbonylethyl, methoxycarbonylpropyl, methoxy, ethoxy, butoxy, phenoxy, methoxymethyl, phenoxymethyl, 4-fluorophenoxymethyl, pyridinylthiomethyl, methylthio, ethylthio, butylthio, phenylthio, methylsulfinyl, ethylsulfinyl, butylsulfinyl, phenylsulfinyl, methoxyethyloxymethyl, benzyloxymethyl, phenylethoxymethyl, fluoromethyl, difluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, 2-hydroxy-2-methylpropoxymethyl, hydroxyethoxymethyl, 2-hydroxy-2-methylpentyl, trifluoromethylsulfonyloxy, 2-(4-chlorophenyl)-2-hydroxylethyl, methoxycarbonylmethylthiomethyl, carboxymethyltl, omethyl, carboxymethoxymethyl, (4-carboxyphenyl) oxymethyl, (4-carboxymethylphenyl)oxymethyl, (4-methoxycarbonylphenyl)oxymethyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected from benzyl and phenylethyl, wherein the phenyl ring is optionally substituted at a substitutable position with fluoro, chloro, bromo, iodo, methyl, and methoxy; and wherein $R^6$ is selected from phenyl and 3-pyridyl; wherein $R^6$ is optionally substituted at a substitutable position with one or more radicals independently selected from trifluoromethoxy, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, fluoromethyl, difluoroethyl, difluoropropyl, dichloroethyl, dichloropropyl, hydroxyl, hydroxymethyl, fluoro, chloro, bromo, iodo, methoxy, ethoxy, propoxy, n-butoxy, pentoxy, hexyloxy, methylenedioxy, methylthio, ethylthio, butylthio, and hexylthio; or a pharmaceutically-acceptable salt thereof.

Within Formula I there is a subclass of compounds of high interest represented by Formula III:

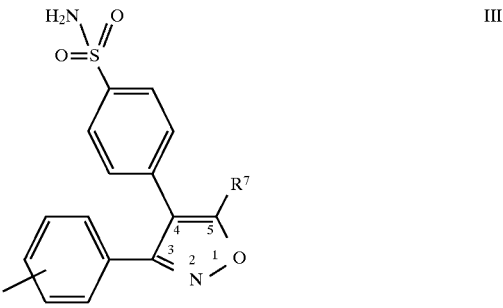

wherein $R^7$ is selected from hydroxyl, lower alkyl, carboxyl, halo, lower carboxyalkyl, lower alkoxycarbonylalkyl, lower alkoxyalkyl, lower carboxyalkoxyalkyl, lower haloalkyl, lower alkylthio, lower alkylsulfinyl, lower (hydroxy)alkoxyalkyl, lower carboxyalkylaryloxyalkyl, lower haloalkylsulfonyloxy, lower hydroxylalkyl, lower aryl(hydroxylalkyl), lower carboxyaryloxyalkyl, lower cycloalkyl, lower cycloalkylalkyl, and lower aralkyl; and wherein $R^8$ is one or more radicals independently selected from hydrido, lower alkylsulfinyl, lower alkyl, cyano, carboxyl, lower alkoxycarbonyl, lower haloalkyl, hydroxyl, lower hydroxyalkyl, lower haloalkoxy, amino, lower alkylamino, lower arylamino, lower aminoalkyl, nitro, halo, lower alkoxy, aminosulfonyl, and lower alkylthio; or a pharmaceutically-acceptable salt thereof.

Within Formula I there is a subclass of compounds of high interest represented by Formula IV:

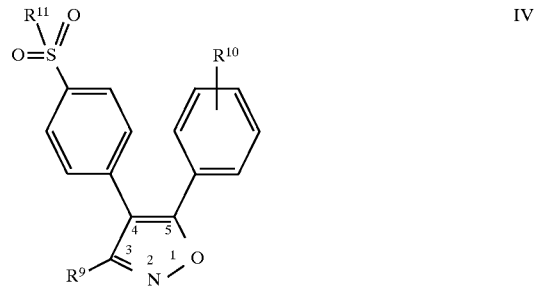

wherein $R^9$ is selected from lower alkyl, lower carboxyalkyl, lower alkoxycarbonylalkyl, lower alkoxyalkyloxyalkyl, lower hydroxylalkyl, and lower aralkyl; wherein $R^{10}$ is one or more radicals independently selected from hydrido, lower alkyl, lower haloalkyl, halo and lower alkoxy; and wherein $R^{11}$ is methyl or amino; or a pharmaceutically-acceptable salt thereof.

A class of compounds of particular interest consists of those compounds of Formula IV wherein $R^9$ is selected from methyl, ethyl, propyl, isopropyl, butyl, tert-butyl, isobutyl, pentyl, isopentyl, neopentyl, hexyl, carboxypropyl, carboxymethyl, carboxyethyl, carboxybutyl, carboxypentyl, methoxycarbonylmethyl, methoxycarbonylethyl, methoxyethyloxymethyl, hydroxylmethyl, hydroxylpropyl, hydroxylethyl, and lower aralkyl selected from benzyl and phenylethyl, wherein the phenyl ring is optionally substituted at a substitutable position with fluoro, chloro, bromo, iodo, methyl, and methoxy; wherein $R^{10}$ is one or more radicals independently selected from hydrido, methyl, ethyl, isopropyl, butyl, tert-butyl, isobutyl, pentyl, hexyl, fluoromethyl, difluoromethyl, trifluoromethyl, chloromethyl, dichloromethyl, fluoromethyl, difluoroethyl, difluoropropyl, dichloroethyl, dichloropropyl, fluoro, chloro, bromo, iodo, methoxy, ethoxy, propoxy, n-butoxy, pentoxy, and methylenedioxy: and wherein $R^{11}$ is methyl or amino; or a pharmaceutically-acceptable salt thereof.

Within Formula I there is a subclass of compounds of high interest represented by Formula V:

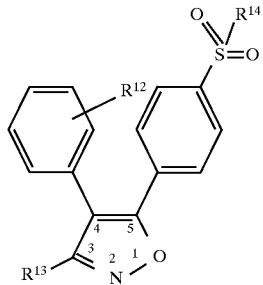

wherein $R^{12}$ is one or more radicals independently selected from hydrido, halo, lower haloalkyl, lower alkoxy and lower alkyl; wherein $R^{13}$ is selected from lower alkyl, lower carboxyalkyl, lower alkoxycarbonylalkyl and lower aralkyl; and wherein $R^{14}$ is methyl or amino; or a pharmaceutically-acceptable salt thereof.

A class of compounds of particular interest consists of those compounds of Formula V wherein $R^{12}$ is one or more radicals independently selected from hydrido, methyl, ethyl, isopropyl, butyl, tert-butyl, isobutyl, pentyl, fluoromethyl, difluoromethyl, trifluoromethyl, chloromethyl, dichloromethyl, fluoroethyl, difluoroethyl, difluoropropyl, dichloroethyl, dichloropropyl, fluoro, chloro, bromo, iodo, methoxy, ethoxy, propoxy, n-butoxy, pentoxy, and methylenedioxy; and wherein $R^{13}$ is selected from methyl, ethyl, propyl, isopropyl, butyl, tert-butyl, isobutyl, pentyl, isopentyl, neopentyl, hexyl, carboxypropyl, carboxymethyl, carboxyethyl, carboxybutyl, carboxypentyl, methoxycarbonylmethyl, methoxycarbonylethyl, and lower aralkyl selected from benzyl and phenylethyl, wherein the phenyl ring is optionally substituted at a substitutable position with fluoro, chloro, bromo, iodo, methyl, and methoxy; or a pharmaceutically-acceptable salt thereof.

A family of specific compounds of particular interest within Formula I consists of compounds and pharmaceutically-acceptable salts thereof as follows:
3-[5-methyl-3-phenylisoxazol-4-yl]benzenesulfonamide;
3-methyl-4-(4-methylsulfonylphenyl)-5-phenylisoxazole;
4-[3-ethyl-5-(2-methylphenyl)isoxazol-4-yl] benzenesulfonamide;
4-[5-(2-hydroxyethyl)-3-phenylisoxazol-4-yl] benzenesulfonamide;
4-[5-(2-methyl-2-hydroxy-1-n-propyloxymethyl-3-phenylisoxazol-4-yl]benzenesulfonamide;
4-[5-(4-hydroxy-4-methylpentyl)-3-phenylisoxazol-4-yl] benzenesulfonamide;
4-[5-methylthio-3-phenylisoxazol-4-yl] benzenesulfonamide;
4-[5-methylsulfinyl-3-phenylisoxazol-4-yl] benzenesulfonamide;
4-[5-(2-hydroxyethyl)oxymethyl-3-phenylisoxazol-4-yl] benzenesulfonamide;
5-hydroxymethyl-4-(4-methylsulfonyl)phenyl-3-phenylisoxazole;
methyl[4-(4-aminosulfonylphenyl)-3-(3,4-dichlorophenyl) isoxazol-5-yl]butanoate;
[4-(4-aminosulfonylphenyl)-3-(3,4-dichlorophenyl) isoxazol-5-yl]butanoic acid;
methyl[4-(4-aminosulfonylphenyl)-3-(3,4-dichlorophenyl) isoxazol-5-yl]propanoate;
[4-(4-aminosulfonylphenyl)-3-(3,4-dichlorophenyl) isoxazol-5-yl]propanoic acid;
[4-(4-aminosulfonylphenyl)-3-(3,4-dichlorophenyl) isoxazol-5-yl]acetic acid;
4-[5-methyl-3-(3,4-dichlorophenyl)isoxazol-4-yl] benzenesulfonamide;
4-[5-[2-hydroxy-3-(3'-pyridyl)propyl]-3-phenylisoxazol-4-yl]benzenesulfonamide;
4-[5-ethoxy-3-phenylisoxazol-4-yl]benzenesulfonamide;
4-[3-phenyl-5-propoxy-isoxazol-4-yl]benzenesulfonamide;
4-[5-(2-methylethoxy)-3-phenylisoxazol-4-yl] benzenesulfonamide;
4-[5-butoxy-3-phenylisoxazol-4-yl]benzenesulfonamide;
4-[5-(2-methyl-propoxy)-3-phenylisoxazol-4-yl] benzenesulfonamide;
4-[5-(1-methyl-propoxy)-3-phenylisoxazol-4-yl] benzenesulfonamide;
4-[5-phenoxy-3-phenylisoxazol-4-yl]benzenesulfonamide;
4-[5-(4-chlorophenoxy)-3-phenylisoxazol-4-yl] benzenesulfonamide;
4-[5-(2,4-dichlorophenoxy)-3-phenylisoxazol-4-yl] benzenesulfonamide;
4-[5-(ethylsulfinyl)-3-phenylisoxazol-4-yl] benzenesulfonamide;
4-[3-phenyl-5-(propylsulfinyl)-isoxazol-4-yl] benzenesulfonamide;
4-[5-(isopropylsulfinyl)-3-phenylisoxazol-4-yl] benzenesulfonamide;
4-[5-(butylsulfinyl)-3-phenylisoxazol-4-yl] benzenesulfonamide;
4-[5-[(2-methylpropyl)sulfinyl]-3-phenylisoxazol-4-yl] benzenesulfonamide;
4-[5-[(1-methylpropyl)sulfinyl]-3-phenylisoxazol-4-yl] benzenesulfonamide;
4-[5-(phenylsulfinyl)-3-phenylisoxazol-4-yl] benzenesulfonamide;
4-[5-(4-chlorophenylsulfinyl)-3-phenylisoxazol-4-yl] benzenesulfonamide;
4-[5-(2,4-dichlorophenylsulfinyl)-3-phenylisoxazol-4-yl] benzenesulfonamide;
4-[5-(ethylthio)-3-phenylisoxazol-4-yl] benzenesulfonamide;
4-[3-phenyl-5-(propylthio)-isoxazol-4-yl] benzenesulfonamide;
4-[5-(isopropylthio)-3-phenylisoxazol-4-yl] benzenesulfonamide;
4-[5-(butylthio)-3-phenylisoxazol-4-yl] benzenesulfonamide;
4-[5-[(2-methylpropyl)thio]-3-phenylisoxazol-4-yl] benzenesulfonamide;
4-[5-[(1-methylpropyl)thio]-3-phenylisoxazol-4-yl] benzenesulfonamide;
4-[5-(phenylthio)-3-phenylisoxazol-4-yl] benzenesulfonamide;
4-[5-[(4-chlorophenyl)thio]-3-phenylisoxazol-4-yl] benzenesulfonamide;
4-[5-[(2,4-dichlorophenyl)thio]-3-phenylisoxazol-4-yl] benzenesulfonamide;
[4-(4-aminosulfonylphenyl)-3-(3,4-difluorophenyl) isoxazol-5-yl]acetic acid;
4-[5-[phenylthiomethyl]-3-phenylisoxazol-4-yl] benzenesulfonamide;
4-[5-[(4-fluorophenoxy)methyl]-3-phenylisoxazol-4-yl] benzenesulfonamide;
6-[4-[4-(aminosulfonyl)phenyl]-5-methylisoxazol-3-yl]-2,3-dichlorobenzoic acid;
4-[4-[4-(aminosulfonyl)phenyl]-3-phenylisoxazol-5-yl] methoxy]benzeneacetic acid;

[[4-[4-(aminosulfonyl)phenyl]-3-phenylisoxazol-5-yl]-methylthio]acetic acid;
methyl [[4-[4-(aminosulfonyl)phenyl]-3-phenylisoxazol-5-yl]-methylthio]acetate;
4-[5-[(4-fluorophenoxy)methyl]-3-phenylisoxazol-4-yl]benzenesulfonamide;
4-[3-phenyl-5-[(2-pyridinylthio)methyl]-isoxazol-4-yl]benzenesulfonamide;
[4-[4-(aminosulfonyl)phenyl]-3-phenylisoxazol-5-yl]-3-methylbutan-1-oic acid;
[[4-[4-(aminosulfonyl)phenyl]-3-phenylisoxazol-5-yl]-methyloxy]acetic acid;
4-[4-[4-(aminosulfonyl)phenyl]]-3-phenylisoxazol-5-yl]butanoic acid;
4-[5-cyano-3-phenylisoxazol-4-yl]benzenesulfonamide;
4-[5-chloro-3-phenylisoxazol-4-yl]benzenesulfonamide;
4-[3-phenyl-5-trifluoromethansulfonoxy-isoxazol-4-yl]benzenesulfonamide;
4-[3-(3,5-difluorophenyl)-5-methylisoxazol-4-yl]benzenesulfonamide;
-4-[3-(4-bromophenyl)-5-methylisoxazol-4-yl]benzenesulfonamide;
4-[5-difluoromethyl-3-(3-fluoro-4-methoxyphenyl)isoxazol-4-yl]benzenesulfonamide;
4-[5-difluoromethyl-3-(4-methoxyphenyl)isoxazol-4-yl]benzenesulfonamide;
4-[5-difluoromethyl-3-(4-methylphenyl)isoxazol-4-yl]benzenesulfonamide;
5-difluoromethyl-4-(4-methylsulfonylphenyl)-3-phenylisoxazole;
4-[3-(3-chlorophenyl)-5-methylisoxazol-4-yl]benzenesulfonamide;
4-[3-(3,4-difluorophenyl)-5-methylisoxazol-4-yl]benzenesulfonamide;
methyl 4-[[4-[4-(aminosulfonyl)phenyl]-3-phenylisoxazol-5-yl]methoxy]benzoate;
4-[[4-[4-(aminosulfonyl)phenyl]-3-phenylisoxazol-5-yl]methoxy]benzoic acid;
4-[3-phenyl-(3,3,3-trifluoro-2-oxopropyl)isoxazol-4-yl]benzenesulfonamide;
4-[3-ethyl-5-phenylisoxazol-4-yl]benzenesulfonamide;
4-[3-isopropyl-5-phenylisoxazol-4-yl]benzenesulfonamide;
4-[5-phenyl-3-propylisoxazol-4-yl]benzenesulfonamide;
4-[3-ethyl-5-(4-methylphenyl)isoxazol-4-yl]benzenesulfonamide;
4-[3-butyl-5-phenylisoxazol-4-yl]benzenesulfonamide;
4-[3-methyl-5-(4-methylphenyl)isoxazol-4-yl]benzenesulfonamide;
4-[5-(4-chlorophenyl)-3-methylisoxazol-4-yl]benzenesulionamide;
4-[5-(4-fluorophenyl)-3-methylisoxazol-4-yl]benzenesulfonamide;
3-methyl-5-(4-methylsulfonylphenyl)-4-phenylisoxazole;
4-[3-methyl-4-phenylisoxazol-5-yl]benzenesulfonamide;
4-[5-(3-chlorophenyl)-3-methylisoxazol-4-yl]benzenesulfonamide;
4-[3-hydroxymethyl-5-phenylisoxazol-4-yl]benzenesulfonamide;
4-(4-aminosulfonylphenyl)-5-phenyl-isoxazole-3-acetic acid;
3-methyl-4-(4-methylsulfonylphenyl)-5-phenylisoxazole;
4-[3-[2-(4-chlorophenyl)-2-hydroxyethyl]-5-phenylisoxazol-4-yl]benzenesulfonamide;
3-ethyl-4-(4-methylsulfonylphenyl)-5-phenylisoxazole;
4-[3-ethyl-5-(4-fluorophenyl)isoxazol-4-yl]benzenesulfonamide;
4-[3-ethyl-5-(3-fluorophenyl)isoxazol-4-yl]benzenesulfonamide;
4-[3-ethyl-5-(3-methylphenyl)isoxazol-4-yl]benzenesulfonamide;
4-[3-ethyl-5-(2-fluorophenyl)isoxazol-4-yl]benzenesulfonamide;
4-[5-(3-chloro-4-methoxyphenyl)-3-ethylisoxazol-4-yl]benzenesulfonamide;
4-[3-ethyl-5-(3-fluoro-4-methoxyphenyl)isoxazol-4-yl]benzenesulfonamide;
4-[3-ethoxyethyloxymethyl-5-phenylisoxazol-4-yl]benzenesulfonamide;
4-[3-ethyl-5-(3-fluoro-4-methylphenyl)isoxazol-4-yl]benzenesulfonamide;
4-[3-isobutyl-5-phenylisoxazol-4-yl]benzenesulfonamide;
4-[3-benzyl-5-phenylisoxazol-4-yl]benzenesulfonamide;
4-(4-aminosulfonylphenyl)-5-phenyl-isoxazole-3-propanoic acid;
4-(4-aminosulfonylphenyl)-5-phenyl-isoxazole-3-butanoic acid;
4-(4-aminosulfonylphenyl)-5-phenyl-isoxazole-3-pentanoic acid;
4-(4-aminosulfonylphenyl)-5-phenyl-isoxazole-3-hexanoic acid;
4-[5-methyl-4-phenylisoxazol-3-yl]benzenesulfonamide;
5-(4-aminosulfonylphenyl)-4-phenyl-isoxazole-3-propanoic acid;
5-(4-aminosulfonylphenyl)-4-phenyl-isoxazole-3-butanoic acid;
5-(4-aminosulfonylphenyl)-4-phenyl-isoxazole-3-pentanoic acid;
5-(4-aminosulfonylphenyl)-4-phenyl-isoxazole-3-hexanoic acid;
4-[3-ethyl-4-phenylisoxazol-5-yl]benzenesulfonamide;
4-[3-isopropyl-4-phenylisoxazol-5-yl]benzenesuifonamide;
4-[3-isobutyl-4-phenylisoxazol-5-yl]benzenesulfonaride;
4-[3-benzyl-4-phenylisoxazol-5-yl]benzenesulfonamide;
4-[3-propyl-4-phenylisoxazol-5-yl]benzenesulfonamide;
4-[4-(4-fluorophenyl)-3-methylisoxazol-5-yl]benzenesulfonamide;
4-[3-methyl-4-(4-methylphenyl)isoxazol-5-yl]benzenesulfonamide;
4-[3-methyl-4-(4-trifluoromethylphenyl)isoxazol-5-yl]benzenesulfonamide;
4-[3-ethyl-4-(4-methylphenyl)isoxazol-5-yl]benzenesulfonamide;
4-[3-ethyl-4-(4-trifluoromethylphenyl)isoxazol-5-yl]benzenesulfonamide;
4-[3-ethyl-4-(4-fluorophenyl)isoxazol-5-yl]benzenesulfonamide;
[3-(3-fluoro-4-methoxyphenyl)-4-[4-(methylsulfonyl)phenyl]isoxazol-5-yl]acetic acid;
[3-(3-chloro-4-methoxyphenyl)-4-[4-(methylsulfonyl)phenyl]isoxazol-5-yl]acetic acid;
5-methyl-4-[4-(methylsulfonyl)phenyl]-3-phenylisoxazole;
3-(3-chloro-4-methoxyphenyl)-5-methyl-4-[4-(methylsulfonyl)phenyl]isoxazole;
3-(3-chloro-4-methoxyphenyl)-5-ethyl-4-[4-(methylsulfonyl)phenyl]isoxazole;
3-(3-fluoro-4-methoxyphenyl)-5-ethyl-4-[4-(methylsulfonyl)phenyl]isoxazole;
3-(3,4-dichlorophenyl)-5-methyl-4-[4-(methylsulfonyl)phenyl]isoxazole;
3-(3,4-difluorophenyl)-5-methyl-4-[4-(methylsulfonyl)phenyl]isoxazole;
3-(3,5-difluoro-4-methoxyphenyl)-5-methyl-4-[4-(methylsulfonyl)phenyl]isoxazole;
3-(4-methoxyphenyl)-5-methyl-4-[4-(methylsulfonyl)phenyl]isoxazole;

3-(4-chlorophenyl)-5-methyl-4-[4-(methylsulfonyl)phenyl] isoxazole;
3-(4-fluorophenyl)-5-methyl-4-[4-(methylsulfonyl)phenyl] isoxazole;
3-(4-methylphenyl)-5-methyl-4-[4-(methylsulfonyl)phenyl] isoxazole;
4-[5-ethyl-3-phenylisoxazol-4-yl]benzenesulfonamide;
4-[5-propyl-3-phenylisoxazol-4-yl]benzenesulfonamide;
4-[5-isopropyl-3-phenylisoxazol-4-yl]benzenesulfonamide;
4-[5-butyl-3-phenylisoxazol-4-yl]benzenesulfonamide;
4-[5-isobutyl-3-phenylisoxazol-4-yl]benzenesulfonamide;
4-[5-cyclohexyl-3-phenylisoxazol-4-yl] benzenesulfonamide;
4-[5-neopentyl-3-phenylisoxazol-4-yl]benzenesulfonamide;
4-[5-cyclohexylmethyl-3-phenylisoxazol-4-yl] benzenesulfonamide;
4-[5-(4-chlorophenyl)methyl-3-phenylisoxazol-4-yl] benzenesulfonamide;
4-[5-trifluoromethyl-3-phenylisoxazol-4-yl] benzenesulfonamide;
4-[5-difluoromethyl-3-phenylisoxazol-4-yl] benzenesulfonamide;
4-[5-chloromethyl-3-phenylisoxazol-4-yl] benzenesulfonamide;
4-[5-methyl-3-phenylisoxazol-4-yl]benzenesulfonic acid;
4-[5-propyl-3-phenylisoxazol-4-yl]benzenesulfonic acid;
4-[5-methoxymethyl-3-phenylisoxazol-4-yl] benzenesulfonamide;
4-[5-(3-hydroxypropyl)-3-phenylisoxazol-4-yl] benzenesulfonamide;
4-[3-(4-chlorophenyl)-5-methylisoxazol-4-yl] benzenesulfonamide;
4-[3-(4-fluorophenyl)-5-methylisoxazol-4-yl] benzenesulfonamide;
4-[3-(3-fluoro-4-methylphenyl)-5-methylisoxazol-4-yl] benzenesulfonamide;
4-[3-(3-aminosulfonyl-4-methoxyphenyl)-5-methylisoxazol-4-yl]benzenesulfonamide;
4-[3-(3-chloro-4-methylphenyl)-5-methylisoxazol-4-yl] benzenesulfonamide;
4-[5-methyl-3-(3-pyridyl)isoxazol-4-yl] benzenesulfonamide;
4-[5-methyl-3-(4-pyridyl)isoxazol-4-yl] benzenesultonamide;
4-[3-(3-fluorophenyl)-5-methylisoxazol-4-yl] benzenesulfonamide;
4-[5-hydroxymethyl-3-phenylisoxazol-4-yl] benzenesulfonamide;
[4-[4-(aminosulfonyl)phenyl]-3-phenylisoxazol-5-yl] carboxylic acid;
4-[5-hydroxy-3-phenylisoxazol-4-yl]benzenesulfonamide;
4-[3-methyl-5-phenylisoxazol-4-yl]benzenesulfonamide;
4-[5-methyl-3-phenylisoxazol-4-yl]benzenesulfonamide;
4-[3-(3-fluoro-4-methoxyphenyl)-5-methylisoxazol-4-yl] benzenesulfonamide;
4-[3-(4-methoxyphenyl)-5-methylisoxazol-4-yl] benzenesulfonamide;
4-[3-(3,5-difluoro-4-methoxyphenyl)-5-methylisoxazol-4-yl]benzenesulfonamide;
4-[3-(3-chloro-4-methoxyphenyl)-5-methylisoxazol-4-yl] benzenesulfonamide;
4-[3-(3,5-dichloro-4-methoxyphenyl)-5-methylisoxazol-4-yl]benzenesulfonamide;
4-[3-(4-methylphenyl)-5-methylisoxazol-4-yl] benzenesulfonamide;
4-[5-methyl-3-(4-trifluoromethoxyphenyl)isoxazol-4-yl] benzenesulfonamide;
4-[5-methyl-3-(4-trifluoromethylphenyl)isoxazol-4-yl] benzenesulfonamide;
4-[3-(4-cyanophenyl)-5-methylisoxazol-4-yl] benzenesulfonamide;
4-[3-(4-methylsulfinylphenyl)-5-methylisoxazol-4-yl] benzenesulfonamide;
4-[3-(4-methylthiophenyl)-5-methylisoxazol-4-yl] benzenesulfonamide;
4-[3-(4-hydroxymethylphenyl)-5-methylisoxazol-4-yl] benzenesulfonamide;
4-[5-ethyl-3-(3-fluoro-4-methoxyphenyl)isoxazol-4-yl] benzenesulfonamide;
4-[5-benzyl-3-(3-fluoro-4-methoxyphenyl)isoxazol-4-yl] benzenesulfonamide;
4-[3-(3-fluoro-4-methoxyphenyl)-5-methoxyisoxazol-4-yl] benzenesulfonamide;
4-[3-(3-fluoro-4-methoxyphenyl)-5-phenoxymethylisoxazol-4-yl]benzenesulfonamide;
4-[5-benzyloxymethyl-3-(3-fluoro-4-methoxyphenyl) isoxazol-4-yl]benzenesulfonamide;
4-[3-(3-fluoro-4-methoxyphenyl)-5-methoxymethylisoxazol-4-yl]benzenesulfonamide;
4-[3-(3-fluoro-4-methoxyphenyl)-5-methylthiomethylisoxazol-4-yl]benzenesulfonamide;
4-[3-(3-fluoro-4-methoxyphenyl)-5-(3-thienyl) methylthioisoxazol-4-yl]benzenesulfonamide;
4-[3-(3-fluoro-4-methoxyphenyl)-5-methoxycarbonylmethylisoxazol-4-yl] benzenesulfonamide;
4-[5-(aminocarbonylmethyl)-3-(3-fluoro-4-methoxyphenyl) isoxazol-4-yl]benzenesulfonamide;
4-[3-(3-fluoro-4-methoxyphenyl)-5-(methylthio)isoxazol-4-yl]benzenesulfonamide;
4-[3-(3-fluoro-4-methoxyphenyl)-5-(trifluoromethoxy) isoxazol-4-yl]benzenesulfonamide;
4-[3-(3-fluoro-4-methoxyphenyl)-5-(N-methylamino) isoxazol-4-yl]benzenesulfonamide;
[4-[4-(aminosulfonyl)phenyl]-3-phenylisoxazol-5-yl]acetic acid;
[4-[4-(aminosulfonyl)phenyl]-3-phenylisoxazol-5-yl] carboxamide;
methyl [4-[4-(aminosulfonyl)phenyl]-3-phenylisoxazol-5-yl]acetate;
[4-[4-(aminosulfonyl)phenyl]-3-phenylisoxazol-5-yl] propanoic acid;
ethyl [4-[4-(aminosulfonyl)phenyl]-3-phenylisoxazol-5-yl] propanoate; and
[4-[4-(aminosulfonyl)phenyl]-3-(3-fluoro-4-methoxyphenyl)isoxazol-5-yl]propanoic acid.

A second family of specific compounds of particular interest within Formula I consists of compounds and pharmaceutically-acceptable salts thereof as follows:
4-[5-(2-hydroxyethyl)-3-phenylisoxazol-4-yl] benzenesulfonamide;
4-[5-(2-methyl-2-hydroxy-1-n-propyloxymethyl)-3-phenylisoxazol-4-yl]benzenesulfonamide;
4-[5-(4-hydroxy-4-methylpentyl)-3-phenylisoxazol-4-yl] benzenesulfonamide;
[4-[4-(aminosulfonyl)phenyl]-3-phenylisoxazol-5-yl]-3-methylbutan-1-oic acid;
[[4-[4-(aminosulfonyl)phenyl]-3-phenylisoxazol-5-yl]-methyloxy]acetic acid;
4-[4-[4-(aminosulfonyl)phenyl]]-3-phenylisoxazol-5-yl] butanoic acid;
4-[5-cyano-3-phenylisoxazol-4-yl]benzenesulfonamide;
4-[5-chloro-3-phenylisoxazol-4-yl]benzenesulfonamide;
4-[3-phenyl-5-(trifluoromethansulfonoxy)isoxazol-4-yl] benzenesulfonamide;

4-[3-(3,5-difluorophenyl)5-methylisoxazol-4-yl]
benzenesulfonamide;
4-[3-(4-bromophenyl)-5-methylisoxazol-4-yl]
benzenesulfonamide;
4-[5-difluoromethyl-3-(3-fluoro-4-methoxyphenyl)
isoxazol-4-yl]benzenesulfonamide;
4-[5-difluoromethyl-3-(4-methoxyphenyl)isoxazol-4-yl]
benzenesulfonamide;
4-[5-difluoromethyl-3-(4-methylphenyl)isoxazol-4-yl]
benzenesulfonamide;
5-difluoromethyl-4-(4-methylsulfonylphenyl)-3-
phenylisoxazole;
4-[3-(3-chlorophenyl)-5-methylisoxazol-4-yl]
benzenesulfonamide;
4-[3-(3,4-difluorophenyl)-5-methylisoxazol-4-yl]
benzenesulfonamide;
methyl 4-[4-[4-(aminosulfonyl)phenyl]-3-phenylisoxazol-
5-methoxy]benzoate;
4-[4-[4-(aminosulfonyl)phenyl]-3-phenylisoxazol-5-
methoxy]benzoic acid;
4-[3-ethyl-5-phenylisoxazol-4-yl]benzenesulfonamide;
4-[3-isopropyl-5-phenylisoxazol-4-yl]benzenesulfonamide;
4-[5-phenyl-3-propylisoxazol-4-yl]benzenesulfonamide;
4-[3-ethyl-5-(4-methylphenyl)isoxazol-4-yl]
benzenesulfonamide;
4-[3-butyl-5-phenylisoxazol-4-yl]benzenesuifonamide;
4-[3-methyl-5-(4-methylphenyl)isoxazol-4-yl]
benzenesulfonamide;
4-[5-(4-chlorophenyl)-3-methylisoxazol-4-yl]
benzenesulfonamide;
4-[5-(4-fluorophenyl)-3-methylisoxazol-4-yl]
benzenesulfonamide;
3-methyl-5-(4-methylsulfonylphenyl)-4-phenylisoxazole;
4-[3-methyl-4-phenylisoxazol-5-yl]benzenesulfonamide;
4-[3-methyl-5-(3-chlorophenyl)isoxazol-4-yl]
benzenesulfonamide;
4-[3-hydroxymethyl-5-phenylisoxazol-4-yl]
benzenesulfonamide;
4-(4-aminosulfonylphenyl)-5-phenyl-isoxazole-3-acetic
acid;
3-methyl-4-(4-methylsulfonylphenyl)-5-phenylisoxazole;
4-[3-[2-(4-chlorophenyl)-2-hydroxyethyl]-5-
phenylisoxazol-4-yl]benzenesulfonamide;
3-ethyl-4-(4-methylsulfonylphenyl)-5-phenylisoxazole;
4-[3-ethyl-5-(4-fluorophenyl)isoxazol-4-yl]
benzenesulfonamide;
4-[3-ethyl-5-(3-fluorophenyl)isoxazol-4-yl]
benzenesulfonamide;
4-[3-ethyl-5-(3-methylphenyl)isoxazol-4-yl]
benzenesulfonamide;
4-[3-ethyl-5-(2-fluorophenyl)isoxazol-4-yl]
benzenesulfonamide;
4-[5-methyl-4-phenylisoxazol-3-yl]benzenesulfonamide;
4-[5-ethyl-3-phenylisoxazol-4-yl]benzenesulfonamide;
4-[3-phenyl-5-propylisoxazol-4-yl]benzenesulfonamide;
4-[5-isopropyl-3-phenylisoxazol-4-yl]benzenesulfonamide;
4-[5-butyl-3-phenylisoxazol-4-yl]benzenesulfonamide;
4-[5-isobutyl-3-phenylisoxazol-4-yl]benzenesulfonamide;
4-[5-cyclohexyl-3-phenylisoxazol-4-yl]
benzenesulfonamide;
4-[5-neopentyl-3-phenylisoxazol-4-yl]benzenesulfonamide;
4-[5-cyclohexylmethyl-3-phenylisoxazol-4-yl]
benzenesulfonamide;
4-[5-(4-chlorophenyl)methyl-3-phenylisoxazol-4-yl]
benzenesulfonamide;
4-[5-trifluoromethyl-3-phenylisoxazol-4-yl]
benzenesulfonamide;
4-[5-difluoromethyl-3-phenylisoxazol-4-yl]
benzenesulfonamide;
4-[5-chloromethyl-3-phenylisoxazol-4-yl]
benzenesulfonamide;
4-[5-methyl-3-phenylisoxazol-4-yl]benzenesulfonic acid;
4-[5-propyl-3-phenylisoxazol-4-yl]benzenesulfonic acid;
4-[5-methoxymethyl-3-phenylisoxazol-4-yl]
benzenesulfonamide;
4-[5-(3-hydroxypropyl)-3-phenylisoxazol-4-yl]
benzenesulfonamide;
4-[3-(4-chlorophenyl)-5-methylisoxazol-4-yl]
benzenesulfonamide;
4-[3-(4-fluorophenyl)-5-methylisoxazol-4-yl]
benzenesulfonamide;
4-[3-(3-fluoro-4-methylphenyl)-5-methylisoxazol-4-yl]
benzenesulfonamide;
4-[3-(3-aminosulfonyl-4-methoxyphenyl)-5-
methylisoxazol-4-yl]benzenesulfonamide;
4-[3-(3-chloro-4-methylphenyl)-5-methylisoxazol-4-yl]
benzenesulfonamide;
4-[5-methyl-3-(3-pyridyl)isoxazol-4-yl]
benzenesulfonamide;
4-[5-methyl-3-(4-pyridyl)isoxazol-4-yl]
benzenesulfonamide;
4-[3-(3-fluorophenyl)-5-methylisoxazol-4-yl]
benzenesulfonamide;
4-[5-hydroxymethyl-3-phenylisoxazol-4-yl]
benzenesulfonamide;
[4-[4-(aminosulfonyl)phenyl]-3-phenylisoxazol-5-yl]
carboxylic acid;
4-[5-hydroxy-3-phenylisoxazol-4-yl]benzenesulfonamide;
4-[3-methyl-5-phenylisoxazol-4-yl]benzenesulfonamide;
4-[5-methyl-3-phenylisoxazol-4-yl]benzenesulfonamide;
4-[3-(3-fluoro-4-methoxyphenyl)-5-methylisoxazol-4-yl]
benzenesulfonamide;
[3-(3-chloro-4-methoxyphenyl)-4-[4-(methylsulfonyl)
phenyl]isoxazol-5-yl]acetic acid;
5-methyl-4-[4-(methylsulfonyl)phenyl]-3-phenylisoxazole;
3-(3-chloro-4-methoxyphenyl)-5-methyl-4-[4-
(methylsulfonyl)phenyl]isoxazole;
[4-[4-(aminosulfonyl)phenyl]-3-phenylisoxazol-5-yl]acetic
acid;
[4-[4-(aminosulfonyl)phenyl]-3-phenylisoxazol-5-yl]
propanoic acid;
ethyl [4-[4-(aminosulfonyl)phenyl]-3-phenylisoxazol-5-yl]
propanoate;
[4-[4-(aminosulfonyl)phenyl]-3-(3-fluoro-4-
methoxyphenyl)isoxazol-5-yl]propanoic acid; and
[3-(3-fluoro-4-methoxyphenyl)-4-[4-(methylsulfonyl)
phenyl]isoxazol-5-yl]acetic acid.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially saturated carbocyclic radicals having three to twelve carbon atoms. More preferred cycloalkenyl radicals are "lower cycloalkenyl" radicals having three to about eight carbon atoms. Examples of such radicals include cyclobutenyl, cyclopentenyl and cyclohexenyl. The term "halo" means halogens such as fluoro, chloro, bromo or iodo. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The terms "hydroxyalkyl" and "hydroxylalkyl" embrace linear or branched alkyl radicals having one to about ten carbon atoms any one of which may be substituted with one or more hydroxyl radicals. More preferred "hydroxyalkyll" radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide "haloalkoxy" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cycloalkylalkoxy" embraces radicals having cycloalkyl radicals, as defined above, attached to an alkoxy radical. More preferred "cycloalkylalkoxy" radicals are "lower cycloalkylalkoxy" radicals having cycloalkyl radicals of three to six carbon atoms attached to an alkoxy radical of one to six carbon atoms. Examples of such radicals include cyclohexylmethoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The terms "heterocyclic" and "heterocyclo" embrace saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclic group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4- thiadiazolyl, 1,3,4-thiadiazolyl, 1,2,5-thiadiazolyl, etc.) etc.; unsaturated condensed heterocyclic group containing 1 to 2 sulfur atoms and 1 to 3 nitrogen atoms (e.g., benzothiazolyl, benzothiadiazolyl, etc.) and the like. The term also embraces radicals where heterocyclic radicals are fused with aryl radicals. Examples of such fused bicyclic radicals include benzofuran, benzothiophene, and the like. Said "heterocyclic group" may have 1 to 3 substituents such as lower alkyl, hydroxy, oxo, amino and lower alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "cycloalkylalkylthio" embraces radicals having cycloalkyl radicals, as defined above, attached to an alkylthio radical. More preferred cycloalkylthio radicals are "lower cycloalkylalkylthio" radicals having cycloalkyl radicals of three to six carbon atoms. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote H$_2$NO$_2$S—. The term "hydroxysulfonyl" denotes HO(O$_2$)S—. The terms "carboxy" or "carboxyl", whether used alone or with other terms, such as "carboxyalkyl", denotes —CO$_2$H. The term "carboxyalkyl" embraces alkyl radicals substituted with a carboxy radical. More preferred are "lower carboxyalkyl" which embrace lower alkyl radicals as defined above. Examples of such lower carboxyalkyl radicals include carboxymethyl, carboxyethyl, carboxypropyl and carboxybutyl. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbon atom of a carbonyl radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" means a radical containing an alkoxycarbonyl radical, as defined above, attached to an alkyl radical. Examples of such "alkoxycarbonylalkyl" ester radicals include substituted or unsubstituted methoxycarbonylmethyl, butoxycarbonylmethyl and hexyloxycarbonylethyl. The terms "alkylcarbonyl", "arylcarbonyl" and "aralkylcarbonyl", include radicals having alkyl, aryl and aralkyl radicals, as defined above, attached to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals. More preferred aralkyl radicals are "lower aralkyl" radicals having aryl substituted lower alkyl radicals, as defined above. Examples include benzyl, diphenylmethyl, triphenylmethyl, phenylethyl, and diphenylethyl. The aryl in said aralkyl may be additionally substituted with halo, alkyl, alkoxy, haloalkyl and haloalkoxy. The terms benzyl and phenylmethyl are interchangeable. The term "heterocycloalkyl" embraces heterocyclo-substituted alkyl radicals, such as pyrrolidinylmethyl, piperazinylmethyl, piperidinylmethyl, furanylethyl, tetrahydrofurylethyl and heteroaralkyl radicals. The term "heteroaralkyl" embraces heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "cycloalkylalkyl" embraces radicals having cycloalkyl radicals, as defined above, attached to an alkyl radical. More preferred "cycloalkylalkyl" radicals are "lower cycloalkylalkyl" radicals having cycloalkyl radicals of three to six carbon atoms attached to an alkyl radical of one to six carbon atoms. The term "cycloalkylalkyl" embraces cycloalkyl-substituted alkyl radicals such as cyclohexylmethyl, cyclopentylethyl, cyclopentylmethyl, cyclohexylethyl, and cyclobutylpropyl. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "heteroaralkoxy" embraces heteroaralkyl radicals attached through an oxygen atom to other radicals. The term "heteroaralkylthio" embraces heteroaralkyl radicals attached through a sulfur atom to other radicals. The term "aminoalkyl" embraces alkyl radicals substituted with amino radicals. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "cycloalkylamino" denotes amino groups which have been substituted with one or two cycloalkyl radicals, as defined above. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The term "heteroaralkylamino" embraces heteroaralkyl radicals, as defined above, attached through an nitrogen atom to other radicals. The term "aminocarbonyl" denotes an amide group of the formula —C(=O)NH$_2$. The term "alkylcarbonylaminoalkyl" embraces radicals having one or more alkyl radicals attached to a carbonyl radical further attached to an aminoalkyl radical. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom. The terms "N-alkyl-N-aralkylamino" "N-alkyl-N-heteroaralkylamino", and "N-alkyl-N-cycloalkylalkylamino" embrace amino radicals substituted with one alkyl radical and with an aralkyl, heteroaralkyl or cycloalkylalkyl radical, respectively. The term "alkoxyalkyloxyalkyl" or "alkoxyalkoxyalkyl" denotes radicals having alkoxy radicals attached to an alkoxyalkyl radical as defined above. The term "aryl(hydroxylalkyl)" denotes a radical having an aryl radical attached to a hydroxyalkyl radical. The aryl portion may be optionally further substituted with alkyl, halo, alkoxy and the like. The term "haloalkylsulfonyloxy" denotes radicals having a haloalkyl substituted sulfonyl radical, which is attached to other radicals via a divalent oxygen atom. An example of a haloalkylsulfonyloxy radical is "trifluorosulfonyloxy." The terms "arylcarbonyloxyalkyl," "alkylaminocarbonyloxyalkyl," and "alkoxycarbonyloxyalkyl," denote —C(O)—O-alkyl radicals substituted with aryl, alkylamino, and alkoxy radicals, respectively. The terms "alkoxycarbonylthioalkyl," "arylcarbonylthioalkyl", and "alkylaminocarbonylthioalkyl," denote —C(O)—S-alkyl radicals substituted with alkoxy, aryl and alkylamino radicals, respectively. The term "carboxyalkoxyalkyl" denotes carboxy substituted alkoxyalkyl radicals, as defined above. The term "carboxyaryloxyalkyl" denotes carboxy substituted aryloxyalkyl radicals, as defined above. The term "alkoxycarbonylaryloxyalkyl" denotes alkoxycarbonyl substituted alkoxyalkyl radicals, as defined above.

Compounds of Formula I, where R$^3$ is a nitrogen containing heteroaryl radical, would also be capable of inhibiting cytokines, such as TNF, IL-1, IL-6, and IL-8. As such, the compounds can be used in the manufacture of a medicament or in a method for the treatment for the prophylactic or therapeutic treatment of diseases mediated by cytokines, such as TNF, IL-1, IL-6, and IL-8.

The present invention comprises a pharmaceutical composition comprising a therapeutically-effective amount of a compound of Formulas I–V in association with at least one pharmaceutically-acceptable carrier, adjuvant or diluent.

The present invention also comprises a method of treating cyclooxygenase-2 associated disorders, such as inflammation, in a subject, the method comprising treating the subject having such disorder with a therapeutically-effective amount of a compound of Formulas I–V.

Also included in the family of compounds of Formulas I–V are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I–V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, galactaric and galacturonic acid. Suitable pharmaceutically-acceptable base addition salts of compounds of Formulas I–IV include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formulas I–V by reacting, for example, the appropriate acid or base with the compound of Formulas I–V.

GENERAL SYNTHETIC PROCEDURES

The compounds of the invention can be synthesized according to the following procedures of Schemes I–XVII, wherein the $R^1$–$R^{14}$ substituents are as defined for Formulas I–V, above, except where further noted.

Scheme I

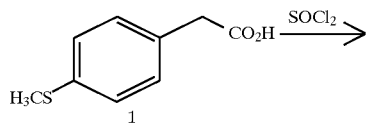

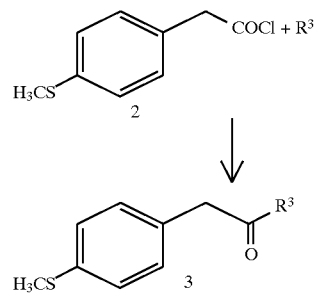

Scheme I illustrates the two step procedure used to prepare substituted desoxybenzoin derivatives 3. In step one, 4-methylthiophenylacetic acid 1 is converted to the corresponding acid chloride 2 with thionyl chloride. A variety of aromatic compounds are then acylated with 2 in the presence of a Lewis acid such as aluminum chloride to provide the desired desoxybenzoins 3 in high yield. This Friedel Crafts acylation can be performed in an inert solvent, such as dichloromethane, chloroform, nitrobenzene, 1,2-dichloroethane, 1,2-dichlorobenzene and similar solvents.

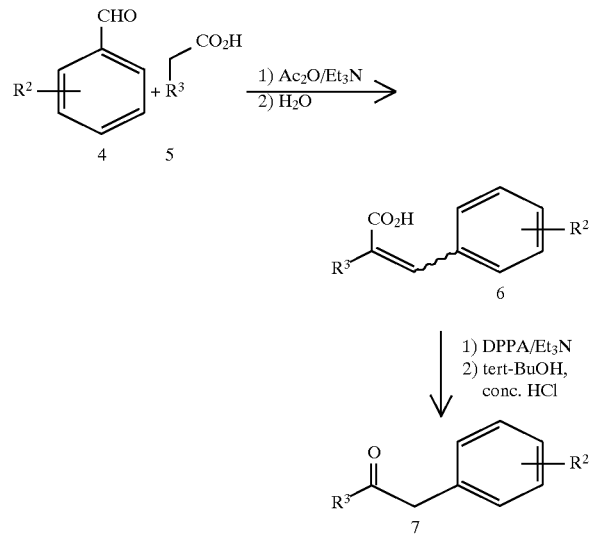

Synthetic Scheme II shows the four step procedure which can be used to prepare substituted ketone compounds 7 from aldehyde 4 and acid 5. In step one, aldehyde 4 and substituted acetic acid 5 are heated together in acetic anhydride and triethylamine to form the 2,3-disubstituted acrylic acids 6 via a Perkin condensation. In step two, the addition of water produces the acids 6 free from any mixed acetic-acrylic anhydrides. The acrylic acids 6 are reacted with diphenylphosphorylazide (DPPA) and triethylamine in toluene at about 0° C. and then at room temperature to form acylazides. The crude acylazides are heated to form a vinyl isocyanate via a Curtius rearrangement. The vinyl isocyanates are trapped with tert-butyl alcohol to produce N-tert-butoxycarbonyl enamine derivatives. Acidic hydrolysis using concentrated HCl provides the substituted ketone 7 intermediates.

Scheme III

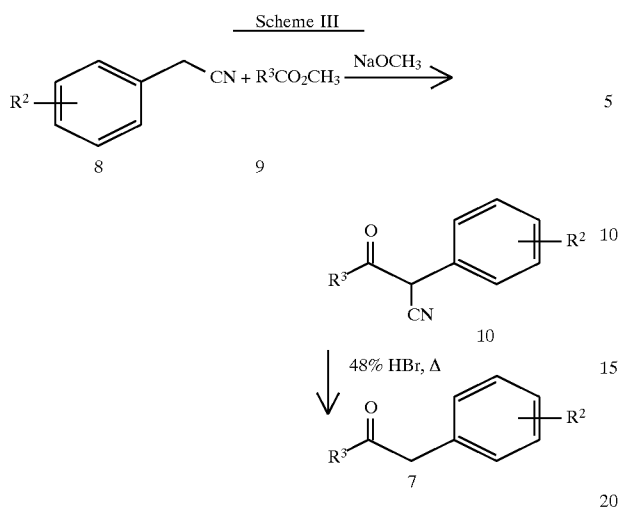

Synthetic Scheme III illustrates an alternative approach which can be used to prepare substituted ketone intermediates 7 via the Claisen reaction of a substituted phenylacetonitrile 8 and a acid ester 9. In the first step, a mixture of substituted phenylacetonitrile 8 and acid ester 9 are treated with a base such as sodium methoxide in a protic solvent like methanol to provide the cyanoketone 10. In step two, the cyanoketone 10 is hydrolyzed in aqueous acid such as concentrated HBr to effect hydrolysis of the nitrile and decarboxylation of the incipient carboxylic acid to produce the substituted ketone intermediates 7.

Other synthetic approaches are possible to form the desired ketones 7. These alternatives include reacting the appropriate Grignard or lithium reagents with Weinreb amides of substituted acids or acetic acids. The Weinreb methodology has been reported in *Tetrahedron Letters*, 4171 (1977)

Scheme IV

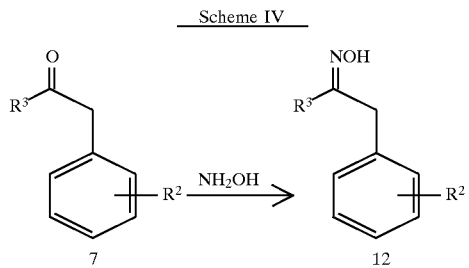

Synthetic Scheme IV shows the procedure which can be used for the preparation of oxime intermediates 12. Treatment of ketone intermediates 7 with hydroxylamine, as an aqueous solution or prepared from hydroxylamine hydrochloride by treatment with base, provides the oxime intermediates 12. Preferably, the reaction is performed at reflux temperatures, and more preferred at a temperature of about 70° to about 75° C. A wide variety of solvents can be used for this reaction including alcohols, toluene and tetrahydrofuran. Preferably, the solvent is selected from ethanol and aqueous ethanol. More preferred is aqueous ethanol. Preferably, a slight excess of hydroxylamine hydrochloride and base is used. More preferably, about 1.05 to about 2 equivalents of hydroxylamine hydrochloride is added. Even more preferably, about 1.1 to about 1.3 equivalents of hydroxylamine hydrochloride is added. Preferably, the base is selected from potassium hydroxide, sodium acetate and sodium acetate trihydrate. More preferably, sodium acetate is used.

Scheme V

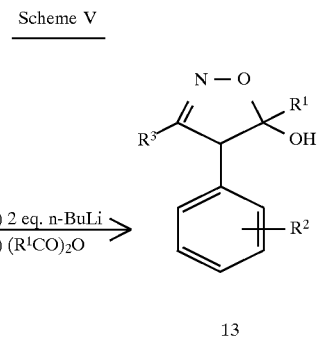

Synthetic Scheme V shows the procedure which can be used for the preparation of hydrated isoxazole derivatives 13. The substituted oximes 12 are treated with about two equivalents of a base to produce a dianion which is subsequently acylated. Preferably, the base is selected from n-butyllithium and lithium diisopropylamide (LDA). More preferred is the use of LDA. The base addition can be run at a temperature in the range of about −30° C. to about 20° C. Preferably, the reaction is run at a temperature in the range of about −20° C. to about −10° C. Suitable acylating agents are anhydrides, acyl imidazoles, esters and the like. Preferably, esters are used as the acylating agent. More preferably, methyl acetate is used. Preferably, the acylation is run at a temperature below about 25° C. Upon quenching the reaction mixture with dilute aqueous acid, hydrated isoxazole derivatives 13 can be isolated by crystallization, distillation or chromatography. Preferably, hydrochloric acid is used.

Scheme VI

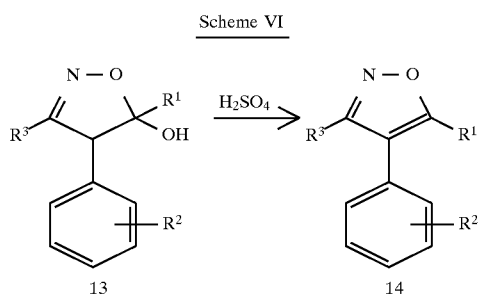

Synthetic Scheme VI shows the procedure which can be used for the preparation of isoxazole analogs 14 by dehydration of the hydrated isoxazole derivatives 13. Substituted hydrated isoxazoles 13 are dissolved in an appropriate solvent such as toluene and then treated with a catalytic to stoichiometric amount of concentrated sulfuric acid to effect dehydration and thereby produce isoxazole derivatives 14. Other acids can also be employed to effect this transformation such as concentrated HCl, concentrated HBr and many others.

Scheme VII

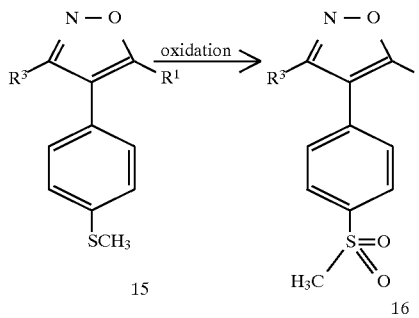

Synthetic Scheme VII shows the procedure which can be used for the preparation of substituted 4-[4-(methylsulfonyl) phenyl]isoxazole analogs 16 from the corresponding 4-[4-(methylthio)phenyl]isoxazoles 15. The oxidation of an aromatic methythio derivative 15 to the corresponding aromatic methylsulfonyl compound 16 can be accomplished in a variety of ways such as with two equivalents of meta-chloroperoxybenzoic acid (MCPBA), two equivalents of Oxone® (potassium peroxymonosulfate) and many other oxidizing agents.

Scheme VIII

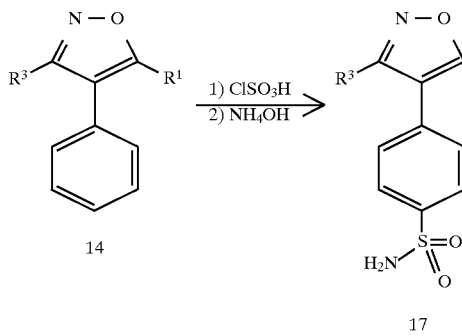

Synthetic Scheme VIII shows the procedure which can be used for the preparation of substituted 4-(4-aminosulfonyl) phenylisoxazole analogs 17 from the corresponding 4-phenylisoxazoles 14 or hydroxy isoxazolines 13. The procedure is a two step process for the direct introduction of the sulfonamide moiety into 4-phenylisoxazoles 14 or hydrated isoxazoles 13. In step one, isoxazole 14 or hydrated isoxazole 13 is treated at a temperature selected from the range of about 0° C. to about 40° C., with more than two equivalents of chlorosulfonic acid to form the corresponding sulfonyl chloride. Preferably about 2 to about 9 equivalents of acid are used. More preferred, about 5 equivalents of acid are used. A preferred temperature range is about 20° C. to about 40° C. In step two, the sulfonyl chloride thus formed is treated with ammonia, and preferably concentrated ammonia hydroxide, to provide the sulfonamide derivative 17. Further purification can be achieved by recrystallization, such as from aqueous alcohols.

Scheme IX

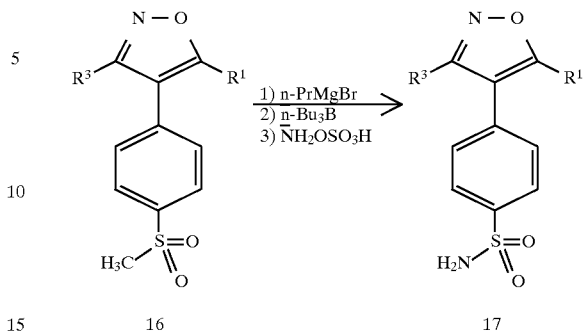

Synthetic Scheme IX shows the three step procedure used to prepare sulfonamide antiinflammatory agents 17 from their corresponding methyl sulfones 16. In step one, a tetrahydrofuran solution (THF) of the methyl sulfones 16 are treated with an alkyllithium or alkylmagnesium (Grignard) reagent at −78° C., such as n-propyl magnesium bromide. In step two, the anion generated in step one is treated with an organoborane, such as tri-n-butylborane at −78° C., warmed to room temperature and heated to reflux. In step three, an aqueous solution of hydroxylamine-o-sulfonic acid is added to provide the corresponding sulfonamide antiinflammatory agents 17. This procedure is essentially that of Huang et. al., *Tetrahedron Letters*, 35, 7204 (1994).

Scheme X

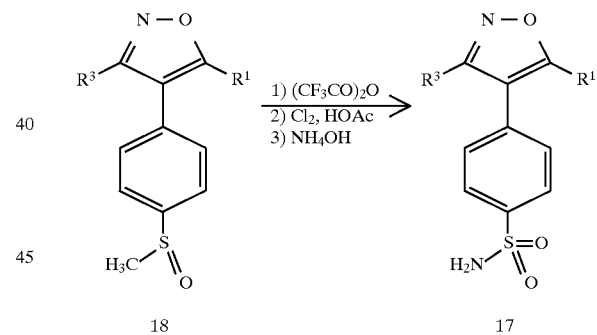

Synthetic Scheme X shows the three step procedure used to prepare sulfonamide antiinflammatory agents 17 from their corresponding methylsulfinyl analogs 18. Methylsulfinyl derivatives 18 are available from the corresponding methylthio compounds 15 by oxidation with one equivalent of an oxidizing agent such as MCPBA. In step one, the methylsulfinyl compounds 18 are treated with trifluoroacetic anhydride to effect Pummerer rearrangement. In step two, the crude Pummerer rearrangement product dissolved in acetic acid is treated with chlorine gas to produce a sulfonyl chloride. In step three, the sulfonyl chloride is converted to the corresponding sulfonamide antiinflammatory agents 17 by treatment with concentrated ammonia. This procedure was adapted from Kharash, *J. Am. Chem. Soc.*, 73, 3240 (1951).

Scheme XI

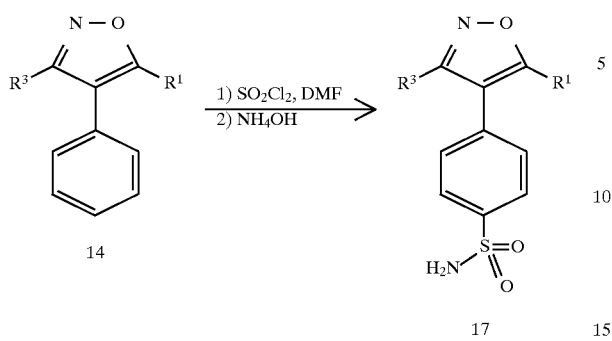

Synthetic Scheme XI shows the two step procedure used to prepare sulfonamide antiinflammatory agents 17 from their corresponding 4-phenyl isoxazole derivatives 14. In step one a mixture of sulfuryl chloride and dimethylformamide (DMF) is reacted at room temperature, mixed with 4-phenylisoxazoles 14 and heated to about 100° C. The sulfonyl chloride thus formed is treated with an excess of concentrated ammonia to provide the antiinflammatory sulfonamides 17.

Scheme XII

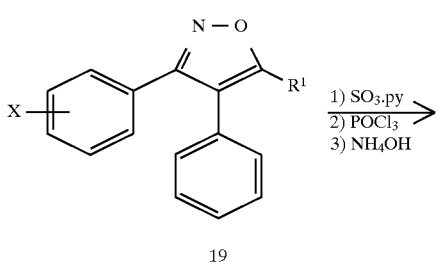

Scheme XII

-continued

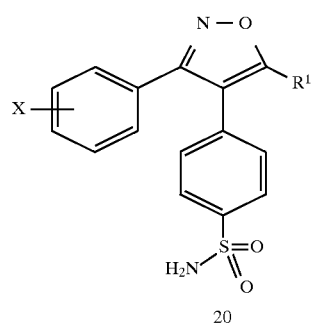

Synthetic Scheme XII shows the three step procedure used to prepare sulfonamide antiinflammatory agents 20 from 4-phenyl isoxazoles 19. In step one, the 4-phenylisoxazoles 19 are converted into the corresponding sulfonic acid by treatment with sulfur trioxide pyridine complex at about 100° C. In step two, the sulfonic acid is converted into the sulfonyl chloride by the action of phosphorus oxychloride. In step three, the sulfonyl chloride is treated with excess concentrated ammonia to provide the antiinflammatory sulfonamides 20.

Scheme XIII

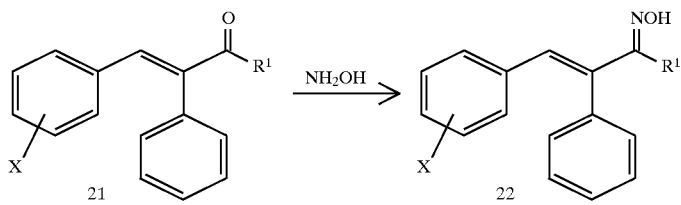

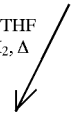

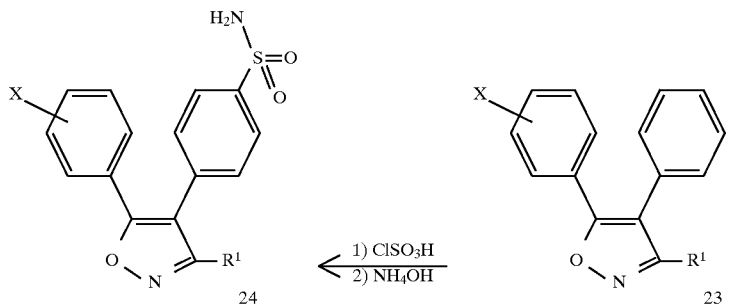

Synthetic Scheme XIII shows the three step procedure used to prepare 4,5-diphenylisoxazole antiinflammatory agents 24 from 1,2-diphenylbutenones 21. In step one, the 1,2-diphenylketones 21 are converted to the corresponding oximes 22 by treatment with hydroxylamine in a manner similar to that shown in Scheme IV. In step two, the oxime 22 is converted to the 4,5-diphenylisoxazole 23. The oxime 22 is reacted with potassium iodide and iodine in the presence of base, such as sodium bicarbonate and heated to form isoxazole 23. The isoxazole 23 is converted to the sulfonamide by any of the procedures shown in Schemes VIII, XI or XII.

substituted desoxybenzoin 25 is converted to the corresponding sulfonamide derivative 26 by treatment with chlorosulfonic acid followed by conversion of the incipient sulfonyl chloride to the sulfonamide by treatment with aqueous ammonia. In the second step, the sulfonamide 26 is protected as the 2,5-dimethylpyrrole derivative by treatment with acetonylacetone in the presence of hydrochloric acid and ethanol. The 2,5-dimethylpyrrole thus formed is converted into oxime 27 by treatment with hydroxylamine hydrochloride in the presence of sodium acetate in aqueous ethanol. The oxime 27 is treated with slightly more than two equivalents of lithium diisopropylamide (LDA). The result-

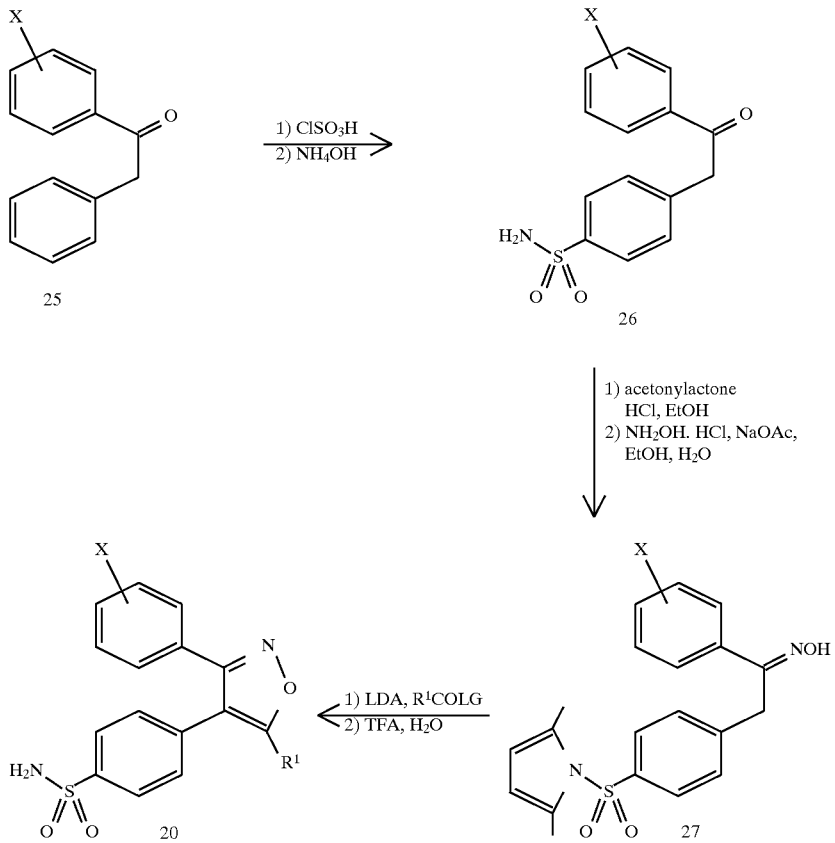

Scheme XIV illustrates the five step procedure for the preparation substituted isoxazole derivatives 20. In step one, ing dianion is quenched by a suitable acylating agent such as an anhydride, acid chloride, ester, acyl imidazole and the like to afford a hydrated isoxazole. In the last step, the hydrated isoxazole is dehydrated by an acid and the sulfonamide unmasked by treatment with warm aqueous trifluoroacetic acid (TFA) to form the final sulfonamide derivative 20.

Scheme XV

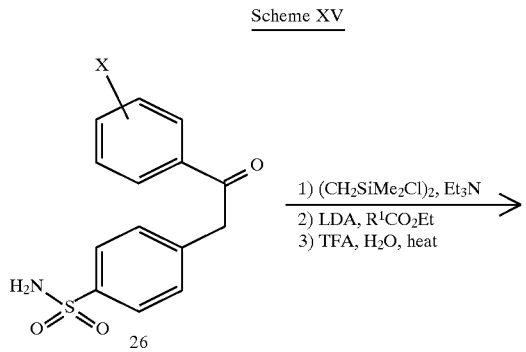

Synthetic Scheme XV shows the three-step, one-pot procedure for the preparation of substituted isoxazole derivatives 20. In the first step, the desoxybenzoin sulfonamide derivative 26 is protected as the cyclic disilylamine derivative by treatment with 1,2-bis-(chlorodimethylsilyl)ethane in the presence of triethylamine. In step two, the cyclic disilylamine protected sulfonamide is treated with excess lithium diisopropylamide followed by quenching of the resulting dianion with an ester to afford the corresponding hydrated isoxazole derivative. In the third step, the reaction mixture is treated with aqueous trifluoroacetic acid that effects dehydration of the hydrated isoxazole and unmasks the sulfonamide moiety to afford the desired isoxazole derivative 20.

Scheme XVI

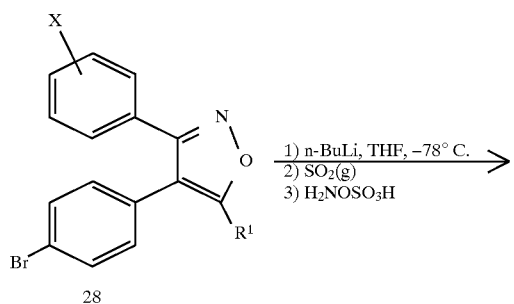

-continued
Scheme XVI

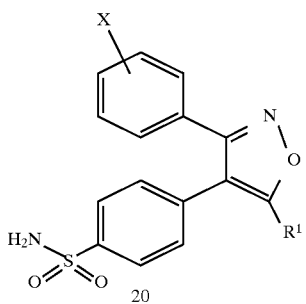

Synthetic Scheme XVI illustrates the three step procedure for the preparation of aromatic sulfonamides from aromatic bromides. In step one, the aromatic bromide is transmetallated to the corresponding lithium derivative which is immediately treated with gaseous sulfur dioxide to form an aromatic sulfinic acid. The sulfinic acid is converted directly to the sulfonamide by treatment with aqueous hydroxylamine-O-sulfonic acid and sodium acetate.

Similarly, starting with compounds having a (4-bromophenyl) substituent at isoxazole position three, one can prepare isoxazoles having a benzenesulfonamide at position three via this method.

Scheme XVII

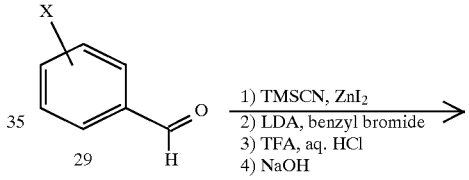

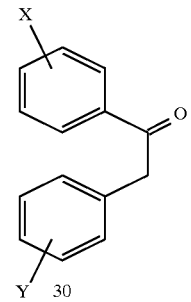

Synthetic Scheme XVII shows the four step one-pot procedure for the preparation of selected desoxybenzoin derivatives 30. In the first step a substituted benzaldehyde 29 is converted to the corresponding trimethylsilyl cyanohydrin by condensation with trimethylsilyl cyanide and a catalytic amount to zinc iodide. In step two the trimethylsilyl cyanohydrin is treated with lithium diisopropylamide to form the acyl anion equivalent which is alkylated by a substituted benzyl bromide to afford the trimethylsilyl cyanohydrin of desoxybenzoin 30. In steps three and four the trimethylsilyl cyanohydrin is first hydrolyzed with aqueous trifluoroacetic acid and hydrochloric acid to produce the corresponding cyanohydrin which is converted to 30 upon treatment with sodium hydroxide.

The following examples contain detailed descriptions of the methods of preparation of compounds of Formulas I–V. These detailed descriptions fall within the scope, and serve

33 to exemplify, the above described General Synthetic Procedures which form part of the invention. These detailed descriptions are presented for illustrative purposes only and are not intended as a restriction on the scope of the invention. All parts are by weight and temperatures are in degrees Centigrade unless otherwise indicated. All compounds showed NMR spectra consistent with their assigned structures.

EXAMPLE 1

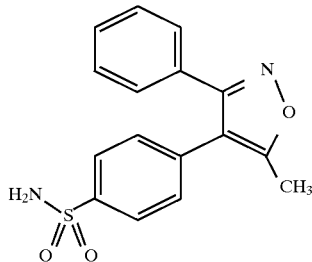

4-[5-Methyl-3-phenylisoxazol-4-yl] benzenesulfonamide

Step 1. Preparation of desoxybenzoin keto-oxime.

Hydroxylamine hydrochloride (9.21 g, 0.132 mol) and potassium hydroxide (7.43 g, 0.132 mol) were suspended in absolute ethanol (50 mL) and stirred at room temperature for thirty minutes. A solution of desoxybenzoin (20.0 g, 0.102 mol) in toluene (200 mL) was added in one portion, and the yellow suspension was held at reflux under a nitrogen blanket for 16 hours. The suspension was cooled to room temperature and poured into water (200 mL). The system was extracted with ethyl acetate (2×150 mL), and the combined organic solution was washed with brine (200 mL), dried over magnesium sulfate, and filtered. The solvents were evaporated under reduced pressure to yield a crude solid. The solid was recrystallized from hot ethanol/water, filtered and washed with water to yield, upon drying, desoxybenzoin keto-oxime as white crystals (17.7 g, 82%): mp 87°–90° C. Mass spectrum, MH+=212. High resolution mass spectrum Calc'd. for $C_{14}H_{13}NO$: 211.0997. Found: 211.0949.

Step 2. Preparation of 4-[5-methyl-3-phenylisoxazol-4-yl] benzenesulfonamide.

A solution of desoxybenzoin keto-oxime from Step 1 (6.00 g; 28.40 mmol) in anhydrous tetrahydrofuran (THF, 80 mL) was cooled to −20° C. To this cold solution, n-butyllithium (1.6N in hexanes, 44.4 mL) was added, via syringe, over 35 minutes, such that the reaction temperature remained at or below −10° C. The deep red solution was stirred at −10° C. for 1 hour, warmed to room temperature, then stirred at room temperature for an additional hour. Acetic anhydride (3.2 mL, 34.1 mmol) was added in one portion, and the resulting suspension was stirred without temperature control for 2 hours. Water (100 mL) was added, the solution was poured into 1N HCl (100 mL) and extracted with ethyl acetate (2×200 mL). The combined organic solution was washed with hydrochloric acid (1N HCl, 100 mL) and brine (100 mL), dried over magnesium sulfate and filtered. The resulting solution was evaporated under reduced pressure to yield a crude oil. The oil was applied to a column of silica gel and eluted with ethyl acetate/hexane (10–50% ethyl acetate) to yield, upon concentration of the appropriate fractions, 5.0 g of 3,4-diphenyl-4-hydrido-5-hydroxy-5-methylisoxazole. The solid was cooled to 0° C.,

34 then dissolved in cold chlorosulfonic acid (15 mL). The brown solution was stirred at 0° C. for 2 hours, then added dropwise to a stirred suspension of ice (200 mL) and dichloromethane (200 mL). The layers were separated, and the organic phase was added directly to a saturated ammonium hydroxide solution (100 mL) at 0° C. This biphasic solution was vigorously stirred at 0° C. for 2 hours, the layers were separated, and the aqueous phase was washed with dichloromethane (50 mL). The combined organic solution was dried over magnesium sulfate, filtered and evaporated under reduced pressure to approximately one-half of its original volume. Crystals formed. The stirred suspension was cooled to 0° C. and held for 30 minutes. The crystals were filtered, washed with cold dichloromethane and dried to yield 4-[5-methyl-3-phenylisoxazol-4-yl] benzenesulfonamide (2.7 g, 30%): mp 155°–57° C. $^1H$ NMR ($CD_3CN$/500 MHz) δ 7.86 (d, J=8.39 Hz, 2H), 7.45 (m, 1H), 7.39 (s, 4H), 7.37 (d, J=8.39 Hz, 2H), 5.70 (s, 2H), 2.46 (s, 3H). Mass Spectrum, MH+=315.

Proceeding in a like manner but replacing the anhydrides with other appropriately substituted anhydrides and esters, the following compounds were prepared:

1a) 4-[5-ethyl-3-phenylisoxazol-4-yl]benzenesulfonamide: mp 140°–141° C. $^1H$ NMR ($CDCl_3$) δ 7.93 (d, J=8.66, 2H), 7.28–7.42 (m, 7H), 4.81 (s, 2H), 2.83 (q, J=7.65 Hz, 2H), 1.34 (t, J=7.45, 3H). Mass spectrum $M^+H$ 329. Anal. Calc'd. for $C_{17}H_{16}N_2O_3S$: C, 62.18; H, 4.91; N, 8.53; S, 9.76. Found: C, 62.07; H, 4.88; N, 8.42; S, 9.61.

1b) 4-[5-propyl-3-phenylisoxazol-4-yl] benzenesulfonamide: mp 147°–148° C. $^1H$ NMR ($CDCl_3$) δ 7.92 (d, J=8.46, 2H), 7.28–7.44 (m, 7H), 4.83 (s, 2H), 2.77 (t, J=7.25, 2H), 1.71–1.85 (m, 2H), 0.98 ( t, J=7.45, 3H). Anal. Calc'd. for $C_{18}H_{18}N_2O_3S_1$: C, 63.14; H, 5.30; N, 8.18; S, 9.36. Found: C, 63.19; H, 5.32; N, 8.23; S, 9.44. Mass spectrum $M^+H$ 343.

1c) 4-[5-isopropyl-3-phenylisoxazol-4-yl] benzenesulfonamide: mp 166°–168° C. $^1H$ NMR ($CDCl_3$) δ 7.93 (d, J=8.46 Hz, 2H), 7.27–7.40 (m, 7H), 4.80 (s, 2H), 3.08–3.20 (m, 1H), 1.36 (d, J=6.58 Hz, 6 H). Mass spectrum $M^+H$ 343.

1d) 4-[5-butyl-3-phenylisoxazol-4-yl]benzenesulfonamide: mp 129°–131° C. $^1H$ NMR ($CDCl_3$) δ 7.93 (d, J=8.46 Hz, 2H), 7.30–7.40 (m, 7H), 4.81 (s, 2H), 2.79 (t, J=7.45, 2H), 1.67–1.79 (m, 2H), 1.30–1.42 (m, 2H), 0.91 (t, J=7.25, 3H). Anal. Calc'd. for $C_{19}H_{20}N_2O_3S_1$: C, 64.02; H, 5.66; N, 7.86; S, 8.99. Found: C, 63.22; H, 5.52; N, 7.51; S, 8.67.

1e) 4-[5-isobutyl-3-phenylisoxazol-4-yl] benzenesulfonamide: mp 159°–160° C. $^1H$ NMR ($CDCl_3$) δ 7.93 (d, J=8.46, 2H), 7.28–7.42 (m, 7H), 4.84 (s, 2H), 2.66 (d, J=7.25 Hz, 2H), 2.08–2.22 (m, 1H), 0.94 (d, J=6.65 Hz, 6H). High resolution mass spectrum Calc'd. for $C_{19}H_{20}N_2O_3S$: 221.0841. Found: 221.0827. Anal. Calc'd. for $C_{19}H_{20}N_2O_3S_1$: C, 64.02; H, 5.66; N, 7.86; S, 8.99. Found: C, 63.94; H, 5.65; N, 7.86; S, 8.90.

1f) 4-[5-cyclohexyl-3-phenylisoxazol-4-yl] benzenesulfonamide: mp 191°–193° C. $^1H$ NMR ($CDCl_3$) δ 7.94 (d, J=8.46 Hz, 2H), 7.27–7.41 (m, 7H), 4.85 (s, 2H), 2.62–2.85 (m, 1H), 1.67–1.95 (m, 7H), 1.22–1.38 (m, 3H). Mass spectrum $M^+H$ 383. High resolution mass spectrum Calc'd. for $C_{21}H_{22}N_2O_3S$: 383.1429. Found: 383.1452.

1g) 4-[5-neopentyl-3-phenylisoxazol-4-yl] benzenesulfonamide: $^1H$ NMR ($CDCl_3$) δ 7.94 (d, J=8.46, 2H), 7.26–7.39 (m, 7H), 4.82 (s, 2H), 2.71 (s, 2H), 0.94 (s, 9H). Mass spectrum $M^+H$ 371.

1h) 4-[5-cyclohexylmethyl-3-phenylisoxazol-4-yl] benzenesulfonamide: mp 151°–153° C. $^1H$ NMR ($CDCl_3$)

δ 7.93 (d, J=8.46, 2H), 7.29–7.43 (m, 7H), 4.82 (s, 2H), 2.67 (d, J=7.05 Hz, 2H), 1.60–1.92 (m, 5H), 0.85–1.30 (m, 6H). Mass spectrum M+H 397.

1i) 4-[5-(4-chlorophenyl)methyl-3-phenylisoxazol-4-yl]benzenesulfonamide: mp 107°–108° C. $^1$H NMR (CDCl$_3$ and CD$_3$OD ) δ 7.91 (d, J=8.46, 2H), 7.26–7.42 (m, 9H), 7.14 (d, J=8.46 Hz, 2H), 4.85 (s, 2H), 4.10 (s, 2H). Mass spectrum M+H=425. High resolution mass spectrum Calc'd. for C$_{22}$H$_{17}$ClN$_2$O$_3$S: 425.0727. Found: 425.0736.

1j) 4-[5-difluoromethyl-3-phenylisoxazol-4-yl]benzenesulfonamide: mp 172°–175° C. $^1$H NMR (CDCl$_3$) δ 7.97 (d, J=8.46, 2H), 7.30–7.50 (m, 7H), 6.72 (t, J=52.57 Hz, 1H), 4.87 (s, 2H). $^{19}$F NMR (CHCl$_3$) –116.45 (d, J=53.02 Hz). Mass spectrum M+H 351.

1k) 4-[5-chloromethyl-3-phenylisoxazol-4-yl]benzenesulfonamide: mp 131°–133° C. $^1$H NMR (CDCl$_3$) δ 7.98 (d, J=8.46, 2H), 7.34–7.46 (m, 7H), 4.84 (s, 2H), 4.61 (s, 2H). Mass spectrum M+H 349. High resolution mass spectrum for C$_{16}$H$_{13}$ClN$_2$O$_3$S: 348.0335. Found: 348.0316.

1l) 4-[5-methyl-3-phenylisoxazol-4-yl]benzenesulfonic acid: mp 260°–269° C. $^1$H NMR (CD$_3$OD) δ 9.03 (s, >1H exch), 8.42 (d, J=8.06 Hz, 2H), 8.12–8.28 (m, 5H), 7.97 (d, J=8.26 Hz, 2H). Mass spectrum M+H 316.

1m) 4-[5-propyl-3-phenylisoxazol-4-yl]benzenesulfonic acid: $^1$H NMR (CDCl$_3$ and CD$_3$OD ) δ 7.95–7.78 (m, 2H), 7.10–7.40 (m, 7H), 2.65–2.78 (m, 2H), 1.65–1.80 (m, 2H), 0.88–0.99 (m, 3H). Mass spectrum M+H 344.

1n) 4-[5-methoxymethyl-3-phenylisoxazol-4-yl]benzenesulfonamide: mp 82°–118° C. $^1$H NMR (CDCl$_3$) δ 7.93 (d, J=8.66 Hz, 2H), 7.31–7.45 (m, 7H), 4.81 (s, 2H), 4.51 (s, 2H), 3.48 (s, 3H). Mass spectrum M+H 345. High resolution mass spectrum Calc'd. for C$_{17}$H$_{16}$N$_2$O$_4$S: 344.0831. Found: 344.0807.

1o) 4-[5-(3-hydroxypropyl)-3-phenylisoxazol-4-yl]benzenesulfonamide: mp 88°–142° C. $^1$H NMR (CDCl$_3$ and CD$_3$OD ) δ 7.90 (d, J=8.66 Hz, 2H), 7.26–7.42 (m, 7H), 3.66 (t, J=6.04 Hz, 2H), 2.91 ( t, J=7.45 Hz, 2H), 1.93–2.02 (m, 2H). Mass spectrum M+H 349. High resolution mass spectrum Calc'd. for C$_{18}$H$_{18}$N$_2$O$_4$S: 358.0987. Found: 358.0958.

EXAMPLE 2

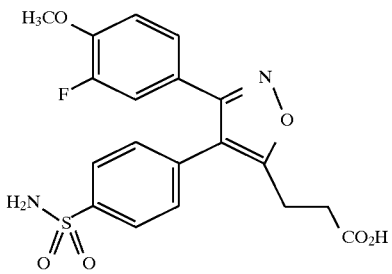

[4-[4-(Aminosulfonyl)phenyl]-3-(3-fluoro-4-methoxyphenyl)isoxazol-5-yl]propanoic acid Step 1: Preparation of 1-(3-fluoro-4-methoxyphenyl)-2-phenyl-ethan-1-one.

A suspension of aluminum chloride (9.4 g, 70.5 mmol) in a solution of 2-fluoroanisole (6.6 mL, 58.8 mmol) and anhydrous chloroform (200 mL) was cooled to 0° C. under a blanket of dry nitrogen. A solution of phenylacetyl chloride (8.6 mL, 64.7 mmol) in anhydrous chloroform (50 mL) was added to the vigorously stirred suspension over 20 minutes keeping the reaction temperature <5° C. The yellowish solution was stirred at 0° C. for 1 hour, poured into ice (200 mL) and stirred without temperature control for 16 hours. The layers were separated, and the aqueous layer was extracted with dichloromethane (2×100 mL). The combined organic solution was dried over magnesium sulfate, filtered, and the solvent was evaporated under reduced pressure. The resulting solid was recrystallized from boiling hexane to yield, upon filtration and drying, 1-(3-fluoro-4-methoxyphenyl)-2-phenyl-ethan-1-one (12.9 g, 90%) as white crystals: $^1$H NMR (CDCl$_3$/300 MHz) δ 7.82–7.72 (m, 2H), 7.35–7.24 (m, 5H), 6.98 (dd, J=8.46, 8.26 Hz, 1H), 4.22 (s, 2H), 3.94 (s, 3H). $^{19}$F NMR (CDCl$_3$/282.2 MHz) –134.875 (m).

Step 2: Preparation of 1-(3-fluoro-4-methoxyphenyl)-2-phenyl-ethan-1-one oxime.

Hydroxylamine hydrochloride (3.7 g, 53.2 mmol) and potassium hydroxide (2.98 g, 53.2 mmol) were suspended in absolute ethanol (25 mL) and stirred for 30 minutes. To this, a suspension of 1-(3-fluoro-4-methoxyphenyl)-2-phenyl-ethan-1-one from Step 1 (10.0 g, 40.9 mmol) in toluene (150 mL) was added in one portion. The yellow suspension was warmed to reflux for 16 hours, then the suspension was cooled to room temperature. Water (100 mL) was added, and the resulting solution was extracted with ethyl acetate (2×100 mL). The combined organic solution was washed with brine (100 mL), dried over magnesium sulfate and filtered. The resulting solution was evaporated under reduced pressure to yield a crude residue. The residue was crystallized from boiling ethanol/water to yield, upon filtration and drying 1-(3-fluoro-4-methoxyphenyl)-2 phenyl-ethan-1-one oxime as ivory-colored crystals (10.0 g, 94%): $^1$H NMR (CDCl$_3$/300 MHz) δ 7.42 (dd, J=12.69, 2.01, 1H), 7.36–7.19 (m, 6H), 6.89 (dd, J=8.66, 8.46 HZ, 1H), 4.16 (s, 2H), 3.88 (s, 3H). $^{19}$F NMR (CDCl$_3$/282.2 MHz): 135.517 (m).

Step 3: [3-(3-fluoro-4-methoxyphenyl)-4-phenylisoxazol-5-yl]propanoic acid:

1-(3-Fluoro-4-methoxyphenyl)-2-phenyl-ethan-1-one oxime from Step 2 (2.00 g, 7.71 mmol) and anhydrous THF (80 mL) under a nitrogen blanket was cooled to –20° C., and n-butyllithium (1.6N, 12.0 mL) was added, via syringe, over 20 minutes, keeping the reaction temperature <–10° C. The deep red suspension was stirred at –20° C. for 1 hour, warmed to room temperature, and stirred at room temperature for 1 hour. Succinic anhydride (926 mg, 9.26 mmol) was added in one portion, and the yellow reaction was stirred for 16 hours without temperature control. Sulfuric acid (conc., 2.1 mL) was added, and the reaction was warmed to reflux. After 2 hours, the brown mixture was cooled to room temperature, diluted with water (100 mL), and extracted with ether (2×100 mL). The ethereal solution was extracted with dilute sodium hydroxide (2×100 mL), and the combined basic extracts were acidified to pH <2 with hydrochloric acid (conc.). The acidic aqueous phase was extracted with ether (2×100 mL). This ethereal solution was evaporated under reduced pressure to a residue. The residue was applied to a column of silica gel (200 cc) and eluted (10% methanol in dichloromethane) to yield, upon concentration of the appropriate fractions, a crude solid. The solid was recrystallized from hot ethanol and 0.1N HCl to yield, upon filtration and drying, [3-(3-fluoro-4-methoxyphenyl)-4-phenylisoxazol-5-yl]propanoic acid as ivory colored crystals (367 mg, 14%): mp 129°–131° C. (dec). Mass Spectrum: MH+=342. $^1$H NMR (CDCl$_3$/300 MHz) δ 7.39 (m, 3H), 7.22–7.12 (m, 4H), 6.87 (t, J=8.46 Hz, 1H), 3.88 (s, 3H), 3.09 (t, J=8.05 Hz, 2H), 2.80 (t, J=8.05 Hz, 2H). $^{19}$F NMR(CDCl$_3$/282.2 MHz) : –135.466 (m).

Step 4: Preparation of F4-[4-(aminosulfonyl)phenyl]-3-(3-fluoro-4-methoxyphenyl)isoxazol-5-yl]-propanoic acid:

[3-(3-Fluoro-4-methoxyphenyl)-4 phenylisoxazol-5-yl]propanoic acid from Step 3 (250 mg, 0.73 mmol) and sulfuric acid (1 mL) were dissolved in absolute ethanol (10 mL). The colorless solution was warmed to reflux and held for 16 hours. The solution was cooled to room temperature and diluted with water (20 mL). The aqueous solution was extracted with ether (2×50 mL), and the combined ethereal solution was washed with dilute sodium hydroxide (30 mL). The organic solution was dried over magnesium sulfate, filtered and evaporated under reduced pressure to yield an oil. The oil was cooled to 0° C., and chlorosulfonic acid (0° C., 12 mL) was added. The reaction was kept at 0° C. under a nitrogen blanket for 2 hours, and carefully poured into ice. The ice was extracted with dichloromethane (2×20 mL) and the organic extract was added directly to a stirred, 0° C. saturated $NH_4OH$ solution (40 mL). The biphasic reaction was stirred at 0° C. for 3 hours. The layers were separated, and the aqueous layer was extracted with dichloromethane (30 mL). The combined organic solution was dried over magnesium sulfate, filtered and evaporated under reduced pressure to yield a crude foam. The foam was dissolved in dioxane (30 mL), aqueous sodium hydroxide (10%, 0.9 mL) was added and the solution was heated to reflux for 1 hour. The solution was cooled to room temperature and diluted with water (20 mL). The aqueous solution was extracted with ether (2×30 mL) and the combined ethereal solution was extracted with dilute sodium hydroxide (5%, 2×30 mL). The aqueous phases were combined and acidified with hydrochloric acid (conc.) to pH <2. The acidic aqueous phase was extracted with ether (2×30 mL). The final ether solution was dried over magnesium sulfate, filtered and evaporated under reduced pressure to yield a crude solid. The solid was recrystallized from ethanol/0.1N HCl to yield, upon filtration and drying, [4-[4-(aminosulfonyl)phenyl]-3-(3-fluoro-4-methoxyphenyl)isoxazol-5-yl]propanoic acid as cream-colored crystals (182 mg, 59%): mp=159°–161° C. (dec) . $^1$H NMR ($CDCl_3$/300 MHz) δ 7.91 (d, J=8.66 Hz, 2H), 7.34 (d, J=8,66 Hz, 2H), 7.14 (dd, J=11.88, 2.01 Hz), 7.02 (d, J=8.46 Hz), 6.87 (t, J=8.46 Hz, 1H), 3.86 (s, 3H), 3.05 (t, J=7.45 Hz, 2H), 2.74 (t, J=7.45 Hz, 2H). $^{19}$F NMR ($CDCl_3$/282.2 MHz): –135.020 (m).

EXAMPLE 3

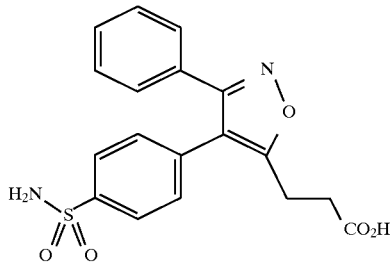

[4-[4-(Aminosulfonyl)phenyl]-3-phenylisoxazol-5-yl]propanoic acid

Step 1. Preparation of [3,4-diphenylisoxazol-5-yl]propanoic acid.

[3,4-Diphenylisoxazol-5-yl]propanoic acid was prepared in 45% yield from desoxybenzoin oxime (Example 1, Step 1) and succinic anhydride according to the procedure outlined in Example 2, Step 3: mp 123°–125° C. (dec). Anal. Calc'd for $C_{18}H_{15}NO_3$: C, 73.71; H, 5.15; N, 4.78. Found: C, 73.78; H, 5.18; N, 4.72.

Step 2. Preparation of ethyl [4-[4-(aminosulfonyl)phenyl]-3-phenylisoxazol-5-yl]propanoate:

A solution of [3,4-diphenylisoxazol-5-yl]propanoic acid was treated with ethanol in the presence of a catalytic amount of sulfuric acid to prepare the corresponding ethyl ester which was immediately treated with chlorosulfonic acid followed by ammonia according to the procedure from Example 2, Step 4. The crude sulfonamide was purified by flash chromatography eluting with ethyl acetate/hexane (10–50% ethyl acetate) to yield, upon concentration of the appropriate fractions, ethyl [4-[4-(aminosulfonyl)phenyl]-3-phenylisoxazol-5-yl]propanoate as a glassy solid (248 mg, 60%): Mass spectrum: MH+=401. $^1$H NMR ($CDCl_3$/300 MHz) δ 7.93 (d, J=8.46 Hz, 2H) 7.41–7.30 (m, 7H), 4.84 (s, 2H), 4.14 (q, J=7.04 Hz, 2H), 3.12 (t, J=7.45 Hz, 2H), 2.81 (t, J=7.45 Hz, 2H), 1.25 (t, J=7.04 Hz, 3H). This material was used directly in the next step without further purification.

Step 3. Preparation of [4-[4-(aminosulfonyl)phenyl]-3-phenylisoxazol-5-yl]propanoic acid.

Ethyl [4-[4-(aminosulfonyl)phenyl]-3-phenylisoxazol-5-yl]propanoate from Step 2 (198 mg, 0.495 mmol) and aqueous sodium hydroxide (10%, 0.30 mL) were dissolved in dioxane (15 mL). The solution was heated to reflux and held for 16 hours. Upon cooling to room temperature, water (20 mL) was added, and the solution was extracted with ether (2×30 mL). The combined ethereal solution was extracted with dilute sodium hydroxide (5%, 2×30 mL). All of the aqueous phases were combined and acidified with hydrochloric acid (conc.) to pH <2. The acidic aqueous phase was extracted with ether (2×30 mL). The final ether solution was dried over magnesium sulfate, filtered and evaporated under reduced pressure to yield a crude solid. Trituration with dichloromethane yielded crystals. The suspension was cooled to 0° C., filtered, washed with hexane and dried to yield [4-[4-(aminosulfonyl)phenyl]-3-phenylisoxazol-5-yl]propanoic acid as a white crystalline solid (135 mg, 73%): mp 207° C. Mass spectrum: MH+= 373. Anal. Calc'd. for $C_{18}H_{16}N_2O_5S$: C, 58.06; H, 4.33; N, 7.52; S, 8.61. Found: C, 57.87; H, 4.35; N, 7.49; S, 8.54.

EXAMPLE 4

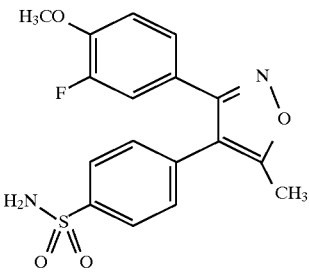

4-[3-(3-Fluoro-4-methoxyphenyl)-5-methylisoxazol-4-yl]benzenesulfonamide

Step 1: Preparation of 3-[3-fluoro-4-methoxyphenyl]-5-methyl-4-phenylisoxazole.

1-(3-Fluoro-4-methoxyphenyl)-2-phenyl-ethan-1-one oxime (from Example 2, Step 2) (2.50 g, 9.64 mmol) and anhydrous THF (100 mL) under a nitrogen blanket, was cooled to –20° C., and n-butyllithium (1.6N, 15.0 mL) was added, via syringe, over 20 minutes, keeping the reaction temperature <–10° C. The deep red suspension was stirred at –20° C. for 1 hour, warmed to room temperature, and stirred at room temperature for 1 hour. Acetic anhydride (1.1 mL, 11.6 mmol) was added in one portion, and the yellow reaction was stirred for 2 hours without temperature control. The reaction was poured into aqueous hydrochloric acid (1N, 100 mL) and extracted with ethyl acetate (2×100 mL). The combined organic solution was washed once each with aqueous hydrochloric acid (1N, 100 mL) and brine (100 mL), dried over magnesium sulfate, filtered and evaporated under reduced pressure to yield a crude oil. The oil was applied to a column of silica gel (250 mL) and eluted with ethyl acetate/hexane (10–40% ethyl acetate) to yield, upon concentration of the appropriate fractions 3-(3-fluoro-4-methoxyphenyl)- 4-hydrido-5-hydroxy-4-phenyl-5-methylisoxazole (986 mg). This intermediate was dissolved in tetrahydrofuran (40 mL). Sulfuric acid (conc., 0.9 mL) was added, and the reaction was warmed to reflux. After one hour, the solution was cooled to room temperature, diluted with water (50 mL), and extracted with ethyl acetate (2×50 mL). The combined organic solution was washed with aqueous hydrochloric acid (1N, 50 mL), saturated aqueous sodium bicarbonate (2×50 mL) and brine (50 mL), dried over magnesium sulfate, filtered and evaporated under reduced pressure to yield a crude, dark oil. Washing the oil with 50% dichloromethane in hexane dissolved the compound but did not dissolve the dark impurities. The resulting solution was evaporated under reduced pressure to yield 3-(3-fluoro-4-methoxyphenyl)-5-methyl-4-phenylisoxazole (797 mg, 29%) as a foam. Mass Spectrum: MH+=284. Anal. Calc'd. for $C_{17}H_{14}NO_2F$: C, 72.07; H, 4.98; N, 4.94. Found: C, 72.13; H, 4.98; N, 4.92.

Step 2: Preparation of [3-(3-fluoro-4-methoxyphenyl)-5-methylisoxazol-4-yl]benzenesulfonamide:

Chlorosulfonic acid (8 mL) was cooled to 0° C. 3-(3-Fluoro-4-methoxyphenyl)-5-methyl-4-phenylisoxazole from Step 1 (375 mg, 1.32 mmol) was added in one portion. The brown solution was stirred at 0° C. under a nitrogen blanket for 2 hours, then added dropwise to ice (50 mL). The ice was extracted with dichloromethane (2×30 mL), and the organic extracts were added directly to a 0° C. saturated aqueous NH$_4$OH solution. The biphasic reaction was vigorously stirred at 0° C. for 2 hours, then the layers were separated. The aqueous solution was extracted with dichloromethane, the combined organic solutions were dried over magnesium sulfate, filtered and evaporated under reduced pressure to yield a crude solid. The solid was recrystallized from ethanol and water to yield, upon filtration and drying, 4-[3-(3-fluoro-4-methoxyphenyl)-5-methylisoxazol-4-yl]benzenesulfonamide as ivory colored crystals (275 mg, 55%): mp 175° C. (dec). Mass Spectrum: MH+=363. Anal. Calc'd. for $C_{17}H15N_2O_4FS$: C, 56.47; H, 4.17; N, 7.73; S, 8.85. Found: C, 56.47; H, 4.19; N, 7.66; S, 8.81.

Proceeding in a like manner but replacing desoxybenzoin with other appropriately substituted ketones, the following compounds were prepared:

4a) 4-[3-(4-chlorophenyl)-5-methyl-isoxazol-4-yl]benzenesulfonamide: mp 162°–164° C. $^1$H NMR (CDCl$_3$) 7.97 (d, 2H, J=8.46 Hz), 7.33–7.26 (m, 7H), 2.48 (s, 3H). Elemental analysis Calc'd. for $C_{16}H_{13}N_2O_3SCl$: C, 55.1; H, 3.76; N, 8.03. Found: C, 55.12; H, 3.78; N, 8.03.

4b) 4-[3-(4-fluorophenyl)-5-methyl-isoxazol-4-yl]benzenesulfonamide: mp 152°–156° C. $^1$H NMR (CDCl$_3$) 2.48 (s, 3H), 4.84 (bs, 2H), 7.04 (t, 1H, J=8.6 Hz), 7.33–7.40 (m, 4H), 7.94 (d, 2H, J=8.4). High resolution mass spectrum Calc'd for $C_{16}H_{13}FN_2O_3S$: 333.0709. Found: 333.0704.

4c) 4-[3-(3-fluoro-4-methylphenyl)-5-methyl-isoxazol-4-yl]benzenesulfonamide: mp 146°–150° C. $^1$H NMR (CDCl$_3$) 2.24 (s, 3H), (2.48 (s, 3H), 4.97 (bs, 2H), 6.93 (t, 1H, J=9.1 Hz), 7.04 (m, 1H), 7.26–7.37 (m, 3H), 7.94 (d, 2H, J=8.3). High resolution mass spectrum Calc'd for $C_{17}H_{15}FN_2O_3S$: 347.0866. Found: 347.0865. Anal. Calc'd. for $C_{17}H_{15}FN_2O_3S$: C, 58.95; H, 4.37; N, 8.03. Found: C, 58.09; H, 4.47; N, 8.03.

4d) 4-[3-(3-chloro-4-methylphenyl)-5-methyl-isoxazol-4-yl]benzenesulfonamide: mp 120°–122° C. $^1$H NMR (CD$_3$OD) 2.30 (s, 3H), 2.48 (s, 3H) 4.84 (bs, 2H), 7.11 (m, 1H), 7.33–7.40 (m, 4H), 7.92 (d, 2H, J=8.4). High resolution mass spectrum Calc'd for $C_{17}H_{15}FN_2O_3S$: 363.0570. Found: 363.0584. Elemental analysis. Calc'd for $C_{17}H_{15}ClN_2O_3S$: C, 56.28; H, 4.17; N, 7.72. Found: C, 56.02; H, 4.38; N, 7.54.

4e) 4-[5-methyl-3-(3-pyridyl)isoxazol-4-yl]benzenesulfonamide: mp 110°–115° C. (dec). $^1$H NMR (CDCl$_3$) 8.57 (br s, 1H), 8.47 (s, 1H), 7.88, 7.24 (AB quartet, 4H), 7.51–7.41 (m, 2H), 2.43 (s, 3H). Mass spectrum M+H 316.

4f) 4-[5-methyl-3-(4-pyridyl)-isoxazol-4-yl]benzenesulfonamide: mp 108°–110° C. (dec). $^1$H NMR (CDCl$_3$) 8.51 (d, 2H, J=6.0 Hz), 7.9 (d, 2H, J=8.46 Hz), 7.30–7.26 (m, 4H), 6.11 (s, 2H), 2.44 (s, 3H). Mass spectrum M+H 316. Anal. Calc'd. for $C_{15}H_{13}N_3O_3S.H_2O$: C, 54.05; H, 4.54; N, 12.62. Found: C, 53.65; H, 4.08; N, 12.42.

4g) 4-[3-(3-fluorophenyl)-5-methyl-isoxazol-4-yl]benzenesulfonamide: mp 130°–136° C. (dec). $^1$H NMR (CDCl$_3$) 7.95 (d, 2H, J=8.5 Hz), 7.33 (d, 2H), 7.33–7.11 (m, 4H), 2.50 (s, 3H). Mass spectrum M+H 333. Anal. Calc'd. for $C_{16}H_{13}N_2O_3SF$: C, 57.82; H, 3.94; N, 8.43. Found: C, 57.42; H, 4.57; N, 7.50.

EXAMPLE 5

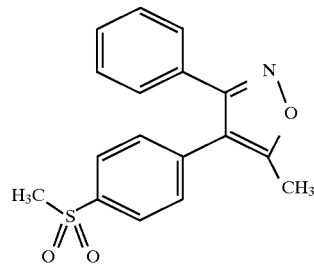

5-Methyl-4-[4-(methylsulfonyl)phenyl]-3-phenylisoxazole

Step 1. Preparation of 1-phenyl-2-[4-(methylthio)phenyl]-ethan-1-one.

This ketone was prepared from the Friedel Crafts acylation of benzene with 4-methylthiophenylacetyl chloride in the presence of aluminum chloride: $^1$H NMR (CDCl$_3$/300 MHz) δ 7.92 (d, J=8.66 Hz, 2H), 7.32–7.22 (m, 7H), 4.24 (s, 2H), 2.51 (s, 3H).

Step 2. Preparation of 1-phenyl-2-4-(methylthio)phenyl]-ethan-1-one oxime.

This oxime was prepared from 1-phenyl-2-[4-(methylthio)phenyl]-ethan-1-one (Step 1) and hydroxylamine in 80% yield by the method outlined in Example 1, Step 1: $^1$H NMR (CDCl$_3$/300 MHz) δ 7.54 (d, J=8.66 Hz, 2H), 7.32–7.17 (m, 7H), 4.19 (s, 2H), 2.36 (s, 3H).

Step 3. Preparation of 5-methyl-4-[4-(methylthio)phenyl]-3-phenylisoxazole:

5-Methyl-4-[4-(methylthio)phenyl]-3-phenylisoxazole was prepared in 48% yield from the reaction of 1-phenyl- 2-[4-(methylthio)phenyl]-ethan-1-one oxime (Step 2) and acetic anhydride according to the procedure outlined in Example 4, Step 1: Mass Spectrum: MH+=282. High resolution mass spectrum Calc'd. for $C_{17}H_{15}NOS$: 281.0874. Found: 281.0875. Anal. Calc'd.: C, 72.57; H, 5.37; N. 4.98; S, 11.39. Found: C, 72.56; H, 5.41; N, 5.00; S, 11.34.

Step 4. Preparation of 5-methyl-4-[4-(methylsulfonyl) phenyl]-3-phenylisoxazole:

5-Methyl-4-[4-(methylthio)phenyl]-3-phenylisoxazole from Step 3 (100 mg, 0.355 mmol) was dissolved in methanol (20 mL). Oxone® (0.765 g, 1.24 mmol) and water (2 mL) were added, and the suspension was stirred at room temperature for 2 hours. Water was added (30 mL) and the resulting suspension was cooled to 0° C. and held for 30 minutes whereupon the product crystallized. The product was isolated by filtration, washed with water and dried to yield 5-methyl-4-[4-(methylsulfonyl)phenyl]-3-phenylisoxazole (32 mg, 29%): mp 54°–56° C. Mass Spectrum: MLi+=320. High resolution mass spectrum Calc'd for $C_{17}H_{15}NO_3S$: 313.077. Found: 313.078.

EXAMPLE 6

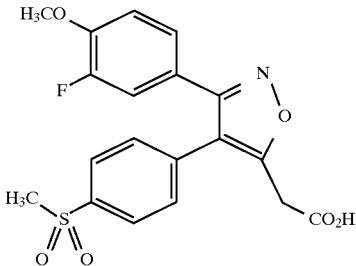

[3-[3-Fluoro-4-methoxyphenyl]-4-[4-(methylsulfonyl)phenyl]isoxazol-5-yl]acetic acid Step 1. Preparation of 1-(3-fluoro-4-methoxyphenyl)-2-[4-(methylthio)phenyl]-ethan-1-one.

1-(3-Fluoro-4-methoxyphenyl)-2-[4-(methylthio)-phenyl]-ethan-1-one was prepared by Friedel Crafts acylation of 2-fluoroanisole with 4-(methylthio)phenylacetyl chloride in the presence of aluminum chloride: $^1$H NMR (CDCl$_3$/300 MHz) δ 7.80–7.70 (m, 2H), 7.24–7.15 (m, 4H), 6.98 (t, J=8.26 Hz), 4.17 (s, 2H), 3.95 (s, 3H), 2.46 (s, 3H). $^{19}$F NMR (CDCl$_3$/282.2 MHz): –134.804 (m).

Step 2. Preparation of 1-(3-fluoro-4-methoxyphenyl)-2-[4-(methylthio)phenyl]-ethan-1-one oxime.

1-(3-Fluoro-4-methoxyphenyl)-2-[4-(methylthio)phenyl]-ethan-1-one oxime was prepared in 91% yield by treatment of 1-(3-fluoro-4-methoxyphenyl)-2-[4-(methylthio)phenyl]-ethan-1-one from Step 1 with hydroxylamine: $^1$H NMR (CDCl$_3$/300 MHz) δ 7.40 (dd, J=12.69, 2.22 Hz, 1H), 7.30 (d, J=8.66 Hz, 1H), 7.18–7.12 (m, 4H), 6.88 (dd, J=8.66, 8.46 Hz, 1H), 4.10 (s, 2H), 3.87 (s, 3H), 2.43 (s, 3H).

Step 3. Preparation of 3-(3-fluoro-4-methoxyphenyl)-5-methyl-4-[4-(methylthio)phenyl]isoxazole:

3-(3-Fluoro-4-methoxyphenyl)-5-methyl-4-[4-(methylthio)phenyl]isoxazole was prepared in 30% yield from 1-(3-fluoro-4-methoxyphenyl)-2-[4-(methylthio)phenyl]-ethan-1-one oxime from Step 2 and acetic anhydride by the procedure described in Example 4, Step 1 and used directly in the next step.

Step 4. Preparation of [3-[3-fluoro-4-methoxyphenyl]-4-[4-(methylsulfonyl)phenyl]isoxazol-5-yl]acetic acid.

Anhydrous THF (35 mL) was added to 3-(3-fluoro-4-methoxyphenyl)-5-methyl-4-[4-(methylthio)phenyl] isoxazole (326 mg, 0.99 mmol) and the solution was cooled to –78° C. under a dry nitrogen blanket. To this solution, n-butyllithium (1.6N in hexane; 0.74 mL) was added, via syringe over approximately 3 minutes, keeping the reaction temperature <–75° C. The deep red suspension was stirred at –78° C. for 1 hour. Simultaneously, anhydrous tetrahydrofuran (80 mL) was cooled to –78° C. and saturated with carbon dioxide gas. The red reaction solution was quenched into the carbon dioxide-saturated THF. The yellow reaction was warmed to room temperature over 2 hours, then diluted with water (50 mL) and ether (80 mL). The solution was extracted with aqueous sodium hydroxide (5%, 2×50 mL), and the combined aqueous solution was acidified to pH <2 with aqueous hydrochloric acid (conc.). The acidic solution was extracted with dichloromethane (2×50 mL). The combined organic solution was dried over magnesium sulfate, filtered and evaporated under reduced pressure to a crude solid. The solid was dissolved in methanol (20 mL) and Oxone® (2.13 g, 3.47 mmol) and water (3 mL) were added. The suspension was stirred at room temperature for 2 hours, warmed to reflux and held for an additional 2 hours. Upon cooling to room temperature, water (35 mL) and aqueous hydrochloric acid (6N, 1 mL) were added. The resulting suspension was cooled to 0° C., held for 30 minutes, filtered and washed with cold water to yield, upon drying, [3-(3-fluoro-4-methoxyphenyl)-4-[4-(methylsulfonyl)phenyl] isoxazol-5-yl]acetic acid as white crystals (173 mg, 43%): mp 89° C. Mass spectrum: MH+=406. Anal. Calc'd. for $C_{19}H_{16}NO_6FS$: C, 56.29; H, 3.98; N, 3.46; S, 7.91. Found: C, 56.22; H, 4.00; N, 3.44; S, 7.85.

EXAMPLE 7

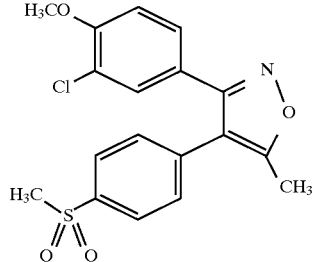

3-(3-Chloro-4-methoxyphenyl)-5-methyl-4-[4-methylsulfonylphenyl]isoxazole

Steo 1. Preparation of 3-chloro-4-methoxyacetophenone.

Anhydrous aluminum chloride (281 g, 2.104 mol) and 1 L of ethanol-free chloroform were maintained at 0° C. with an ice bath while a solution of acetyl chloride (162 g, 2.28 mol) in 300 mL of chloroform was added over 25 minutes. To this solution was added 2-chloroanisole (250 g, 1.75 mol) in 250 mL of chloroform over 1 hour. The solution was stirred at room temperature for 16 hours and was poured into a mixture of ice and water. The phases were separated and the aqueous phase was extracted with dichloromethane and combined with the original organic phase. The combined organics were dried over anhydrous MgSO$_4$, filtered and concentrated in vacuo to afford a solid which was crystallized from dichloromethane/hexane to give 3-chloro-4-methoxyacetophenone (246 g, 76%) which was used directly in the next step without further purification.

Step 2. Preparation of 3-chloro-4-methoxyphenylacetic acid.

A mixture of 3-chloro-4-methoxyacetophenone from Step 1 (10.0 g. 54.2 mmol) and boron trifluoride etherate complex (26.6 mL, 0.216 mol) in 20 mL of methanol was added to a suspension of lead tetraacetate (24 g, 54.2 mmol) in 50 mL of toluene. The mixture was stirred at room temperature for 16 hours, treated with 50 mL of water. The phases were separated and the aqueous phase was washed with toluene. The toluene solution was dried over anhydrous MgSO$_4$, filtered and concentrated in vacuo to provide an oil which was dissolved in 40 mL of dioxane and treated with excess 2.5N sodium hydroxide solution. The solution was stirred at room temperature for 2 hours and concentrated in vacuo. The residue was extracted with dichloromethane and the aqueous phase was acidified with concentrated HCl. The acidic solution was extracted with dichloromethane. The dichloromethane extract was dried over anhydrous MgSO$_4$, filtered and concentrated in vacuo to afford pure 3-chloro-4-methoxyphenylacetic acid (9.11 g, 84%) which was used directly in the next step.

Step 3. Preparation of 2-(3-chloro-4-methoxyphenyl)-3-[4-(methylthio)phenyl]-2-propenoic acid.

A mixture of 3-chloro-4 methoxyphenylacetic acid from Step 2 (4.50 g, 22.4 mmol), 4-methylthiobenzaldehyde (2.70 g, 20.4 mmol) and triethylamine (2.8 mL, 20.4 mmol) was dissolved in 40 mL of acetic anhydride and heated to reflux for 3 hours. The solution was cooled to 110° C., treated cautiously with 70 mL of water and cooled to room temperature, whereupon crystals of 2-(3-chloro-4-methoxyphenyl)-3-[4-(methylthio)phenyl]-2-propenoic acid formed. The crystals were isolated by filtration and air dried to afford 5.68 g (75%) of pure acid which was used directly in the next step.

Step 4. Preparation of 1-(3-chloro-4-methoxyphenyl)-2-[4-(methylthio)phenyl]-ethan-1-one.

A solution of 1-(3-chloro-4 methoxyphenyl)-3-[4-(methylthio)phenyl]propenoic acid from Step 3 (5.00 g, 14.9 mmol) and triethylamine (2.20 g, 15.7 mmol) in 50 mL of toluene was cooled to 0° C. and treated with diphenylphosphoryl azide (3.20 g, 14.9 mmol) via syringe. The solution was maintained at 0° C. for 30 minutes and diluted with water. The phases were separated and the aqueous phase was washed with ether. The original toluene solution was combined with the ethereal extract, dried over anhydrous MgSO$_4$, filtered and concentrated to remove the ether. The remaining toluene solution was heated to 115° C. for 90 minutes, treated with tert-butyl alcohol (1.50 g, 16.4 mmol) and maintained at this temperature for an additional 30 minutes. The solution was cooled to 90° C., treated with 1.4 mL of concentrated HCl and cooled to room temperature. The solution was washed with saturated aqueous NaHCO$_3$, and with brine and dried over anhydrous MgSO$_4$, filtered and concentrated to give 1-(3-chloro-4-methoxyphenyl)-2-[4-(methylthio)phenyl]-ethan-1-one as a solid which was used directly in the next step: $^1$H NMR (CDCl$_3$/300 MHz) δ 7.90 (d, J=8.66 Hz, 2H), 7.29–7.24 (m, 3H), 7.11 (dd, J=8.46, 2.21 Hz, 1H), 6.88 (d, J=8.46 Hz, 1H), 4.19 (s, 2H), 3.86 (s, 3H), 2.55 (s, 3H).

Step 5. Preparation of 1-(3-chloro-4-methoxyphenyl)-2-[4-(methylthio)phenyl]-ethan-1-one oxime.

1-(3-Chloro-4-methoxyphenyl)-2-[4-(methylthio)-phenyl]-ethan-1-one oxime was prepared in 41% yield from the reaction of 1-(3 chloro-4-methoxyphenyl)-2-[4-(methylthio)phenyl]-ethan-1-one from Step 4 with hydroxylamine by the method outlined in Example 1, Step 1: $^1$H NMR (CDCl$_3$/300 MHz) δ 7.69 (d, J=2.22 Hz, 1H), 7.47 (dd, J=8.66, 2.22 Hz, 1H), 7.21–7.16 (m, 4H), 6.86 (d, J=8.66 Hz, 1H), 4.11 (s, 2H), 3.89 (s, 3H), 2.44 (s, 3H).

Step 6. Preparation of 3-(3-chloro-4-methoxyphenyl)-4-[4 methylsulfonylphenyl]-5-methylisoxazole.

3-(3-Chloro-4-methoxyphenyl)-5-methyl-4-[4-(methylthio)phenyl]isoxazole was prepared in 26% yield from 1-(3-chlori-4-methoxyphenyl)-2-[4-(methylthio)phenyl]-ethan-1-one oxime from Step 5 and acetic anhydride by the method described in Example 4, Step 1 and then oxidized to 3-(3-chloro-4 methoxyphenyl)-5-methyl-4-[4-methylsulfonylphenyl]isoxazole with Oxone® by the method described in Example 5, Step 4: Mass spectrum: MLi+=384. High resolution mass spectrum calc'd. for C$_{18}$H$_{17}$ClNO$_4$S (M+H): 378.0567. Found: 378.0573.

EXAMPLE 8

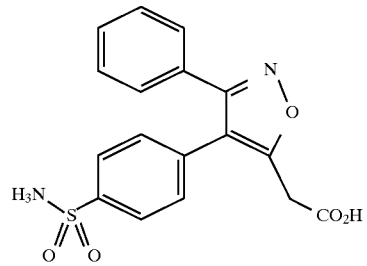

[4-[4-(Methylsulfonyl)phenyl]-3-phenyl)isoxazol-5-yl]acetic acid

Step 1. Preparation of [4-[4-(methylthio)phenyl]-3-phenylisoxazol-5-yl]acetic acid.

[4-[4-(Methylthio)phenyl]-3-phenylisoxazol-5-yl]acetic acid was prepared in 35% yield by carboxylation of 4-[4-(methylthio)phenyl]-5-methyl-3-phenylisoxazole [Example 5, Step 3] according to the procedure detailed in Example 6, Step 4: Mass spectrum: MH+=326. High resolution mass spectrum calc'd. for C$_{18}$H$_{15}$NO$_3$S: 325.0773. Found: 325.0776.

Step 2. Preparation of [4-[4-(methylsulfonyl)phenyl]-3-phenylisoxazol-5-yl]acetic acid.

[4-[4-(Methylsulfonyl)phenyl]-3-phenyl)isoxazol-5-yl] acetic acid was prepared in 80% yield from [4-[4-(methylthio)phenyl]-3-phenylisoxazol-5-yl]acetic acid (Step 1) by oxidation with Oxone® according to the procedure detailed in Example 5, Step 4: Mass spectrum: MH+= 326. High resolution mass spectrum calc'd. for C$_{18}$H$_{16}$NO$_5$S (M+H): 358.0749. Found: 358.0769.

EXAMPLE 9

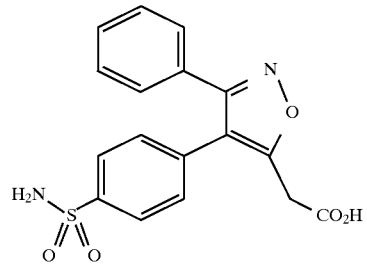

[4-[4-(Aminosulfonyl)phenyl]-3-phenylisoxazol-5-yl]acetic acid

Step 1. Preparation of 3,4-diphenyl-5-methylisoxazole.

A solution of desoxybenzoin keto-oxime (Example 1, Step 1) (6.00 g, 28.40 mmol) in anhydrous tetrahydrofuran (80 mL) was cooled to −20° C. To this solution, n-butyllithium (1.6N in hexanes, 44.4 mL) was added, via syringe, over 35 minutes, such that the reaction temperature remained at or below −10° C. The deep red solution was stirred at −10° C. for 1 hour, warmed to room temperature, then stirred at room temperature for an additional hour. Acetic anhydride (3.2 mL, 34.1 mmol) was added in one portion, and the resulting suspension was stirred without temperature control for 2 hours. Water (100 mL) was added, and the solution was poured into 1N HCl (100 mL) and extracted with ethyl acetate (2×200 mL). The combined organic solution was washed with HCl (1N HCl, 100 mL) and brine (100 mL), dried over anhydrous $MgSO_4$ and filtered. The resulting solution was concentrated in vacuo to yield a crude oil. The oil was applied to a column of silica gel and eluted with ethyl acetate/hexane (10–50% ethyl acetate) to yield, upon concentration of the appropriate fractions, 3,4-diphenyl-4-hydrido-5-hydroxy-5-methylisoxazole (5.0 g). The 3,4-diphenyl-4-hydrido-5-hydroxy-5-methylisoxazole (5.00 g, 19.74 mmol) was added to 300 mg of concentrated $H_2SO_4$ and 30 mL of toluene. The solution was heated to reflux for 1 hour and washed with water. The toluene solution was dried over anhydrous $MgSO_4$, filtered, and concentrated in vacuo and the residue used directly in the next step without further purification.

Step 2. Preparation of (3,4-diphenylisoxazol-5-yl)acetic acid:

(3,4-Diphenylisoxazol-5-yl)acetic acid was prepared in 53% yield by carboxylation of 3,4-diphenyl- 5-methyl-isoxazole (Step 1) according to the procedure outlined in Example 6, Step 4: Mass spectrum: MH+=280. High resolution mass spectrum calc'd. for $C_{17}H_{14}NO_3$(M+H): 280.0894. Found: 280.0897. Anal. Calc'd. for $C_{17}H_{13}NO_3$: C, 73.11; H, 4.69; N, 5.01. Found: C, 72.91; H, 4.73; N, 4.97.

Step 3. Preparation of [4-[4-(aminosulfonyl)phenyl]-3-phenylisoxazol-5-yl]acetic acid:

[4-[4-(Aminosulfonyl)phenyl]-3-phenylisoxazol-5-yl] acetic acid was prepared in 60% yield by chlorosulfonation followed by ammonolysis of 1-(3,4-diphenylisoxazol-5-yl) acetic acid according to the procedure outlined in Example 2, Step 4: mp 61° C. Mass spectrum: MH+=359.

EXAMPLE 10

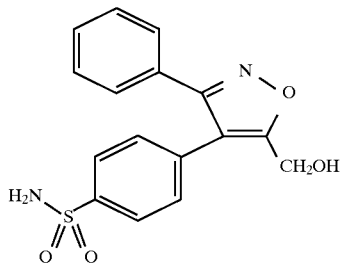

4-[5-Hydroxymethyl-3-phenylisoxazol-4-yl]benzenesulfonamide

4-[5-Methyl-3-phenyl-4-yl]benzenesulfonamide (Example 1) (20.965 g, 66.69 mmol) and THF (1.4 L) were cooled to −78° C. (dry-ice/acetone bath) and a premeasured volume of n-BuLi (167 mL, 266.76 mmol) was added, causing the reaction solution to become bright red. After 15 minutes the dry ice/acetone bath was replaced with a Nacl/ice/water bath, the reaction was warmed to −5° C. over 15 minutes and maintained at −5° C. for 30 more minutes. The NaCl/ice/$H_2O$ bath was replaced with a dry ice/acetone bath and the reaction was chilled to −71° C. Oxygen was added via two 14 gauge needles (ca. 4 psi) and a similar outlet provided. Within 10 minutes the reaction, formerly a red suspension, became an ocre-yellow suspension. Oxygen addition was continued for 30 more minutes. The oxygen line and vents were removed and trimethyl phosphite (67 mL, 566.97 mmol) was added via syringe. After 15 minutes, a solution of HOAc (125 mL) and $H_2O$ (125 mL) was added in one portion causing the solution to become a hazy bright yellow and the reaction temperature to rise to −50° C. The dry ice bath was removed and the reaction was warmed to room temperature. Brine (700 mL) and 1N HCl (134 mL) were added and stirred for 15 minutes. Ethyl acetate (700 mL) was added and the layers were separated. The aqueous phase was washed with ethyl acetate (150 mL) and the organic layers were combined. The organic layer was washed with water, $NaHCO_3$ (5×100 mL) and brine, dried over anhydrous $MgSO_4$, and filtered. The resulting organic phase was diluted with toluene (125 mL) and concentrated in vacuo three times yielding a brown viscous oil. The crude product was purified by flash chromatography [silica gel, 10×18 cm column, hexane/ethyl acetate (½) with a step gradient to hexane/ethyl acetate (½)] yielding a yellow solid (11.25 g). The product was dissolved in ethyl acetate (500 mL) and acetone (60 mL). Partial concentration of this solution and addition of hexane yielded a yellow solid which was collected by vacuum filtration. This solid was dissolved in a minimum of acetone and added to hot $H_2O$ (800 mL at 70° C.) yielding the desired product as a very fine crystalline yellow product (7.89 g, 36%): mp 188°–189° C. $^1$H NMR (DMSO-$d_6$) δ 7.81 (d, J=8.26 Hz, 2H), 7.26–7.55 ( m, 9H), 5.77 (t, J=4.84, 1H), 4.54 (d, J=4.84, 2H). Anal. Calc'd. for $C_{16}H_{14}N_2O_4S$: C, 58.17; H, 4.27; N, 8.48. Found: C, 58.22; H, 4.31; N, 8.50. Mass spectrum: M+H : 331.

EXAMPLE 11

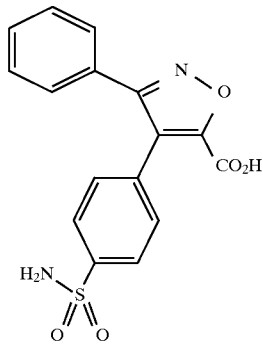

[4-[4-(Aminosulfonyl)phenyl]-3-phenylisoxazol-5-yl]carboxylic acid

To a solution of 4-[5-hydroxymethyl-3-phenyl-4-yl] benzenesulfonamide (Example 10) (0.64 g, 1.94 mmol) in acetone at −78° C. (dry ice-acetone bath) was added carefully Jones reagent (0.7 mL of 2.44M $CrO_3$ in aqueous $H_2SO_4$ solution). The reaction was warmed to 0° C. and an additional 0.7 mL (2.44M $CrO_3$ in aqueous $H_2SO_4$ solution) was added. The reaction was warmed to room temperature and stirred overnight. Isopropanol (2 mL) was added and the reaction was stirred for 2 hours. The reaction was diluted with ethyl acetate, washed with $H_2O$, dried over anhydrous $MgSO_4$, filtered through Celite® and concentrated in vacuo yielding a solid. recrystallization of this solid from toluene yielding the desired product (0.075 g, 11%) as a tan solid: mp >300° C. $^1$H NMR (DMSO-$d_6$) δ 7.70 (d, J=8.46 Hz, 2H) 7.08–7.50 (m, 9H).

EXAMPLE 12

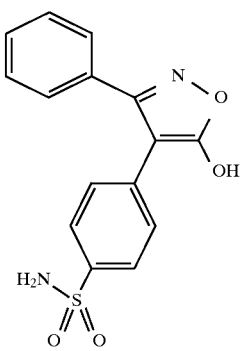

4-[5-Hydroxy-3-phenylisoxazol-4-yl] benzenesulfonamide

Step 1. Preparation of 3,4-diphenylisoxazolin-5-one.

To a stirred solution of the deoxybenzoin oxime (50.59 g, 239 mmol) in anhydrous THF (1 L) under nitrogen atmosphere, and chilled to −78° C. (dry ice/acetone bath) was added n-BuLi (375 mL of 1.6M in hexanes, 599 mmol) via cannula over 15 minutes. After twenty minutes at −78° C., the dry ice/acetone bath was replaced with a NaCl/ice/H$_2$O and the reaction was warmed to 0° C. over 1 hour. The NaCl/ice/H$_2$O bath was replaced with a dry ice/acetone bath. When −78° C. was reached, the reaction was transferred to 1500 cc of powdered dry ice and the resulting yellow mixture was held overnight at room temperature. The clear, straw colored solution was mixed with 700 mL of 3N HCl. The reaction was heated to reflux for 1 hour and cooled to room temperature. The reaction was diluted with brine (500 mL) and the layers were separated. The aqueous layer was extracted with dichloromethane/ethyl acetate (⅔) (400 mL). The organic layers were combined and washed with brine (200 mL), dried over anhydrous MgSO$_4$, filtered and concentrated yielding a brown solid. The solid was redissolved in warm THF and hexanes were added yielding a fluffy off-white crystalline solid (30.4 g, 54%). A second crop was obtained (12.66 g, 22%): mp 162°–163° C. (dec.) . This material was suitable for use without further purification.

Step 2. Preparation of 4-[5-hydroxy-3-phenyl-4-yl] benzenesulfonamide.

3,4-Diphenylisoxazolin-5-one from step 1 (15.6 g, 65.75 mmol) was added carefully to ClSO$_3$H (160 mL) chilled in a NaCl/ice bath. After 2 hours, the crude reaction mixture was carefully poured over ice, yielding the crude sulfonyl chloride as a precipitate which was collected by vacuum filtration. The solid was dissolved in dichloromethane yielding two phases which were separated, and the organic phase dried over anhydrous MgSO$_4$. This clear pale yellow solution was slowly added to a chilled (0° C.) saturated solution of NH$_3$ in dichloromethane. The resulting suspension was diluted with CH$_3$OH and washed with KHSO$_4$ (0.25M). The organic layer was dried over anhydrous MgSO$_4$, filtered and concentrated in vacuo yielding a tan solid which was collected by vacuum filtration. This solid was dissolved in a minimum of 1N NaOH solution, filtered, and washed with dichloromethane. The aqueous layer was acidified with concentrated HCl yielding and off-white solid (3.70 g, 18%): mp 207° C. (dec.). $^1$H NMR (D$_2$O with NaOD) δ 7.48 (d, J=8.46 Hz, 2H), 7.38–7.20 (m, 5H), 7.14, (d, J=8.26 Hz, 2H). The methanolic/aqueous KHSO$_4$ wash phase, upon partial evaporation yielded additional desired product as a tan solid (8.94 g, 43%).

EXAMPLE 13

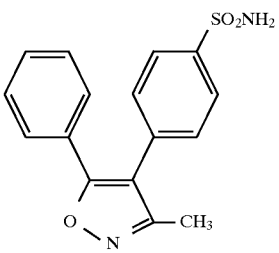

4-[3-Methyl-5-phenylisoxazol-4-yl] benzenesulfonamide

Step 1. Preparation of 1,2-diphenyl-1-butene-3-one oxime.

A solution of 1,2-diphenyl-1-butene-3-one (1.5g, 7 mmol) in EtOH (15 mL) and was added to a solution of hydroxylamine hydrochloride (500 mg, 7 mmol) and NaHCO$_3$ (1 g) in water (7 mL). The mixture was heated to reflux for 5 hours at which time thin layer chromatography indicated the reaction was incomplete. Additional hydroxylamine hydrochloride (500 mg, 7 mmol) was added and heating at reflux was continued overnight. The reaction was cooled, poured into water (100 mL) and extracted with ethyl acetate. The combined organic layers were dried over sodium sulfate, filtered and the filtrate concentrated in vacuo. The crude material was chromatographed on silica gel using 5% ethyl acetate in toluene as the eluant to give 450 mg (30%) of the desired oxime as a crystalline solid: mp 138°–141° C. Anal. Calc'd. for C$_{16}$H$_{15}$NO: C, 80.98; H, 6.37; N, 5.90. Found: C, 80.79; H, 6.25; N, 6.09.

Step 2. Preparation of 3,4-diphenyl-5-methylisoxazole

To a solution of oxime from Step 1 (450 mg, 1.9 mmol) and sodium bicarbonate (650 mg, 7.7 mmol) in tetrahydrofuran (6 mL) and water (6 mL) in a vessel wrapped in aluminum foil was added a solution of potassium iodide (1.1 g, 6.6 mmol) and iodine (525 mg, 2 mmol) in water (4 mL). The reaction was heated to reflux for 7 hours and stirred at room temperature overnight. Saturated aqueous sodium bisulfite solution (5 mL) was added and the reaction mixture was extracted with ethyl acetate. The combined organic layers were dried over sodium sulfate and the crude material was isolated after filtration and concentration of the filtrate. Chromatography on silica gel using toluene as the eluant gave 290 mg (57%) of the isoxazole as an oil which crystallized on standing: mp 92°–94° C. Anal. Calc'd for C$_{16}$H$_{13}$NO: C, 81.31; H, 5.57; N, 5.95. Found: C, 81.31, H, 5.71; N, 6.18.

Step 3. Preparation of 4-[3-methyl-5-phenylisoxazol-4-yl] benzenesulfonamide.

A solution of the isoxazole from step 2 (250 mg, 1.1 mmol) in chlorosulfonic acid (1 mL) was stirred at 0° C. for 3 hours. The reaction was cautiously added to concentrated ammonium hydroxide (6 mL) in the cold (0° C.). The resultant reaction mixture was stirred at 0° for 1 hour. The reaction was cautiously diluted with water and extracted with ethyl acetate. The combined organic layers were dried over sodium sulfate, filtered, and the filtrate was concentrated in vacuo to give the crude product. This material was chromatographed on silica gel using 25% ethyl acetate in toluene as the eluant to give the desired sulfonamide as a crystalline solid (110 mg, 40%): mp 185°–187° C. Anal. Calc'd. for C$_{16}$H$_{14}$N$_2$O$_3$S: C, 61.13; H, 4.49; N, 8.91; S, 10.20. Found: C, 60.88; H, 4.61; N, 8.55; S, 10.40.

EXAMPLE 14

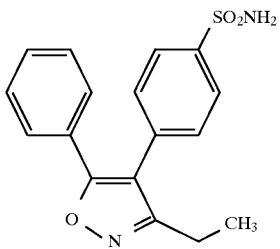

4-[3-Ethyl-5-phenylisoxazol-4-yl]benzenesulfonamide

Step 1. Preparation of 1,2-diphenyl-1-pentene-3-one

Hydrogen bromide (30% in acetic acid, 30 mL) was added (15 minutes) to a solution of 1-phenyl-2-butanone (14.8 g, 0.10 mole) and benzaldehyde (10.6 g, 0.10 mole) in acetic acid (100 mL) at 0° C. and stirred at room temperature for 20 hours. The reddish mixture was poured into 750 mL cold water and stirred for 15 minutes. The material was extracted into ethyl acetate. The combined ethyl acetate extracts were washed with water (5×100 mL), dried over sodium sulfate, filtered and concentrated. Purification by silica gel chromatography yielded the ketone as an oil, which was used directly in the next step.

Step 2. Preparation of 1,2-diphenyl-1-pentene-3-one oxime.

Potassium hydroxide (0.77 g, 0.014 mole) was added to a solution of hydroxylamine HCl (0.95 g, 0.014 mole) in water (4 mL). Ethyl alcohol (40 mL) was added and a white solid was filtered. The filtrate was added to a solution of 1,2-diphenyl-1-pentene-3-one (Step 1) (2.7 g, 0.011 mole) in ethyl alcohol (10 mL). After heating to 75° C. for 3.5 hours, the solution was concentrated to an oily solid. Purification by silica gel chromatography and recrystallization from hexane gave the oxime as a white solid: Anal. Calc'd. for $C_{17}H_{17}NO$ (251.33): C, 81.24; H, 6.82; N, 5.57. Found: C, 81.37; H, 6.87; N, 5.50.

Step 3. Preparation of 4,5-diphenyl-3-ethylisoxazole

A solution of $NaHCO_3$ (1.34 g, 0.016 mole) in water (13 mL) was added to a solution of 1,2-diphenyl-1-pentene-3-one oxime (Step 2) (1.0 g, 0.004 mole) in THF (14 mL). The reaction vessel was covered with aluminum foil. A solution of potassium iodide (2.31 g, 0.014 mole) and iodine (1.11 g, 0.0044 mole) in water (8.5 mL) was added dropwise over 5 minutes, and the resulting solution was heated to reflux for 5 hours. After cooling to room temperature, a saturated solution of sodium bisulfite (10 mL) was added. Water (50 mL) was added and the mixture was extracted into ethyl acetate (100 mL). The ethyl acetate solution was dried over $NaSO_4$, filtered and concentrated to an oil. Purification by silica gel chromatography yielded the isoxazole: Anal. Calc'd. for $C_{17}H_{15}NO$ (249.32): C, 81.90; H, 6.06; N, 5.62. Found: C, 82.08; H, 5.83; N, 5.62.

Step 4. Preparation of 4-[3-ethyl-5-phenylisoxazol-4-yl] benzenesulfonamide

A solution of the isoxazole (Step 3) (14 g, 0.043 mole) in chlorosulfonic acid (15 mL) was stirred at 0° C. for 4 hours. The cold solution was added dropwise very slowly to ammonium hydroxide (100 mL). After stirring for 1 hour, water (100 mL) was added and the mixture was extracted into ethyl acetate (2×250 mL). The combined ethyl acetate extracts were dried over $Na_2SO_4$, filtered and concentrated to give a solid. The crude solid was purified by silica gel chromatography to give the sulfonamide as a solid: mp 167° C. (DSC). Anal. Calc'd. for $C_{17}H_{16}N_2O_3S$: C, 62.18; H, 4.91; N, 8.53. Found: C, 62.20; H, 4.75; N, 8.48.

EXAMPLE 15

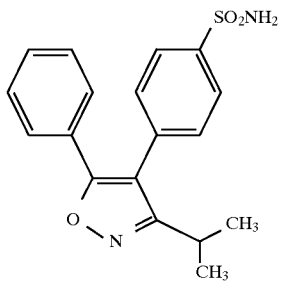

4-[3- Isopropyl-5-phenylisoxazol-4-yl]benzenesulfonamide

Step 1: Preparation of 1,2-diphenyl-4-methyl-1-penten-3-one

A solution of benzaldehyde (6.5g, 0.0617 mole), 3-methyl-1-phenyl-2-butanone (10 g, 0.0617 mole) and piperidine (0.2 g) in benzene (50 ml) was heated to reflux for 20 hours. Water formed during the reaction was removed (azeotrope) by the use of a Dean-Stark trap. The reaction was concentrated to an oil, and the product was purified by silica gel chromatography.

Step 2: Preparation of 4-[3-isopropyl-5-phenylisoxazol-4-yl]benzenesulfonamide

By following the method of Example 14, steps 2–4 and by substituting 1,2-diphenyl-4-methyl-1-penten-3-one for 1,2-diphenyl-1-penten-3-one, the titled product was obtained: mp 205° C. (DSC) Anal. Calc'd. for $C_{18}H_{18}N_2O_3S$: C, 63.14; H, 5.30; N, 8.18. Found: C, 62.80; H, 5.37; N, 7.89.

EXAMPLE 16

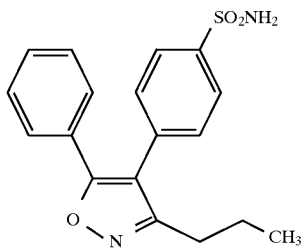

4-[5-Phenyl-3-propylisoxazol-4-yl]benzenesulfonamide

By substituting 1-phenyl-2-pentanone for 3-methyl-1-phenyl-2-butanone in the method of Example 15, the titled product was obtained: mp 167° C. (DSC). Anal. Calc'd. for $C_{18}H_{18}N_2O_3S$: C, 63.14; H, 5.30; N, 8.18. Found: C, 62.95; H, 5.51; N, 8.01.

EXAMPLE 17

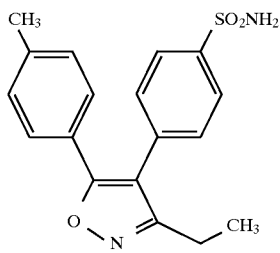

4-[3-Ethyl-5-(4-methylphenyl)isoxazol-4-yl]
benzenesulfonamide

By following the method of Example 15 and substituting para-tolualdehyde for benzaldehyde and 1-phenyl-2-butanone for 3-methyl-1-phenyl-2-butanone, the titled material was prepared: mp 191° C. (DSC). Anal. Calc'd. for $C_{18}H_{18}N_2O_3S$: C, 63.14; H, 5.30; N, 8.18. Found: C, 63.06; H, 5.26; N, 8.10.

EXAMPLE 18

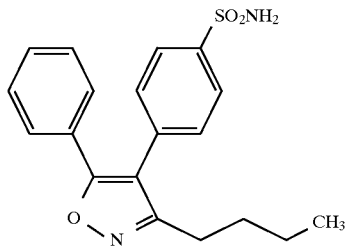

4-[3-Butyl-5-phenylisoxazol-4-yl]
benzenesulfonamide

Step 1. Preparation of 1-phenyl-2-hexanone

Butyl magnesium bromide (2.0M in THF, 200 mL, 0.4 mole) was added dropwise to a stirred cold (−5° C.) slurry of methyl phenyl acetate (9.8 g, 0.065 mole) and N,O-dimethylhydroxylamine HCl (7 g, 0.072 mole) in 600 mL THF over 1.5 hours. After stirring at room temperature for 20 hours, 1N HCl (100 mL) was added dropwise. After 1.5 hours, water (100 mL) was added and the layers were separated. The organic layer was dried over $Na_2SO_4$, filtered and concentrated to an oil. The hexanone was purified by silica gel chromatography.

Step 2. Preparation of 4-[3-butyl-5-phenylisoxazol-4-yl]benzenesulfonamide

By substituting 1-phenyl-2-hexanone (Step 1) for 1-phenyl-2-butanone in the method of Example 14, the titled product was obtained: mp 150° C. (DSC). Anal. Calc'd. for $C_{19}H_{20}N_2O_3S$: C, 64.02; H, 5.66; N, 7.86. Found: C, 63.70; H, 5.93; N, 7.75.

EXAMPLE 19

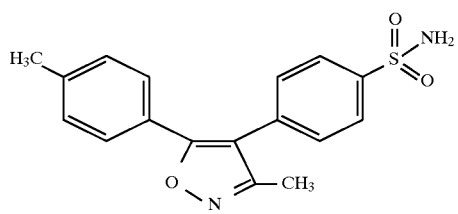

4-[3-Methyl-5-(4-methylphenyl)isoxazol-4-yl]
benzenesulfonamide

Step 1. Preparation of 4-(4-methylphenyl)-3-phenyl-3-butene-2-one

A solution of phenylacetone (5 g, 37 mmol), p-tolualdehyde (4.5 g, 37 mmol) and piperidine (125 mg) in benzene (30 mL) was heated to reflux for 24 hours. The mixture was concentrated and the crude material was chromatographed on silca gel using mixtures of ethyl acetate and hexane as the eluents to give 3 g of the desired ketone as an oil. This material was suitable for use without further purification.

Step 2. Preparation of 4-[3-methyl-5-(4-methylphenyl)isoxazol-4-yl]benzenesulfonamide By substituting 4-(4-methylphenyl)-3-phenyl-3-butene-2-one (Step 1) for 1,2-diphenyl-1-pentene-3-one in the method of Example 14, the titled product was obtained: mp 191°–193° C. Anal. Calc'd. for $C_{17}H_{16}N_2O_3S$ (328.39): C, 62.18; H, 4.91; N, 8.53; S, 9.76. Found: C, 61.93; H, 4.95; N, 8.36; S, 9.40.

EXAMPLE 20

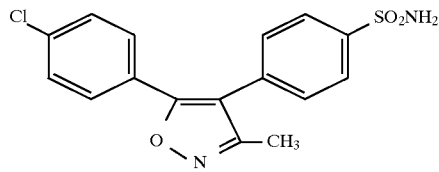

4-[5-(4-Chlorophenyl)-3-methylisoxazol-4-yl]
benzenesulfonamide

Step 1. Preparation of 4-(4-chlorophenyl)-3-phenyl-3-butene-2-one

Following the procedure of Example 19, step 1, phenylacetone (7.9 g, 58 mmol) was reacted with p-chlorobenzaldehyde (8.15 g, 58 mmol) in the presence of piperidine (125 mg) in benzene (40 mL). The crude material was purified by recrystallization from ethanol to give 5.5 g (45%) of the desired ketone as a crystalline solid: mp 126°–127° C. Anal. Calc'd. for $C_{16}H_{13}OCl$ (256.73): C, 74.85; H, 5.10; Cl, 13.81. Found: C, 74.75; H, 5.01; Cl, 13.61.

Step 2. Preparation of 4-[5-(4-chlorophenyl)-3-methylisoxazol-4-yl]benzenesulfonamide By substituting 4-(4-chlorophenyl)-3-phenyl-3-butene-2-one (Step 1) for 1,2-diphenyl-1-pentene-3-one in the method of Example 14, the titled product (950 mg, 31%) was obtained: mp: 194°–197° C. Anal. Calc'd. for $C_{16}H_{13}N_2O_3ClS$ (348.81): C, 55.10; H, 3.76; N, 8.03; S, 9.19. Found: C, 55.16; H, 3.87; N, 7.72; S, 9.33.

EXAMPLE 21

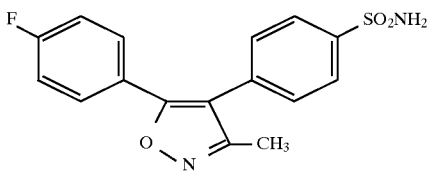

4-[5-(4-Fluorophenyl)-3-methylisoxazol-4-yl]
benzenesulfonamide

Step 1. Preparation of 4-(4-fluorophenyl)-3-phenyl-3-butene-2-one

Following the procedure of Example 19, step 1, phenylacetone (6.75 g, 50 mmol) was reacted with 4-fluorobenzaldehyde (6.25 g, 50 mmol) in the presence of piperidine (125 mg) in benzene (40 mL). The crude material was recrystallized from hexane to give 7.9 g (66%) of the desired material as a crystalline solid, mp 88°–89° C. Anal. Calc'd. for $C_{16}H_{13}FO$ (240.28): C, 79.98; H, 5.45. Found: C, 79.66; H, 5.50.

Step 2. Preparation of 4-[5-(4-fluorophenyl)-3-methylisoxazol-4-yl]benzenesulfonamide By substituting 4-(4-fluorophenyl)-3-phenyl-3-butene-2-one (Step 1) for 1,2-diphenyl-1-pentene-3-one in the method of Example 14, the titled product (225 mg, 40%) was obtained: mp 174°–175° C. Anal. Calc'd. for $C_{16}H_{13}N_2FO_3S$ (332.36): C, 57.82; H, 3.94; N, 8.43; S, 9.65. Found: C, 57.66; H, 3.84; N, 8.22; S, 9.78.

EXAMPLE 22

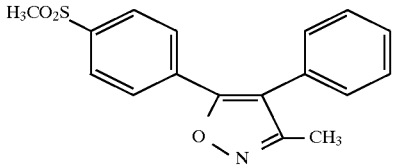

3-Methyl-5-(4-methylsulfonylphenyl)-4-phenylisoxazole

Step 1. Preparation of 4-(4-methylthiophenyl)-3-phenyl-3-butene-2-one

Following the procedure of Example 19, step 1, phenylacetone (5 g, 35 mmol) was reacted with 4-methylthiobenzaldehyde (5.25 g, 35 mmol) in the presence of piperidine (125 mg) in benzene (40 mL). The crude material was recrystallized from ethyl acetate and hexane to give the ketone (3 g, 32%): mp 67°–68° C. Anal. Calc'd. for $C_{17}H_{16}OS$ (268.38): C, 76.08; H, 6.01; S, 11.95. Found: C, 75.80; H, 5.91; S, 11.89.

Step 2. Preparation of 4-(4-methylthiophenyl)-3-phenyl-3-butene-2-one oxime

A solution of the ketone from Step 1 (3 g, 11 mmol), hydroxylamine hydrochloride (765 mg, 11 mmole) and sodium acetate (905 mg, 11 mmol) in ethanol (30 mL) and water (3 mL) was heated at reflux for 90 minutes. The reaction was cooled, water (25 mL) was added and the crude oxime was filtered. Recrystallization from ethanol and water gave pure oxime (2.65 g, 85%): mp 151°–152° C. Anal. Calc'd. for $C_{17}H_{17}NOS$ (283.39): C, 72.05; H, 6.05; N, 4.94; S, 11.31. Found: C, 71.96; H, 6.10; N, 4.71; S, 11.45.

Step 3. Preparation of 5-(4-methylthio-phenyl)-4-phenyl-3-methylisoxazole

Following the procedure of Step 2 of Example 13, the oxime from Step 2 (500 mg, 1.7 mmol) was reacted with iodine (450 mg, 1.7 mmol) and potassium iodide (1 g, 6 mmol) in the presence of sodium bicarbonate (600 mg, 7 mmol) in tetrahydrofuran (10 mL) and water (10 mL). The crude material was chromatographed on silica gel using toluene as the eluent. The material isolated was recrystallized from ethyl acetate and hexane to give the desired isoxazole (460 mg, 96%): mp 88°–90° C. Anal. Calc'd. for $C_{17}H_{15}NOS$ (281.38): C, 72.57; H, 5.37; N, 4.98; S, 11.40. Found: C, 72.19; H, 5.49; N, 4.66; S, 11.79.

Step 4. Preparation of 3-methyl-5-(4-methylsulfonylphenyl)-4-phenylisoxazole

To a solution of the isoxazole from Step 3 (450 mg, 1.6 mmol) in tetrahydrofuran (6 mL) and methanol (12 mL), was added dropwise a solution of Oxone® (1.6 g) in water (6 mL) at room temperature. The reaction was stirred for 2 hours, diluted with water and filtered. The crude product was recrystallized from ethyl acetate and hexane to give pure sulfone (475 mg, 95%): mp 183°–185° C. Anal. Calc'd. for $C_{17}H_{15}NO_3S$ (313.38): C, 65.16; H, 4.82; N, 4.47; S, 10.23. Found: C, 65.06; H, 4.93; N, 4.31; S, 10.37.

EXAMPLE 23

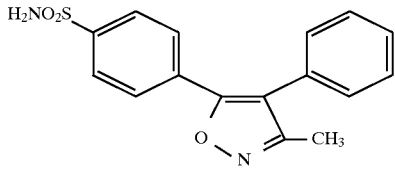

4-[3-Methyl-4-phenylisoxazol-5-yl]
benzenesulfonamide

Step 1. Preparation of 3-(4-trimethylsilylethylsulfonylphenyl)-4-phenyl-5-methylisoxazole Lithium diisopropylamide was prepared in tetrahydrofuran (15 mL) from diisopropylamine (850 mg, 8.4 mmol) and n-butyllithium (4.2 mL of 1.84M in THF, 7.7 mmol) at −70° C. under argon. A solution of 5-(4-methylsulfonylphenyl)-4-phenyl-3-methylisoxazole from Example 22 (2.0 g, 6.4 mmol) in tetrahydrofuran (15 mL) was added at −70° C. over 10 minutes and stirred for an additional 45 minutes. A solution of trimethylsilyliodomethane (2.0 g, 9.6 mmol) in tetrahydrofuran (10 mL) was added cold over 10 minutes, stirred for 15 minutes and warmed to 25° C. After stirring for 24 hours, water was added and the mixture was extracted with ethyl acetate. The organic extracts were dried over magnesium sulfate. After filtration and concentration, the crude silyl ether was purified with silica gel chromatography using mixtures of ethyl acetate and toluene to give 2.0 g of desired silyl compound. This material was used without further purification.

Step 2. Preparation of 4-[3-methyl-4-phenylisoxazol-5-yl]
benzenesulfonamide

A solution of the silyl ether from Step 1 (2.0 g, 5 mmol) and tetra-n-butylammonium fluoride (15 mL of 1M in tetrahydrofuran, 15 mmol) in tetrahydrofuran (16 mL) was heated to reflux for 2 hours under an argon atmosphere. After cooling to room temperature, a solution of sodium acetate (1.85 g, 22.5 mmoles) in water (10 mL) was added, followed by hydroxylamine-O-sulfonic acid (2.85 g, 25 mmol). The reaction mixture was stirred for 18 hours at room temperature. Water and ethyl acetate were added and the organic phase was separated and dried over magnesium sulfate. The dried solution was filtered and concentrated in vacuo. The crude product was chromatographed using mixtures of ethyl acetate and toluene as eluents. The chromatographed product was recrystallized from ethyl acetate and hexane to give the desired sulfonamide (1.0 g, 64%): mp 187°–188° C. Anal. Calc'd. for $C_{16}H_{14}N_2O_3S$ (314.36): C, 61.13; H, 4.49; N, 8.91; S, 10.20. Found: C, 61.19; H, 4.57; N, 8.82; S, 10.23.

EXAMPLE 24

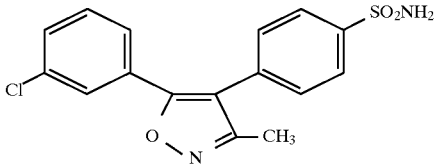

4-[5-(3-Chlorophenyl)-3-methylisoxazol-4-yl]benzenesulfonamide

Step 1. Preparation of 4-(3-chlorophenyl)-3-phenyl-3-butene-2-one

Following the procedure of Example 19, step 1, phenylacetone (5 g, 37 mmol) was reacted with 3-chlorobenzaldehyde (5.25 g, 37 mmol) in the presence of piperidine (125 mg) in benzene (30 mL). The crude ketone was recrystallized from ethyl acetate and hexane to give the desired ketone (5.5 g, 57%): mp 91°–92° C. Anal. Calc'd. for $C_{16}H_{13}ClO$ (256.73): C, 74.85; H, 5.10. Found: C, 74.67; H, 5.19.

Step 2. Preparation of 4-(3-chlorophenyl)-3-phenyl-3-butene-2-one oxime

Following the procedure of Example 22, Step 2, a solution of the ketone from Step 1 (5.5 g, 20 mmol), hydroxylamine hydrochloride (1.5 g, 20 mmol) and sodium acetate (1.7 g, 20 mmol) in ethanol and water was heated to reflux. The crude oxime was recrystallized from ethanol and water to give pure oxime (5 g, 89%): mp 161°–163° C. Anal. Calc'd. for $C_{16}H_{14}ClNO$ (271.75): C, 70.72; H, 5.19; N, 5.15. Found: C, 70.55; H, 5.25; N, 5.09.

Step 3. Preparation of 5-(3-chlorophenyl)-4-phenyl-3-methylisoxazole

Following the procedure of Step 2 of Example 13, the oxime from Step 2 (5 g, 18 mmol) was reacted with iodine (4.7 g, 18 mmol) and potassium iodide (10.6 g, 63 mmol) in the presence of sodium bicarbonate (6.3 g, 74 mmol) in tetrahydrofuran (100 mL) and water (80 mL). The crude isoxazole was recrystallized from ethyl acetate and hexane to give pure isoxazole (4.8 g, 95%): mp 101°–103° C. Anal. Calc'd. for $C_{16}H_{12}ClNO$ (269.73): C, 71.25; H, 4.48; N, 5.19. Found: C, 71.10; H, 4.28; N, 5.00.

Step 4. Preparation of 4-[3-methyl-5-(3-chlorophenyl)isoxazol-4-yl]benzenesulfonamide Following the procedure of Example 14, Step 4, the isoxazole from Step 3 (2 g, 7.4 mmol) was reacted with chlorosulfonic acid (8 mL) and quenched with ammonium hydroxide. The crude product was recrystallized from ethyl acetate to give pure sulfonamide (220 mg): mp 176°–178° C. Anal. Calc'd. for $C_{16}H_{13}ClN_2O_3S$ (348.81): C, 55.10; H, 3.76; N, 8.03; S, 9.19. Found: C, 54.60; H, 3.63; N, 7.77; S, 9.21.

EXAMPLE 25

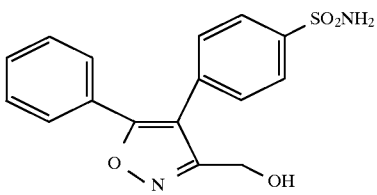

4-[3-Hydroxymethyl-5-phenylisoxazol-4-yl]benzenesulfonamide

To a cold (−70° C.) solution of 4-[3-methyl-5-phenylisoxazol-4-yl]benzenesulfonamide (Example 13) (500 mg, 1.6 mmol) and tetramethylethylenediamine (560 mg, 4.8 mmol) in tetrahydrofuran (15 mL) under an argon atmosphere was added a solution of n-butyllithium (2.6 mL of 1.84M in hexane, 4.8 mmol). The mixture was warmed to −30° C. for 5 minutes and recooled to −70° C. A solution of (1R)-(−)-(10-camphorsulfonyl)oxaziridine (1 g, 4.5 mmol) in tetrahydrofuran (5 mL) was added. After stirring at −70° C. for 10 minutes, the reaction was warmed to room temperature. The reaction was poured into water and extracted with ethyl acetate. The organic extracts were dried over magnesium sulfate, filtered and concentrated. The crude product was chromatographed on silica gel using mixtures of acetone and hexane as eluents. The chromatographed product was recrystallized from ethyl acetate and hexane to give 90 mg of desired alcohol: mp 198°–200° C. Anal. Calc'd. for $C_{16}H_{14}N_2O_4S$ (330.36): C, 58.17; H, 4.27; N, 8.48; S, 9.71. Found: C, 58.18; H, 4.51; N, 8.14; S, 9.58.

EXAMPLE 26

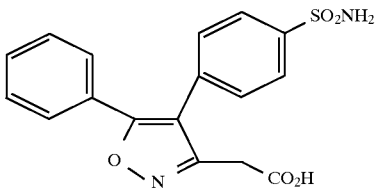

4-(4-Aminosulfonylphenyl)-5-phenyl-isoxazole-3-acetic acid

To a cold (−70° C.) solution of 4-[3-methyl-5-phenylisoxazol-4-yl]benzenesulfonamide, Example 13 (500 mg, 1.6 mmoles) and tetramethylethylenediamine (5 mL) in tetrahydrofuran (15 mL) under an argon atmosphere was added a solution of n-butyllithium (2.6 mL of 1.84M in hexane, 4.8 mmol) over 5 minutes. The reaction was warmed to −30° C. for 5 minutes and recooled to −70° C. Carbon dioxide was bubbled into the mixture for 10 minutes and the temperature was warmed to 25° C. The reaction was poured into 1M hydrochloric acid and extracted with ethyl acetate. The organic phase was dried over magnesium sulfate, filtered and concentrated. The crude product was chromatographed on silica gel using mixtures of ethyl acetate and toluene containing 1% acetic acid as eluents to give 45 mg of desired carboxylic acid as a glass. Anal. Calc'd. for $C_{17}H_{14}N_2O_5S$ (358.37): C, 56.98; H, 3.94; N, 7.82; S, 8.95. Found: C, 56.65; H, 4.09; N, 7.61; S, 9.11.

EXAMPLE 27

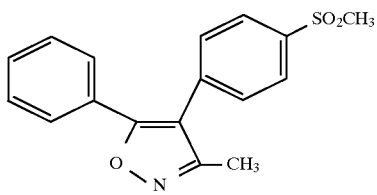

3-Methyl-4-(4-methylsulfonylphenyl)-5-phenylisoxazole

Step 1. Preparation of 4-phenyl-3-(4-methylthiophenyl)-3-butene-2-one

4-Methylthiophenyl acetone was synthesized according to the procedure by G. Y. Lesher described in U. S. Pat. No. 4,517,192, Jan. 31, 1983. Following the procedure of Example 19 (Step 1), 4-methylthiophenylacetone (11.2 g, 62 mmol) was reacted with benzaldehyde (6.6 g, 62 mmol) in the presence of piperidine (150 mg) in benzene (75 mL). The crude material was chromatographed using mixtures of ethyl acetate and hexane as eluents to give the desired ketone as a crystalline solid (14 g, 82%): mp 91°–93° C. Anal. Calc'd. for $C_{17}H_{16}OS$ (268.38): C, 76.08; H, 6.01; S, 11.95. Found: C, 76.15; H, 6.08; S, 11.79.

Step 2. Preparation of 3-methyl-4-(4-methylsulfonylphenyl)-5-phenylisoxazole

By substituting 4-phenyl-3-(4-methylthiophenyl)-3-butene-2-one for 4-(4-methylthiophenyl)-3-phenyl-3-butene-2-one in the method of Example 22, the titled product was obtained (250 mg, 79%): mp 144°–145° C. Anal. Calc'd. for $C_{17}H_{15}NO_3S$ (313.38): C, 65.16; H, 4.82; N, 4.47; S, 10.23. Found: C, 65.26; H, 4.78; N, 3.99; S, 10.22.

EXAMPLE 28

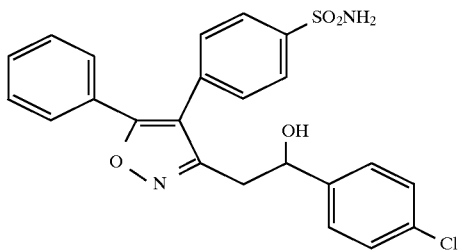

4-[3-[2-(4-Chlorophenyl)-2-hydroxyethyl]-5-phenylisoxazol-4-yl]benzenesulfonamide To a cold (–70° C.) solution of 4-[3-methyl-5-phenylisoxazol-4-yl]benzenesulfonamide (Example 13) (250 mg, 0.8 mmol) and tetramethylethylenediamine (277 mg, 2.4 mmol) in tetrahydrofuran (5 mL) under an argon atmosphere was added n-butyllithium (1.3 mL of 1.84M in hexane, 2.4 mmol). The solution was warmed to –40° C. for 15 minutes, recooled to –70° C., and a solution of 4-chlorobenzaldehyde (337 mg, 2.4 mmol) in tetrahydrofuran (3 mL) was added. The mixture was warmed to room temperature over 30 minutes, poured into water (25 mL) and extracted with ethyl acetate. The organic layer was dried over magnesium sulfate, filtered and the filtrate was concentrated in vacuo. The crude product was chromatographed on silica gel using mixtures of acetone and hexane as eluents to give 165 mg of desired product as a crystalline solid: mp 165°–167° C. Anal. Calc'd. for $C_{23}H_{19}ClN_2O_4S$(454.93): C, 60.72; H, 4.21; N, 6.16; S, 7.05. Found: C, 60.33; H, 4.34; N, 5.87; S, 6.74.

EXAMPLE 29

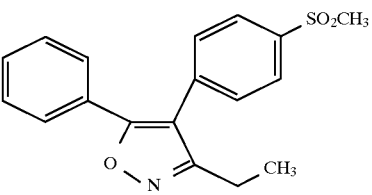

3-Ethyl-4-(4-methylsulfonylphenyl)-5-phenylisoxazole

Step 1. Preparation of N-methoxy-N-methyl-4-(methylthio)benzeneacetamide

To a solution of 4-(methylthio)phenylacetic acid (18.3 g, 0.100 mol) in methylene chloride (200 mL) was added 1,1'-carbonyldiimidazole (16.3 g, 0.100 mol) portionwise. The mixture was stirred at room temperature for 20 minutes, and N,O-dimethylhydroxylamine hydrochloride (9.8 g, 0.100 mol) was added. The reaction mixture was stirred overnight at room temperature, diluted with ether (500 mL) and washed successively with 1N hydrochloric acid, saturated aqueous sodium bicarbonate and brine. The organic layer was dried over magnesium sulfate, filtered and the filtrate was concentrated in vacuo to give 20.9 g of N-methoxy-N-methyl-4-(methylthio)-benzeneacetamide as a clear oil (93%).

Step 2. Preparation of 1-(4-methylthiophenyl)-2-butanone

To a solution of ethyl magnesium bromide (29 mL of 1.0M tetrahydrofuran solution, 0.029 mol) was rapidly added a solution of N-methoxy-N-methyl-4-(methylthio)benzeneacetamide from Step 1 (2.15 g, 9.5 mmol) in 10 mL of dry tetrahydrofuran at –10° C. The reaction mixture was stirred at –10° C. for 10 minutes, then warmed to room temperature over 1 hour. The reaction was quenched with 100 mL of 5% potassium bisulfate and extracted with methylene chloride. The organic layer was washed with water, brine, dried over magnesium sulfate and filtered. The filtrate was concentrated to give the butanone (1.4 g, 76%) as a colorless oil, which crystallized upon standing: mp 39°–41° C. Anal. Calc'd. for $C_{11}H_{14}OS$: C, 68.00; H, 7.26; S, 16.50. Found: C, 68.10; H, 7.38; S, 16.27.

Step 3. Preparation of 2-(4-methylthiophenyl)-1-phenyl-1-pentene-3-one

A mixture of 1-(4-methylthiophenyl)-2-butanone from Step 2 (9.74 g, 50 mmol), benzaldehyde (5.85 g, 55 mmol) and piperidine (0.5 mL) in toluene (200 mL) was heated at reflux with a Dean-Stark trap for 16 hours. The mixture was cooled and solvent was removed in vacuo. The residue was partitioned between dichloromethane and water. The organic layer was washed successively with saturated ammonium chloride solution, water and brine, dried over magnesium sulfate, filtered and the filtrate was concentrated in vacuo. The crude pentenone was recrystallized from ethyl acetate and hexane to give 8.64 g of 2-(4-methylthiophenyl)-1-phenyl-1-pentene-3-one (60%) as light yellow crystals: mp 98°–99° C. Anal. Calc'd. for $C_{18}H_{18}OS$: C, 76.56; H, 6.42; N, 11.35. Found: C, 76.58; H, 6.17; N, 11.35.

Step 4. Preparation of 2-(4-methylthiophenyl)-1-phenyl-1-pentene-3-one oxime

To a suspension of pentenone from Step 3 (8.6 g, 0.031 mol) in 100 mL of ethanol was added a solution of sodium acetate (2.5 g, 0.031 mol) in 10 mL of water, followed by hydroxylamine hydrochloride (2.1 g, 0.031 mol). The mixture was heated at reflux for 4 hours. After the removal of solvent, the residue was partitioned between ethyl acetate and water. The organic layer was washed with brine, dried over magnesium sulfate and filtered. The filtrate was concentrated and the crude was recrystallized from ethyl acetate and hexane to give 2.28 g of the oxime (25%) as yellow crystals: mp (DSC) 174°–177° C. Anal. Calc'd. for $C_{18}H_{19}NOS$: C, 72.69; H, 6.44; N, 4.71; S, 10.78. Found: C, 72.52; H, 6.23; N, 4.58; S, 10.63.

Step 5. Preparation of 3-ethyl-4-(4-methylthiophenyl)-5-phenylisoxazole

To a solution of the oxime from Step 4 (2.21 g, 0.0074 mol) in 25 mL of tetrahydrofuran was added a solution of sodium bicarbonate (2.62 g, 0.031 mol) in 20 mL of water, followed by a solution of potassium iodide (4.56 g, 0.028 mol) and iodine (2.07 g, 0.0082 mol) in 30 mL of water. The reaction mixture was heated to reflux for 3 hours. After cooling, the mixture was treated with 100 mL of saturated aqueous potassium bisulfate solution and extracted with ethyl acetate. The organic layer was washed with brine, dried over magnesium sulfate and filtered. The filtrate was concentrated and the residue was purified by chromatography on silica gel (ethyl acetate/hexane, 5:95) to afford 2.1 g (96%) of the isoxazole as a brownish solid: mp (DSC) 85°–87 0° C. Anal. Calc'd. for $C_{18}H_{17}NOS$: C, 73.19; H, 5.80; N, 4.74; S, 10.85. Found: C, 73.03; H, 5.49; N, 4.55; S, 10.86.

Step 6. Preparation of 3-ethyl-4-(4-methylsulfonylphenyl)-5-phenylisoxazole

To a solution of the isoxazole from Step 5 (1.88 g, 6.4 mmol) in 50 mL of methanol was added a solution of OXONE® (7.82 g, 0.0127 mol) in 35 mL of water. The mixture was stirred at room temperature for 2 hours, then diluted with 500 mL of water. The precipitate was filtered and purified by chromatography on silica gel (ethyl acetate/acetone, 1:1) to give 1.73 g (83%) of 3-ethyl-4-(4-methylsulfonylphenyl)-5-phenylisoxazole as a white solid: mp (DSC) 130°–131° C. Anal. Calc'd. For $C_{18}H_{17}NO_3S$: C, 66.03; H, 5.23; N, 4.28; S, 9.79. Found: C, 66.07; H, 5.20; N, 4.28; S, 9.85.

EXAMPLE 30

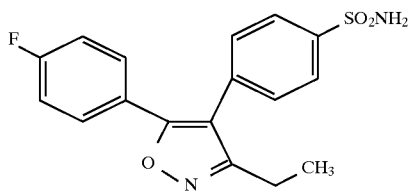

4-[3-Ethyl-5-(4-fluorophenyl)isoxazol-4-yl]benzenesulfonamide

Step 1. Preparation of 3-ethyl-5-(4-fluorophenyl)-4-phenylisoxazole

By substituting 4-fluorobenzaldehyde for benzaldehyde, and 1-phenyl-2-butanone for 1-(4-methylthiophenyl)-2-butanone in the method of Example 29 (Steps 3–5), the isoxazole was obtained as a yellow solid (9.5 g, 95%): mp 61°–63° C. Anal. Calc'd. for $C_{17}H_{14}FNO$: C, 76.39; H, 5.28; N, 5.24. Found: C, 75.75; H, 4.98; N, 5.06.

Step 2. Preparation of 4-[3-ethyl-5-(4-fluorophenyl)isoxazol-4-yl]benzenesulfonamide To the isoxazole from Step 1 (4.83 g, 0.018 mol) was added chlorosulfonic acid (20 mL) slowly at 0° C. The mixture was stirred at this temperature for 30 minutes and 3 hours at room temperature. The reaction mixture was added carefully to a cooled aqueous solution of ammonia hydroxide over 40 minutes. After stirring for 15 minutes, the mixture was extracted with ethyl acetate. The organic layer was washed with water, brine, dried over magnesium sulfate and filtered. The filtrate was concentrated and the residue was purified by chromatography on silica gel (ethyl acetate/hexane, 3:7) to give the sulfonamide as a white solid (3.5 g, 56%): mp (DSC) 171°–172° C. Anal. Calc'd. for $C_{17}H_{15}FN_2O_3S$: C, 58.95; H, 4.36; N, 8.09; S, 9.26. Found: C, 58.75; H, 4.43; N, 7.99; S, 9.42.

EXAMPLE 31

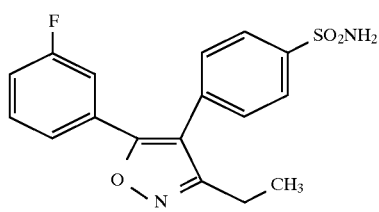

4-[3-Ethyl-5-(3-fluorophenyl)isoxazol-4-yl]benzenesulfonamide

This compound was made by the same procedure as described for Example 14: mp (DSC): 152°–154° C.; Anal. Calc'd. for $C_{17}H_{15}FN_2O_3S$: C, 58.95; H, 4.36; N, 8.09; S, 9.26. Found: C, 58.58; H, 4.39; N, 7.88; S, 9.27.

EXAMPLE 32

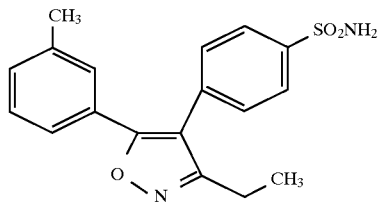

4-[3-Ethyl-5-(3-methylphenyl)isoxazol-4-yl]benzenesulfonamide

This compound was made by the same procedure as described for Example 14: mp (DSC): 80°–83° C.; Anal. Calc'd. for $C_{18}H_{18}N_2O_3S$: C, 63.14; H, 5.30; N, 8.18; S, 9.36. Found: C, 62.71; H, 5.25; N, 8.16; S, 9.56.

EXAMPLE 33

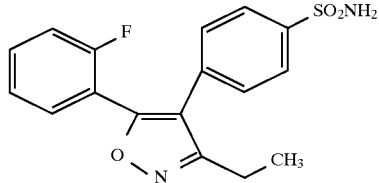

4-[3-Ethyl-5-(2-fluorophenyl)isoxazol-4-yl]benzenesulfonamide

This compound was made by the same procedure as described for Example 14: mp (DSC): 150°–151° C.; Anal.

Calc'd. for $C_{17}H_{15}FN_2O_3S$: C, 58.95; H, 4.36; N, 8.09; S, 9.26. Found: C, 58.88; H, 4.48; N, 8.01; S, 9.52.

EXAMPLE 34

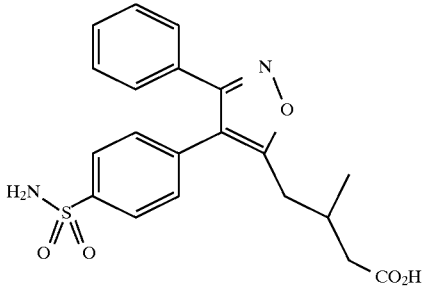

[4-[4-(Aminosulfonyl)phenyl]-3-phenylisoxazol-5-yl]-3-methylbutan-1-oic acid

Step 1. Preparation of 2-[4-aminosulfonylphenyl]-1-phenyl-ethan-1-one.

Chlorosulfonic acid (1781 g, 1018 mL, 15.29 mol) was treated portionwise with deoxybenzoin (400 g, 2.04 mol) at such a rate that the internal temperature was maintained between 5° and 15° C. The mixture was warmed to room temperature and maintained at that temperature for an additional 14 hours. The mixture was poured cautiously into ice water. The crude sulfonyl chloride was filtered and added portionwise to a solution of acetone (600 mL) and concentrated $NH_4OH$ (551 mL, 8.15 mol), yielding a pale yellow suspension. The crude precipitate was collected by vacuum filtration, and triturated with boiling acetone (1.5 L). Filtration afforded 2-[4-aminosulfonylphenyl]-1-phenyl-ethan-1-one (162 g, 29%) as an off-white powder: $^1H$ NMR (DMSO-$d_6$, 300 MHz) 8.05 (d, J=7.25 Hz, 2H), 7.76 (d, J=8.26 Hz, 2H), 7.65 (t, J=7.85 Hz, 1H), 7.54 (t, J=7.85 Hz, 2H), 7.44 (d, J=8.26 Hz, 2H), 7.30 (br s, 2H), 4.52 (s, 2H).

Step 2. Preparation of 2,5-dimethyl-1-[[4-(2-oxo-2-phenylethyl)phenyl]sulfonyl]-1H-pyrrole.

Thionyl chloride (25 mL, 0.34 mol) was added dropwise to ethanol (540 mL). The reaction was heated to reflux for 15 minutes and cooled. The solution was treated with 2-[4-aminosulfonylphenyl]-1-phenyl-ethan-1-one from Step 1 (20.0 g, 72.64 mmol) and acetonylacetone (12.8 mL, 108.96 mmol), and reheated to reflux for 30 minutes. After cooling to room temperature, the solution was poured into rapidly stirred saturated aqueous $Na_2CO_3$ and ice (1500 mL). The aqueous phase was extracted with ethyl acetate (2×700 mL). The combined organics were washed with brine, dried over $MgSO_4$, filtered and concentrated in vacuo, yielding a brown oil. The oil was diluted with ethyl acetate (200 mL) and hexane (2000 mL), dried with $MgSO_4$, gravity filtered, then purified through a short silica gel column with hexane and ethyl acetate (1:1) as eluant. The material was concentrated in vacuo and crystallized from hexane/ethyl acetate. The solid was isolated by filtration and air dried to afford 2,5-dimethyl-1-[[4-(2-oxo-2-phenylethyl)phenyl]sulfonyl]-1H-pyrrole (12.2 g, 49%) as a brown solid: mp 94.6°–98.8° C. $^1H$ NMR (DMSO-$d_6$/300 MHz) 8.05 (d, J=7.25 Hz, 2H), 7.76 (d, J=8.26 Hz, 2H), 7.65 (t, J=7.85 Hz, 1H), 7.54 (t, J=7.85 Hz, 1H), 7.44 (d, J=8.26 Hz, 2H), 7.30 ( br s, 2H), 4.52 (s, 2H). Mass spectrum: M+H obs. at m/z=354.

Step 3. Preparation of 2-[4-[N-[2,5-dimethylpyrrol]-sulfonyl]phenyl]-1-phenyl-ethan-1-one oxime.

2,5-Dimethyl-1-[[4-(2-oxo-2-phenylethyl)phenyl]sulfonyl]-1H-pyrrole from Step 2 (15.87 g, 46.48 mmol), hydroxylamine hydrochloride (6.46 g, 92.96 mmol) and sodium acetate (7.63 g, 92.96 mmol) were mixed and heated to reflux for 14 hours. Heating was discontinued and the solution was gravity filtered while still hot. The filtrate was diluted with water (10 mL) and material crystallized. The oxime was isolated by filtration to give 2-[4-[N-[2,5-dimethylpyrrol]-sulfonyl]phenyl]-1-phenyl-ethan-1-one oxime as a fluffy tan solid (13.65 g, 80%): mp 123.2°–125.7° C. $^1H$ NMR (CDCl$_3$/300 MHz 7.73 (br s, 1H), 7.64–7.50 (m, 4H), 7.39–7.32 (m, 5H), 5.84 (s, 2H), 4.23 (s, 2H), 2.36 (s, 6H). Anal. Calc'd for $C_{20}H_{20}N_2O_3S$. 3.66% $H_2O$: C, 62.81; H, 5.68; N, 7.32. Found: C, 62.78; H, 5.25; N, 7.25.

Step 4. Preparation of [4-[4-[N-[2,5-dimethylpyrrol]sulfonyl]phenyl]]-3-phenylisoxazol-5-yl]-3-methylbutan-1-oic acid.

A stirred, chilled (0° C.) solution of diisopropylamine (4.64 mL, 35.42 mmol) in THF (20 mL) was treated with n-butyllithium (6.20 mL of 10.0M in hexanes, 35.42 mmol) via syringe over 5 minutes. The solution was stirred at 0° C. for 15 minutes, yielding a ca. 1.8M solution of LDA in THF and hexanes. A chilled (−78° C.), solution of 2-[4-[N-[2,5-dimethylpyrrol]-sulfonyl]phenyl]-1-phenyl-ethan-1-one oxime from Step 3 (3.97 g, 10.77 mmol) in THF (40 mL) was treated with the LDA stock solution (15.0 mL, 27.0 mmol) via syringe. The reaction was stirred at −78° C. for 20 minutes, warmed to −5° C., then chilled to −78° C. again. To this dark solution was added 3-methyl glutaric anhydride (2.07 g, 16.16 mmol). The cooling bath was removed, and the reaction was warmed to room temperature for 2 hours. Saturated $NH_4Cl$ and concentrated HCl were added until pH <2 was obtained. The reaction was extracted with ethyl acetate. The combined organic phases were washed with $KHSO_4$ solution (0.25M) and brine, dried over $MgSO_4$, filtered and concentrated. The crude material was purified by flash chromatography (hexane/ethyl acetate (1:1) with 2% acetic acid), yielding [4-[4-[N-[2,5-dimethylpyrrol]-sulfonyl]phenyl]]-3-phenylisoxazol-5-yl]-3-methylbutan-1-oic acid as a brown foam (2.40 g) which was utilized without further purification.

Step 5. Preparation of [4-[4-(aminosulfonyl)phenyl]-3-phenylisoxazol-5-yl]-3-methylbutan-1-oic acid The [4-[4-[N-[2,5-dimethylpyrrol]-sulfonyl]phenyl]]-3-phenylisoxazol-5-yl]-3-methylbutan-1-oic acid from Step 4 was dissolved in trifluoroacetic acid (20 mL) and water (7 mL) and heated to reflux for 6 hours. The reaction was cooled to room temperature, concentrated under high vacuum, diluted with ethanol and concentrated in vacuo, yielding a black oil. The crude material was dissolved in $NaHCO_3$ solution (pH adjusted to 12 with 1N NaOH solution) and washed with ether. The resulting aqueous phase was acidified to pH 2 with concentrated HCl, and extracted with dichloromethane/ethyl acetate (1:1). The combined organic phases were dried over $MgSO_4$, filtered and concentrated in vacuo, yielding a dark brown oil. This crude material was partially purified by passing through a plug of silica gel using hexane/ethyl acetate (1:1) with 2% acetic acid as eluant, yielding a clear oil. Trituration of the oil with dichloromethane yielded, upon collection by vacuum filtration, [4-[4-(aminosulfonyl)phenyl]-3-phenylisoxazol-5-yl]-3-methylbutan-1-oic acid (0.219 g, 5%) as an off-white solid: mp 147.9°–149.0° C. $^1H$ NMR (CDCl$_3$ with DMSO-$d_6$/300 MHz) δ7.80 (d, J=8.46 Hz, 2H), 7.30–7.14 (m, 9H), 6.35 (s, 2H), 2.88–2.55 (m, 2H), 2.40–2.20 (m, 2H), 2.09–2.04 (m, 1H), 0.90 (d, J=6.85 Hz, 3H). Mass spectrum M+H obs at m/z 401. High resolution mass spectrum calc'd. 401.1171. Found: 401.1174.

EXAMPLE 35

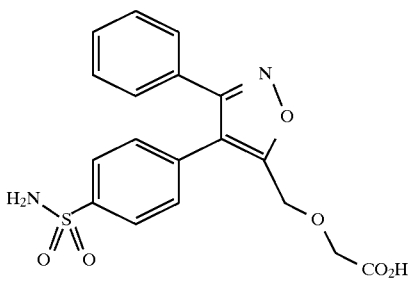

[[4-[4-(Aminosulfonyl)phenyl]-3-phenylisoxazol-5-yl]-methoxy]acetic acid

Step 1. Preparation of 5-[4-[4-[N-[2,5-dimethylpyrrol]-sulfonyl]phenyl]-3-phenylisoxazol-5-yl]-methyloxyacetic acid.

A solution of 2,5-dimethyl-1-[[4-(2-oximino-2-phenylethyl)phenyl]sulfonyl]-1H-pyrrole (Example 34, Step 3) (5.19 g, 14.09 mmol) in tetrahydrofuran (90 mL) was chilled to −78° C. and treated with LDA (22.0 mL, 30.99 mmol in THF) via syringe. After stirring for 30 minutes, the dry ice bath was removed and the reaction was warmed to 0° C. over 40 minutes. The solution was chilled to −78° C. and diglycolic acid anhydride (1.80 g, 15.50 mmol) in THF (10 mL) was added via syringe. The reaction was warmed to room temperature and stirred for 2 hours. The reaction was quenched with saturated $NH_4Cl$ solution and concentrated HCl was added to pH 1. The layers were separated and the aqueous layer was extracted with dichloromethane. The combined organic phases were washed with brine, dried over $MgSO_4$, filtered and concentrated in vacuo, yielding a dark brown oil. This oil was purified by flash chromatography using hexane/ethyl acetate (1:1) (with 2% acetic acid) as the eluant, yielding a brown foam (3.035 g, 45%). The brown foam was dissolved in THF (50 mL) and treated with concentrated $H_2SO_4$ (2 mL). The solution was heated to reflux for 1 hour, cooled to room temperature, poured into ice and extracted with dichloromethane. The combined organic phases were washed with $KHSO_4$ solution (0.25M), dried over $MgSO_4$, filtered and concentrated, yielding 5-[4-[4-[N-[2,5-dimethylpyrrol]sulfonyl]phenyl]-3-phenylisoxazol-5-yl]]-methyloxyacetic acid as a brown foam (2.28 g, 35%): $^1$H NMR ($CDCl_3$/300 MHz) 7.66 (d, J=8.57 Hz, 2H), 7.47–7.35 (m, 7H), 5.88 (s, 2H), 4.71 (s, 2H), 4.26 (s, 2H), 2.39 (s, 6H). Mass spectrum M+H obs at m/z 467. High resolution mass spectrum: calc'd. 467.1277. Found: 467.1268. Anal. Calc'd for $C_{24}H_{22}N_2O_6S$: C, 61.79; H, 4.75; N, 6.00. Found: C, 62.32; H, 5.07; N, 5.82.

Step 2. Preparation of [4-[4-(aminosulfonyl)phenyl]-3-phenylisoxazol-5-yl]-O-methylglycolic acid.

5-[4-[4-[N-[2,5-Dimethylpyrrol]sulfonyl]phenyl]-3-phenylisoxazol-5-yl]]-methyloxyacetic acid from Step 1 (1.097 g, 2.35 mmol) was dissolved in a mixture of TFA (12 mL) and water (4 mL) and heated to 60° C. for 6 hours. The clear brown solution was cooled to room temperature and concentrated under high vacuum, yielding a solid. The solid was dissolved in ethyl acetate, washed with aqueous $KHSO_4$ solution (0.25M), and with brine, dried over $MgSO_4$, filtered, decolorized with carbon, and heated to gentle reflux. The suspension was cooled to room temperature, filtered through diatomaceous earth, and concentrated in vacuo, yielding a brown solid. This solid was dissolved in a minimum of aqueous $NaHCO_3$ solution and washed with ethyl acetate. The resulting aqueous solution was acidified with concentrated HCl to pH 2, causing the formation of a precipitate. This precipitate was collected by vacuum filtration, yielding 5-[[4-[4-(aminosulfonyl)phenyl]-3-phenylisoxazol-5-yl]-methyloxy]acetic acid (0.94 g, 100%) as a tan powder: mp 186.7°–191.5° C. $^1$H NMR (DMSO-$d_6$/300 MHz) 13.5–12.0 (br s, 1H), 7.82 (d, J=8.46 Hz, 2H), 7.50–7.33 (m 9H), 4.68 (s, 2H), 4.13 (s, 2H). Mass spectrum (M+H obs at m/z 389). High resolution mass spectrum calc'd.: 388.0729. Found: 388.0722. Anal. Calc'd. for $C_{18}H_{16}N_2O_6S$ 0.94% $H_2O$: C, 55.14; H, 4.22; N, 7.14. Found: C, 55.16; H, 4.06; N, 6.33.

EXAMPLE 36

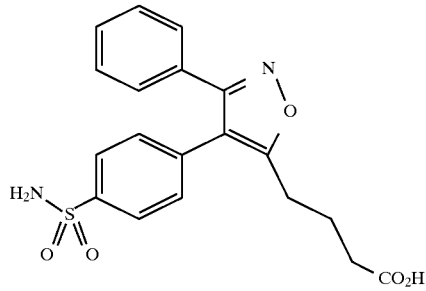

4-[4-[4-(Aminosulfonyl)phenyl]]-3-phenylisoxazol-5-yl]butanoic acid

Step 1. Preparation of 4-[4-[4-N-[2,5-dimethylpyrrol]-sulfonyl]phenyl]]-3-phenylisoxazol-5-yl]butan-1-oic acid.

A solution of 2,5-dimethyl-1-[[4-(2-oximino-2-phenylethyl)phenyl]sulfonyl]-1H-pyrrole (Example 34, Step 3) (6.21 g, 16.85 mmol) in THF (100 mL) was chilled (−78° C.) and treated with n-butyllithium (23.17 mL, 37.08 mmol) via syringe. The reaction was warmed to 0° C., cooled back to −40° C., and treated with a solution of one equivalent of glutaric anhydride in THF (5 mL). The solution was warmed to room temperature and maintained at this temperature for 2 hours. The crude reaction was quenched with saturated $NH_4Cl$ and concentrated HCl was added until the pH was 2. The resulting mixture was extracted with ethyl acetate and the combined organic phases were washed with brine, dried over $MgSO_4$, filtered, and concentrated in vacuo, yielding a brown oil. A solution of the brown oil (3.10 g) in THF (50 mL) was treated with concentrated $H_2SO_4$ (2 mL) and heated to reflux for 2 hours. The reaction was cooled to room temperature, diluted with brine and the layers separated. The aqueous phase was extracted with ethyl acetate, and the organic phases were combined. The combined phases were washed with water until the washes were pH 5 or higher. The organic phase was dried over $MgSO_4$, filtered, and concentrated in vacuo, yielding a brown oil. This oil was purified by flash chromatography using hexane/ethyl acetate (3:1) (with 22% acetic acid), yielding the 4-[4-[4-[N-[2,5-dimethylpyrrol]-sulfonyl]phenyl]]-3-phenylisoxazol-5-yl]butan-1-oic acid (1.327 g, 17% based upon oxime) as a tan foam, which was suitable for use without further purification: $^1$H NMR ($CDCl_3$/300 MHz) 7.65 (d, J=8.66 Hz, 2H), 7.43–7.25 (m, 7H), 5.88 (s, 2H), 2.88 (t, J=8.4 Hz, 2H), 2.48–2.37 (m, 8H), 2.18–2.02 (m, 2H).

Step 2. Preparation of 4-[4-[4-(aminosulfonyl)phenyl]]-3-phenylisoxazol-5-yl]butanoic acid.

4-[4-[4-[N-[2,5-Dimethylpyrrol]-sulfonyl]phenyl]]-3-phenylisoxazol-5-yl]butan-1-oic acid from Step 1 (1.27 g, 2.734 mmol) was dissolved in TFA (20 mL) and water 6.7 mL), and heated to 72° C. for 7 hours. The reaction was concentrated under high vacuum using toluene to chase trace TFA. The crude product was dissolved in a minimum of aqueous NaHCO₃ and washed with ether. The resulting aqueous phase was acidified with concentrated HCl, yielding a precipitate which was isolated by filtration to afford 4-[4-[4-(aminosulfonyl)phenyl]]-3-phenylisoxazol- 5-yl] butan-1-oic acid (0.756 g, 72%) as a powder: mp 203.8°–206.9° C. $^1$H NMR (DMSO-d$_6$/300 MHz) 12.13 (br s, 1H), 7.82 (d, J=8.46 Hz, 2H), 7.50–7.25 (m, 9H), 2.82 (t, J=7.45 Hz, 2H), 2.28 (t, J=7.25 Hz, 2H), 1.95–1.75 (m, 2H). Anal. Calc'd. for C$_{19}$H$_{18}$N$_2$O$_5$S: C, 59.06; H, 4.70; N, 7.25. Found: C, 59.10; H, 4.78; N, 7.18.

EXAMPLE 37

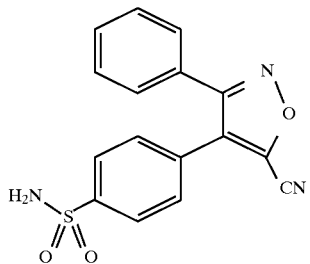

4-[5-Cyano-3-phenylisoxazol-4-yl] benzenesulfonamide

Step 1. Preparation of [4-[4-[N-2,5-dimethylpyrrol] sulfonyl]phenyl]-3-phenylisoxazol-5-yl]carboxylic acid.

To a chilled (−78° C.), stirred solution of 2,5-dimethyl-1-[[4-(2-oximino-2-phenylethyl)phenyl]sulfonyl]-1H-pyrrole (Example 34, Step 3) (6.41 g, 17.40 mmol) in THF (100 mL) was added freshly prepared LDA in THF/hexane [made from n-butyllithium (3.8 mL, 10.0M in hexanes and diisopropylamine (5.02 mL, 38.27 m=ol) in THF (25 mL)]. The resulting dark solution was stirred at −78° C. for 30 minutes, warmed to 0° C. over 40 minutes and chilled to about −25° C. Dimethyl oxalate (2.88 g, 24.36 mmol) in THF (5 mL) was added via syringe. The resulting solution was warmed to room temperature and stirred for 2 hours. The reaction was quenched with saturated NH₄Cl solution, followed by the addition of sufficient concentrated HCl to adjust the pH to 2. The layers were separated and the aqueous phase was extracted with ethyl acetate. The organic layers were combined and washed with KHSO₄ (0.25M aqueous solution) and brine, dried over MgSO₄, filtered and concentrated in vacuo. The resulting crude material was purified by passage through a silica plug using ethyl acetate as the eluant. Upon concentration in vacuo, [4-[4-[N-2,5-dimethylpyrrol]sulfonyl]phenyl]-3-phenylisoxazol-5-yl] carboxylic acid was obtained as a brown foam (6.021 g) and was of sufficient purity to be used without further purification: Mass spectrum: M+H obs. at m/z 423. Anal. Calc'd for C$_{22}$H$_{18}$N$_2$O$_5$S.0.55% H$_2$O: C, 62.20; H, 4.33; N, 6.59. Found: C, 62.28; H, 4.78; N, 6.32.

Step 2. Preparation of methyl [4-[4-[N-2,5-dimethylpyrrol] sulfonyl]-phenyl]-3-phenylisoxazol-5-yl]carboxylate.

[4-[4-[N-2,5-Dimethylpyrrol]sulfonyl]phenyl]-3-phenylisoxazol-5-yl]carboxylic acid from Step 1 (4.99 g) was dissolved in TFA (75 mL) and water (25 mL) and heated to 50° C. for 11 hours. The reaction was cooled to room temperature and concentrated under high vacuum to yield a brown solid. A portion of the solid (3.75 g) was added to a freshly prepared solution of SOCl$_2$ (13 mL) in methanol (250 mL). The reaction was heated to reflux for 2 hours, cooled to room temperature and concentrated in vacuo, yielding a black solid. This crude material was purified by flash chromatography using hexane/ethyl acetate (2:1 gradient to 1:1 ratio), yielding methyl [4-[4-[N-2,5-dimethylpyrrol]sulfonyl]phenyl]-3-phenylisoxazol-5-yl] carboxylate (1.30 g, 25%) as a green oil, and was sufficiently pure to be used without further purification: $^1$H NMR (CDCl$_3$/300 MHz) 7.65 (d, J=8.46 Hz, 2H), 7.42 (d, J=8.46 Hz, 3H), 7.38–7.26 (m, 4H), 5.88 (s, 2H), 3.90 (s, 3H), 2.39 (s, 6H).

Step 3. Preparation of [4-[4-[N-2,5-dimethylpyrrol] sulfonyl]phenyl]-3-phenylisoxazol-5-yl]carboxamide Ammonia gas was added to a solution of methyl [4-[4-[N-2,5-dimethylpyrrol]sulfonyl]phenyl]-3-phenylisoxazol-5-yl]carboxylate from Step 2 (1.25 g, 2.86 mmol) in THF (5 mL) and EtOH (10 mL) at 5° C. for 20 minutes. The vessel was sealed and stirred at room temperature for 60 hours (pressure was 23 psi). The reaction was carefully vented and concentrated in vacuo, and the crude material was crystallized from ethyl acetate/isooctane and collected by vacuum filtration, yielding [4-[4-[N-2,5-dimethylpyrrol]sulfonyl] phenyl]-3-phenylisoxazol-5-yl]carboxamide (96 mg, 80%) as a tan powder: mp 196° C. (dec). $^1$H NMR (DMSO-d$_6$/300 MHz) 8.44 (br s, 1H), 8.04 (br s, 1H), 7.71 (d, J=8.46 Hz, 2H), 7.51 (d, J=8.46 Hz, 2H), 7.49–7.41 (m, 1H), 7.37 (t, J=7.65 Hz, 2H), 7.22 (d, J=8.46, 2H), 5.96 (s, 2H), 2.30 (s, 6H).

Step 4. Preparation of [4-[4-aminosulfonyl]phenyl]-3-phenylisoxazol-5-yl]carboxamide.

[4-[4-[N-2,5-Dimethylpyrrol]sulfonyl]phenyl]-3-phenylisoxazol-5-yl]carboxamide from Step 3 (0.692 g, 1.64 mmol) was dissolved in TFA (15 mL) and water (5 mL) and the solution was heated to 81° C. for 6 hours.

The solution was cooled to room temperature and concentrated under high vacuum to yield a brown solid. This solid was triturated with ethyl acetate and the solid was collected by vacuum filtration, yielding [4-[4-aminosulfonyl]phenyl]-3-phenylisoxazol-5-yl]carboxamide (0.388 g, 69%) as a gray powder: mp 263.7°–278.6° C. $^1$H NMR (DMSO-d$_6$/300 MHz) 8.40 (br s, 1H), 8.03 (s, 1H), 7.77 (d, J=8.26 Hz, 2H), 7.45–7.28 (m, 9H).

Step 5. Preparation of 4-[5-cyano-3-phenylisoxazol-4-yl] benzenesulfonamide.

A stirred suspension of [4-[4-aminosulfonyl]phenyl]-3-phenylisoxazol-5-yl]carboxamide from Step 4 (0.307 g, 0.894 mmol) in POCl$_3$ (5 mL) was heated to 105° C. for 5 hours. The reaction was cooled to room temperature and concentrated under high vacuum. Toluene was added and the mixture was reconcentrated. The resulting solid was passed through a silica plug using ethyl acetate as eluant. The eluant was washed with NaHCO$_3$ solution, KHSO$_4$ solution, and with brine, dried over MgSO$_4$, filtered and concentrated in vacuo, yielding 4-[5-cyano-3-phenylisoxazol-4-yl] benzenesulfonamide as a tan powder (0.204 g, 70%): mp 218.0°–219.4° C. $^1$H NMR (DMSO-d$_6$/300 MHz) 7.93 (d, J=8.26, 2H), 7.61 (d, J=8.26, 2H), 7.57–7.40 (m, 7H). Anal. Calc'd. for C$_{16}$H$_{11}$N$_3$O$_3$S: C, 59.07; H, 3.41; N, 12.92. Found: C, 59.01; H, 3.65; N, 12.44.

EXAMPLE 38

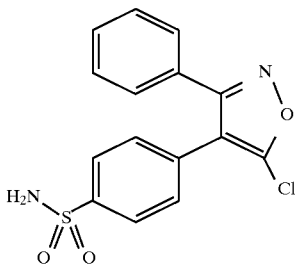

4-[5-Chloro-3-phenylisoxazol-4-yl]benzenesulfonamide

Phosphorus oxychloride (15 mL) was added to a mixture of 4-[5-hydroxy-3-phenylisoxazol-5-yl]benzenesulfonamide (Example 12) (1.117 g, 3.53 mmol) and triethylamine (0.73 mL, 0.53 g, 5.30 mmol), and heated to 70° C. for 5 hours. After cooling to room temperature, the reaction was concentrated in vacuo. Toluene was added and the resulting solution was concentrated in vacuo, yielding a brown oil. The oil was dissolved in ethyl acetate (50 mL) and washed with 1N HCl solution and with brine, dried over MgSO$_4$, filtered and concentrated in vacuo, yielding 4-[5-chloro-3-phenylisoxazol-4-yl]benzenesulfonamide as a brown solid (0.943 g, 84%): mp 186.1°–187.4° C. $^1$H NMR (CDCl$_3$ with CD$_3$CN) 7.85 (d, J=8.46 Hz, 2H), 7.40–7.25 (m, 9H). Mass spectrum M+H obs at m/z 335. High resolution mass spectrum calc'd. for C$_{15}$H$_{12}$ClN$_2$O$_3$S (M+H): 335.0274. Found: 335.0271.

EXAMPLE 39

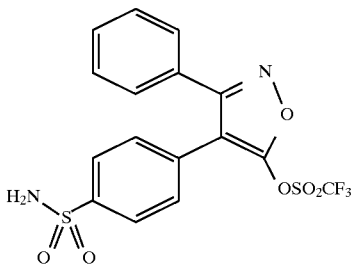

4-[5-Trifluoromethansulfonoxy-3-phenylisoxazol-4-yl]benzenesulfonamide

A suspension of 4-[5-hydroxy-3-phenylisoxazol-4-yl]benzenesulfonamide (Example 12) (0.275 g, 0.869 mmol), pyridine (0.077 mL, 0.076 g, 0.956 mmol), and DMAP (0.011 g, 0.087 mmol) in dichloromethane was chilled to −78° C., and treated via syringe with trifluoromethanesulfonic anhydride (0.160 mL, 0.270 g, 0.956 mmol). The reaction was stirred for 1 hour at −78° C., and for 3 hours at room temperature. The resulting mixture was washed with NaHCO$_3$ solution, and with aqueous KHSO$_4$, dried over MgSO$_4$, filtered and concentrated in vacuo, yielding a tan semi-solid. This material was purified by flash chromatography, yielding 4-[5-trifluoromethansulfonoxy-3-phenylisoxazol-4-yl]benzenesulfonamide (0.123 g, 32%) as a white crystalline solid: mp 129.9°–135.3° C. $^1$H NMR (DMSO-d$_6$) 7.70 (d, J=8.26 HZ,. 2H), 7.65–7.35 (m, 7H), 7.31 (br s, 2H). $^{19}$F NMR (DMSO-d$_6$) 74.19. Mass spectrum m+H obs at m/z 449. High resolution mass spectrum calc'd. for C$_{16}$H$_{12}$F$_3$N$_2$O$_6$S$_2$ (M+H): 449.0089. Found: 449.0084.

EXAMPLE 40

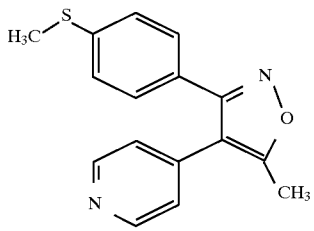

[5-Methyl-3-(4-methylthiophenyl)isoxazol-4-yl]-4-pyridine

Step 1. Preparation of 1-(4-thiomethylphenyl)-2-(4-pyridyl)-ethan-1-one.

Methyl 4-(methylthio)benzoate (8.77 g, 48 mmol), 4-picoline (4.47 g, 48 mmol), and dimethoxy ethyl ether (150 mL) were stirred at room temperature, and sodium hydride (60% in glycerine) (5.76 g, 144 mmol) was added. The mixture was heated to reflux for 72 hours, poured into ice water, and extracted with ethyl acetate (3×100 mL). The combined organics were washed with water (2×50 mL) and dried over MgSO$_4$. Hexanes were slowly added until a yellow solid precipitated which was collected by filtration (4.1 g, 35%): $^1$H NMR (DMSO-d$_6$/300 MHz) 8.5 (d, J=4.4 Hz, 2H), 7.9 (d, J=8.5 Hz, 2H), 7.4 (d, J=8.3 Hz, 2H), 7.3 (d, J=4.4 Hz, 2H), 4.4 (s, 2H), 2.5 (s, 3H).

Step 2. Preparation of 1-(4-thiomethylphenyl)-2-(4-pyridyl)-ethan-1-one-oxime.

1-(4-Thiomethylphenyl)-2-(4-pyridyl)-ethan-1-one from Step 1 (3.0 g, 12 mmol) and hydroxylamine hydrochloride (0.9 g, 13 mmol) were dissolved in ethanol (150 mL) and heated to reflux overnight. The mixture was cooled, water was added, and the solution was extracted with ethyl acetate (2×100 mL). The combined extract was washed with water (2×50 mL), dried over MgSO$_4$, and concentrated. The material was recrystallized from ethyl acetate/hexanes to afford a yellow solid (3.1 g) which was used in the next step without further purification or characterization.

Step 3. Preparation of 4-[5-methyl-5-hydroxy-4-(4-pyridyl)isoxazoline-3-yl]thioanisole.

1-(4-Thiomethylphenyl)-2-(4-pyridyl)-ethan-1-one-oxime from Step 2 (3.0 g, 12 mmol) was dissolved in tetrahydrofuran (150 mL) and cooled to −78° C. under nitrogen. Lithium diisopropylamide (2.0M solution in heptane/tetrahydrofuran/ethylbenzene, 13.2 mL, 26.4 mmol) was added dropwise maintaining the temperature below −65° C. After stirring for 0.5 hour, acetic anhydride (3.68 g, 36 mmol) was added. The reaction mixture was slowly warmed to −30° C. and poured into ice water. The resulting aqueous solution was extracted with ethyl acetate (3×50 mL). The combined extract was washed with brine and with water, and dried over MgSO$_4$. The resulting crude material was used in the next step without further purification or characterization.

Step 4. Preparation of 4-[5-methyl-4-(4-pyridyl)isoxazol-3-yl]thioanisole.

Sulfuric acid (30 mL) was cooled to −78° C. and 4-[5-methyl-5-hydroxy-4-(4-pyridyl)isoxazoline-3-yl]thioanisole from Step 3 (3.2 g, 11 mmol) was added. The cooling bath was removed and the mixture was stirred for 1 hour, and poured into ice water. The mixture was diluted with dichloromethane (50 mL) and treated with solid NaHCO$_3$ until the mixture was neutral to pH paper. This solution was extracted with dichloromethane (3×50 mL). The combined extract was washed with water, dried over MgSO$_4$ and concentrated. The crude product was purified by flash chromatography, eluting with ethyl acetate:hexane (1:1). The appropriate fractions were concentrated and recrystallized from ethyl acetate/hexane to yield a yellow solid (0.4 g, 7.5%): mp 120.6°–125.5° C. $^1$H NMR (CDCl$_3$/300 MHz) 8.6 (d, J=5.4 Hz, 2H), 7.3 (d, J=8.7 Hz, 2H), 7.2 (d, J=8.7 Hz, 2H), 7.1 (d, J=6.0 Hz, 2H), 2.5 (s, 3H). High resolution mass spectrum calc'd. for C$_{16}$H$_{15}$N$_2$SO(M+H): 283.0905. Found: 283.0861.

EXAMPLE 41

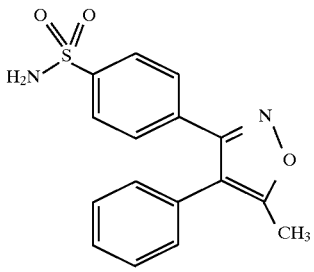

4-[5-Methyl-4-phenylisoxazol-3-yl]
benzenesulfonamide

Step 1. Preparation of 1-(4-bromophenyl)-2-phenylethan-1-one.

4-Bromobenzaldehyde (10.0 g, 54 mmol), dichloromethane (100 mL), and zinc iodide (5 mg) were stirred at 0° C. under nitrogen and treated with trimethylsilylcyanide (5.95 g, 60 mmol) dropwise. The reaction was stirred for 16 hours, then water (5 mL) was added dropwise. The mixture was washed with brine (2×30 mL), dried over MgSO$_4$, and concentrated under high vacuum. The resulting oily residue was dissolved in tetrahydrofuran (150 mL) and cooled to −78° C. under nitrogen. Lithium diisopropylamide (2.0M solution in heptane/tetrahydrofuran/ethylbenzene, 30 mL, 60 mmol) was added dropwise, maintaining the temperature below −60° C. This solution was stirred for 0.5 hour then treated with benzyl bromide (10.26 g, 60 mmol). The solution was warmed to −15° C. and poured into a stirred solution of 1N hydrochloric acid (150 mL) and trifluoroacetic acid (10 mL). After stirring for 1 hour, the mixture was extracted with ethyl acetate (2×50 mL). The combined extract was washed with brine (2×50 mL) and concentrated. The resulting dark oily residue was treated with 2.5N sodium hydroxide, filtered and recrystallized from acetone/ethanol/water to afford a light brown solid (11.5 g, 77%): mp 111.4–111.5.

Step 2. Preparation of 1-(4-bromophenyl)-2-phenyl-ethan-1-one oxime.

1-(4-Bromophenyl)-2-phenyl-ethan-1-one from Step 1 (10.16 g, 37 mmol), ethanol (100 mL), water (50 mL), hydroxylamine hydrochloride (5.14 g, 74 mmol), and sodium acetate (10.07 g, 74 mmol) were combined and heated to 75° C. for 2 hours. The mixture was added to water (100 mL) and the precipitated oxime was isolated by filtration to afford a yellow solid (7.07 g, 66%): mp 136.5°–136.9° C.

Step 3. Preparation of 4-[5-methyl-4-phenylisoxazol-3-yl] bromobenzene.

1-(4-Bromophenyl)-2-phenyl-ethan-1-one oxime from Step 2 (5.8 g, 20 mmol) and tetrahydrofuran (150 mL) were stirred at −78° C. under nitrogen. Lithium diisopropylamide (2.0M solution in heptane/tetrahydrofuran/ethylbenzene, 22 mL, 22 mmol) was added dropwise, maintaining the temperature below −50° C. The solution was warmed to −30° C. and treated with N-acetyl imidazole (2.42 g, 22 mmol). The mixture was stirred until the temperature reached 0° C. The solution was poured into 1N hydrochloric acid (50 mL), extracted with ethyl acetate (100 mL) and the layers separated. The organic layer was washed with brine (2×50 mL), dried over MgSO$_4$ and concentrated. The resulting mixture was purified by flash column chromatography, eluting with ethyl acetate:hexane (1:4). After the appropriate fractions were concentrated, the material was dissolved in methanol and a crystal of p-toluenesulfonic acid was added. After heating to reflux for 16 hours, the mixture was concentrated and recrystallized from ethanol/water. A white solid was collected by filtration (3.8 g, 60%): mp 108.1°–108.7° C. $^1$H NMR (acetone-d$_6$/300 MHz) 7.6 (d, J=8.4 Hz, 2H), 7.4 (m, 5H), 7.3 (m, 2H), 2.4 (s, 3H). Anal. Calc'd. for C$_{16}$H$_{12}$BrNO: C, 61.17; H, 3.85; N, 4.46. Found: C, 61.07; H, 3.88; N, 4.45.

Step 4. Preparation of 4-[5-methyl-4-phenylisoxazol-3-yl] benzenesulfonamide.

4-[5-Methyl-4-phenylisoxazol-3-yl]bromobenzene from Step 3 (1.73 g, 5.5 mmol) and tetrahydrofuran (100 mL) were stirred at −78° C. under nitrogen. Butyllithium (1.6M in hexanes, 4.1 mL, 6.6 mmol) was added dropwise, maintaining the temperature below −60° C. After stirring at −78° C. for 0.5 hour, sulfur dioxide gas was passed through a stainless steel needle above the surface of the solution. After 1 minute, the solution changed color from orange to clear, and after 10 minutes pH paper indicated an acidic reaction. Gas addition was ceased and the cooling bath was removed. After 1 hour, the mixture was concentrated to 25 mL and hexane (100 mL) was added. A white precipitate formed which was isolated by filtration. This solid was dissolved in water (50 mL) and sodium acetate (4.5 g, 55 mmol), and hydroxylamine-O-sulfonic acid (0.75 g, 6.6 mmol) were added. The resulting mixture was stirred at room temperature overnight and extracted with ethyl acetate (2×50 mL). The combined extract was washed with brine, dried over MgSO$_4$, and concentrated. A white solid was recrystallized from dichloromethane/hexane (0.8 g, 46%): mp 150.9°–152.3° C. $^1$H NMR (acetone-d$_6$/300 MHz) 7.9 (d, J=9.7 Hz, 2H), 7.6 (d, J=9.7 Hz, 2H), 7.4 (m, 3H), 7.3 (m, 2H), 6.7 (bs, 2H), 2.5 (s, 3H). Anal. Calc'd. for C$_{16}$H$_{14}$N$_2$O$_3$S: C, 61.13; H, 4.49; N, 8.91. Found: C, 61.18; H, 4.52; N, 8.85. High resolution mass spectrum calc'd. (M+H): 315.0803. Found : 315.0793.

EXAMPLE 42

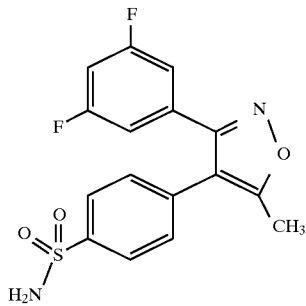

4-[3-(3,5-Difluorophenyl)-5-methylisoxazol-4-yl]
benzenesulfonamide

Step 1. Preparation of 1-(3,5-difluorophenyl)-2-phenyl-ethan-1-one.

3,5-Difluorobenzaldehyde (10.0 g, 70 mmol), dichloromethane (100 mL) and zinc iodide (5 mg) were stirred at 0° C. under nitrogen. Trimethylsilylcyanide (7.64 g, 77 mmol) was added dropwise with a slight exotherm. The reaction proceeded for 16 hours, then water (5 mL) was added dropwise. The mixture was washed with brine (2×30 mL), dried over MgSO$_4$, and concentrated under high vacuum. The resulting oily residue was dissolved in tetrahydrofuran (150 mL) and cooled to −78° C. under nitrogen. Lithium diisopropylamide (2.0M solution in heptane/tetrahydrofuran/ethylbenzene, 38.5 mL, 77 mmol) was added dropwise, maintaining the temperature below −60° C. The solution was stirred for 0.5 hour, and benzyl bromide (13.17 g, 77 mmol) was added. The cooling bath was removed and the mixture was stirred until the temperature reached −15° C. when the mixture was poured into a stirred solution of 1N hydrochloric acid (150 mL) and trifluoroacetic acid (10 mL). After stirring for one hour, the mixture was extracted with ethyl acetate (2×50 mL). The combined extract was washed with brine (2×50 mL) and concentrated. The resulting dark oily residue was treated with 2.5N sodium hydroxide and extracted with ether (3×50 mL). The combined extract was washed with water and dried over MgSO$_4$. The solution was concentrated and the residue crystallized from ether/hexane to afford a yellow solid (15.0 g, 92%). This material was used in the next step without further purification or characterization.

Step 2. Preparation of 1-(3,5-difluorophenyl)-2-phenyl-ethan-1-one oxime.

1-(3,5-Difluorophenyl)-2-phenyl-ethan-1-one from Step 1 (5.00 g, 21.6 mmol), ethanol (110 mL), water (30 mL), hydroxylamine hydrochloride (3.00 g, 43.1 mmol), and sodium acetate (5.87 g, 43.1 mmol) were combined and heated to 75° C. for 2 hours. The mixture was added to water (100 mL), the material separated and was isolated by filtration to afford a yellow solid (2.1 g, 39%). This material was used in the next step without further purification or characterization.

Step 3. Preparation of 3-(3,5-difluorophenyl-4-phenyl-5-methyl isoxazole.

1-(3,5-Difluorophenyl)-2-phenyl-ethan-1-one oxime from Step 2 (1.9 g, 7.7 mmol) and tetrahydrofuran (100 mL) were stirred at −78° C. under nitrogen. Lithium diisopropylamide (2.0M solution in heptane/tetrahydrofuran/ethylbenzene, 9.5 mL, 19 mmol) was added dropwise, maintaining the temperature below −50° C. The solution was warmed to −20° C., N-acetyl imidazole (1.06 g, 9.6 mmol) was added, and the reaction was maintained at −20° C. for an additional hour. The solution was poured into 1N hydrochloric acid (50 mL), extracted with ethyl acetate (100 mL) and the layers separated. The organic layer was washed with brine (2×50 mL), dried over MgSO$_4$, and concentrated. The resulting mixture was purified by flash column chromatography, eluting with ethyl acetate:hexane (1:4). After the appropriate fractions were concentrated, the material was dissolved in methanol and p-toluenesulfonic acid (10 mg) was added. The solution was heated to reflux for 16 hours, and concentrated in vacuo. The residue was dissolved in ethyl acetate, washed with saturated aqueous NaHCO$_3$ and with water, dried over MgSO$_4$ and concentrated to afford a light brown oil (1.3 g, 62%). This material was used without further purification or characterization.

Step 4. Preparation of 4-[5-methyl-3-(3,5-difluorophenyl)isoxazol-4-yl]benzenesulfonamide.

Chlorosulfonic acid (40 mL) was cooled to −78° C. and treated dropwise with 3-(3,5-difluorophenyl-4-phenyl-5-methylisoxazole from Step 3 dissolved in a minimum amount of dichloromethane (6 mL). The cooling bath was removed and the mixture was stirred for 6 hours, whereupon the mixture was added dropwise to ice water (500 mL). Ammonium hydroxide (100 mL) and ethyl acetate (100 mL) were added and the mixture was stirred for 16 hours at room temperature. The layers were separated and the organic layer was washed with brine and with water, dried over MgSO$_4$, and concentrated. The product was purified by flash column chromatography, eluting with ethyl acetate:hexane (1:1). The appropriate fractions were concentrated to afford a yellow oil which crystallized upon standing (0.3 g, 21%): mp 58.9°–62.2° C. $^1$H NMR (acetone-d$_6$/300 MHz) 8.0 (d, J=9.3 Hz, 2H), 7.5 (d, J=9.3 Hz, 2H), 7.2 (m, 1H), 7.0 (m, 2H), 6.7 (bs, 2H), 2.8 (s, 3H). Anal. Calc'd. for C$_{16}$H$_{12}$F$_2$N$_2$O$_3$S: C, 53.80; H, 3.60; N. 7.84. Found: C, 53.86; H, 3.72; N, 7.56. High resolution mass spectrum calc'd. (M+H): 351.0615. Found: 351.0626.

EXAMPLE 43

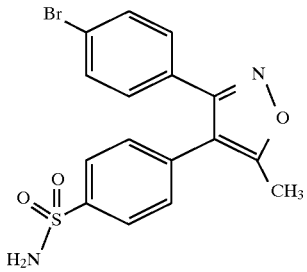

4-[3-(4-Bromophenyl)-5-methyl-isoxazol-4-yl]benzenesulfonamide

Chlorosulfonic acid (25 mL) was cooled to −78° C. and then treated with 4-[5-methyl-4-phenylisoxazol-3-yl] bromobenzene (Example 41, Step 3) (1.5 g, 4.8 mmol). The cooling bath was removed and the mixture was stirred for 4 hours, then added dropwise to ice water (500 mL). Ammonium hydroxide (100 mL) and ethyl acetate (100 mL) were added and the mixture was stirred at room temperature for 16 hours. The layers separated and the organic layer was washed with brine and with water, dried over MgSO$_4$, and concentrated. The product was crystallized from ethanol/water to yield a white solid (0.6 g, 32%): mp 151.9°–153.2° C. $^1$H NMR (acetone-d$_6$/300 MHz) 7.9 (d, J=8.3 Hz, 2H), 7.6 (d, J=8.3 Hz, 2H), 7.4 (d, J=8.7 Hz, 2H), 7.3 (d, J=8.7 Hz, 2H), 6.7 (bs, 2H), 2.5 (s, 3H). Anal. Calc'd. for C$_{16}$H$_{13}$BrN$_2$O$_3$S: C, 48.87; H, 3.33; N, 7.12. Found: C, 48.90; H, 3.37; N, 7.04. High resolution mass spectrum calc'd. (M+H): 392.9909. Found: 392.9887.

EXAMPLE 44

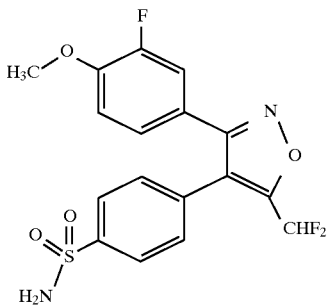

4-[5-Difluoromethyl-3-(3-fluoro-4-methoxyphenyl) isoxazol-4-yl]benzenesulfonamide Step 1. Preparation of 1-(3-fluoro-4-methoxyphenyl)-2-phenyl-ethan-1-one.

Aluminum chloride (42.17 g, 316 mmol) and dichloromethane (350 mL) were cooled to 2° C. and phenylacetylchloride (40.50 g, 262 mmol) in dichloromethane (30 mL) was added. 2-Fluoroanisole (32.77 g, 260 mmol) in dichloromethane (30 mL) was added. The cooling bath was removed, and the mixture was stirred for 1 hour. The reaction mixture was poured into concentrated HCl (150 mL), filtered through diatomaceous earth, washed with saturated aqueous $NaHCO_3$, dried over $MgSO_4$, and concentrated. A white solid was obtained by crystallization from dichloromethane/hexane (29.2 g, 46%): mp 105°–106° C.

Step 2. Preparation of 1-(3-fluoro-4-methoxyphenyl)-2-(4-aminosulfonylphenyl)-ethan-1-one.

Chlorosulfonic acid (75 mL) was cooled to 0° C. and treated portionwise with 1-(3-fluoro-4-methoxyphenyl)-2-phenyl-ethan-1-one from Step 1 (15.24 g, 62.4 mmol). The cooling bath was removed and the mixture was stirred at room temperature for 3 hours. The reaction mixture was diluted with dichloromethane (100 mL) and added dropwise to ice water (500 mL). Ammonium hydroxide (250 mL) was added and the mixture was stirred for 16 hours. A white solid was collected by filtration (8.1 g, 40%). This material was used in the next step without further purification or characterization.

Step 3. Preparation of 1-(3-fluoro-4-methoxyphenyl)-2-(4-aminosulfonylphenyl-ethan-1-one oxime.

1-(3-Fluoro-4-methoxyphenyl)-2-(4-aminosulfonyl) phenyl-ethan-1-one from Step 2 (3.0 g, 9.3 mmol), ethanol (100 mL), water (10 mL), hydroxylamine hydrochloride (1.29 g, 18.6 mmol), and sodium acetate (1.53 g, 18.6 mmol) were combined and heated to 75° C. for 2 hours. The mixture was added to water (100 mL) and the oxime was isolated by filtration as a white solid (2.8 g, 89%): mp 183.9°–186.0° C. $^1$H NMR (acetone-$d_6$/300 MHz) 10.7 (s, 1H), 7.8 (d, J=9.3 Hz, 2H), 7.5 (m, 4H), 7.1 (t, J=9.8 Hz, 2H), 6.5 (bs, 2H), 4.3 (s, 2H), 3.9 (s, 3H). Anal. Calc'd. for $C_{15}H_{15}FN_2O_4S$: C, 53.25; H, 4.47; N, 8.28. Found: C, 53.01; H, 4.51; N, 8.12.

Step 4. Preparation of 4-[5-difluoromethyl-3-(3-fluoro-4-methoxyphenyl)isoxazol-4-yl]benzenesulfonamide 1-(3-Fluoro-4-methoxyphenyl)-2-(4-aminosulfonylphenyl-ethan-1-one oxime from Step 3 (2.0 g, 5.9 mmol), and triethylamine (0.60 g, 5.9 mmol) were dissolved in tetrahydrofuran (100 mL) and treated with bis(1,2-chlorodimethylsilyl)ethane (1.27 g, 5.9 mmol) at room temperature. After 15 minutes, the solution was cooled to −78° C. and lithium diisopropylamide (2.0M solution in heptane/tetrahydrofuran/ethylbenzene, 7.75 mL, 19.5 mmol) was added dropwise. The solution was warmed to −15° C., and ethyl difluoroacetate (0.89 g, 6.5 mmol) was added. After stirring 0.5 hour, trifluoroacetic acid (40 mL) and water (10 mL) were added. The resulting dark mixture was heated to reflux for 20 hours, concentrated, dissolved in ethyl acetate (100 mL), washed with brine, saturated aqueous $NaHCO_3$, and water, dried over $MgSO_4$, and concentrated. A dark oily solid was crystallized from ethyl acetate/hexane to give a white solid (0.3 g, 13%): mp 188.2°–190.0° C. $^1$H NMR (acetone-$d_6$/300 MHz) 8.0 (d, J=8.4 Hz, 2H), 7.6 (d, J=8.7 Hz, 2H), 7.2 (m, 3H), 7.1 (t, J=51.9 Hz, 1H), 6.7 (bs, 2H), 3.9 (s, 3H). Anal. Calc'd. for $C_{17}H_{13}F_3N_2O_4S$: C, 51.26; H. 3.29; N, 7.03. Found: C, 51.35; H, 3.33; N, 6.89.

EXAMPLE 45

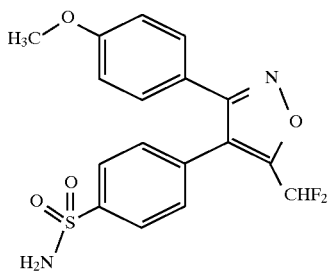

4-[5-Difluoromethyl-3-(4-methoxyphenyl)isoxazol-4-yl]benzenesulfonamide

Step 1. Preparation of 1-(4-methoxyphenyl)-2-phenyl-ethan-1-one.

4-Anisaldehyde (7.35 g, 54 mmol), dichloromethane (100 mL), and zinc iodide (10 mg) were stirred at 0° C. under nitrogen and treated dropwise with trimethylsilylcyanide (5.95 g, 60 mmol). The reaction was stirred for 4 hours, then water (5 mL) was added dropwise. The mixture was washed with brine (2×30 mL), dried over $MgSO_4$, and concentrated under high vacuum. The resulting oily residue was dissolved in tetrahydrofuran (150 mL) and cooled to −78° C. under nitrogen. Lithium diisopropylamide (2.0M solution in heptane/tetrahydrofuran/ethylbenzene, 30 mL, 60 mmol) was added dropwise, maintaining the temperature below −60° C. The solution was stirred for 1 hour, then treated with benzyl bromide (10.26 g, 60 mmol). The cooling bath was removed and the mixture was stirred until the temperature reached −10° C. The solution was poured into a stirred solution of 1N hydrochloric acid (150 mL) and trifluoroacetic acid (10 mL). After stirring for 1 hour, the mixture was extracted with ethyl acetate (2×50 mL). The combined extract was washed with brine (2×50 mL) and concentrated. Sodium hydroxide (2.5 N) was added until basic to pH paper. This mixture was stirred for 2 hours and extracted with ether (2×50 mL). The combined extract was washed with brine and water, dried over $MgSO_4$, and concentrated. After recrystallization from ether/hexane, a tan solid was collected by filtration (4.2 g, 34%): mp 76.7°–77.7° C. $^1$H NMR (acetone-$d_6$/300 MHz) 8.0 (d, J=8.7 Hz, 2H), 7.3 (m, 5H), 7.0 (d, J=9.3 Hz, 3H), 4.3 (s, 2H), 3.9 (s, 3H). Anal. Calc'd. for $C_{15}H_{14}O_2$: C, 79.62; H, 6.24. Found: C, 79.39; H, 6.25.

Step 2. Preparation of 1-(4-methoxyphenyl)-2-(4-aminosulfonylphenyl)-ethan-1-one.

Chlorosulfonic acid (30 mL) was cooled to −78° C. and treated with 1-(4-methoxyphenyl)-2-phenyl-ethan-1-one from Step 1 (4.0 g, 18 mmol). The mixture was warmed to 0° C. and stirred for 2 hours, then added dropwise to ice water (500 mL). Ammonium hydroxide (100 mL) and ethyl acetate (100 mL) were added and the solution was stirred for 16 hours. A sticky white solid, isolated by filtration, was dissolved in boiling acetone/water, and allowed to stand overnight. A white solid was isolated by filtration (2.4 g, 44%): mp 253.7°–257.7° C. $^1$H NMR (DMSO-$d_6$/300 MHz) 8.0 (d, J=8.1 Hz, 2H), 7.7 (d, J=7.5 Hz, 2H), 7.4 (d, J=7.8 Hz, 2H), 7.2 (bs, 2H), 7.0 (d, J=7.8 Hz, 2H), 4.4 (s, 2H), 3.8 (s, 3H). Anal. Calc'd. for $C_{16}H_{13}BrN_2O_3S$: C, 48.87; H, 3.33; N, 7.12. Found: C, 48.77; H, 3.21; N, 6.99.

Step 3. Preparation of 1-(4-methoxyphenyl)-2-(4-aminosulfonylphenyl-ethan-1-one oxime.

1-(4-Methoxyphenyl)-2-(4-aminosulfonylphenyl)ethan-1-one from Step 2 (1.8 g, 5.9 mmol), ethanol (100 mL), water (10 mL), hydroxylamine hydrochloride (0.82 g, 11.8 mmol), and sodium acetate (0.97 g, 11.8 mmol) were combined and heated to 75° C. for 2 hours. The mixture was added to water (100 mL) and a white solid formed which was isolated by filtration (1.3 g, 69%): mp 142.5°–144.3° C. $^1$H NMR (acetone-d$_6$/300 MHz) 10.5 (s, 1H), 7.8 (d, J=8.4 Hz, 2H), 7.7 (d, J=8.7 Hz, 2H), 7.5 (d, J=8.4 Hz, 2H), 6.8 (d, J=9.0 Hz, 2H), 6.5 (bs, 2H), 4.3 (s, 2H), 3.8 (s, 3H).

Step 4. Preparation of 4-[5-difluoromethyl-3-(4-methoxyphenyl)isoxazol-4-yl]benzenesulfonamide.

1-(4-Methoxyphenyl)-2-(4-aminosulfonylphenyl-ethan-1-one oxime from Step 3 (1.2 g, 3.7 mmol), tetrahydrofuran (100 mL), and triethylamine (0.37 g, 3.7 mmol) were stirred at room temperature and treated with bis(1,2-chlorodimethylsilyl)ethane (0.80 g, 3.7 mmol). The solution was cooled to −78° C. under nitrogen. Lithium diisopropylamide (2.0M solution in heptane/tetrahydrofuran/ethylbenzene, 6.1 mL, 12.2 mmol) was added dropwise, and the cooling bath was removed. When the temperature reached −15° C., ethyl difluoroacetate (0.51 g, 4.1 mmol) was added. After stirring 0.5 hour, trifluoroacetic acid (30 mL) and water (10 mL) were added. The resulting dark mixture was heated to reflux for 20 hours, concentrated, dissolved in ethyl acetate (100 mL), washed with brine, saturated NaHCO$_3$, and water, dried over MgSO$_4$, and concentrated. A dark oily solid was purified by flash column chromatography, eluting with ethyl acetate:hexane (1:1). The appropriate fractions were concentrated and crystallized from ethyl acetate/hexane to yield a white solid (0.21 g, 15%): mp 181.6°–182.6° C. $^1$H NMR (acetone-d$_6$/300 MHz) 8.0 (d, J=8.4 Hz, 2H), 7.6 (d, J=8.1 Hz, 2H), 7.5 (d, J=8.1 Hz, 2H), 7.4 (d, J=9.0 Hz, 2H), 7.1 (t, J=51.9 Hz, 1H), 6.7 (bs, 2H), 3.8 (s, 3H). Anal. Calc'd. for C$_{17}$H$_{14}$F$_2$N$_2$O$_4$S: C, 53.68; H, 3.71; N, 7.36. Found: C, 53.71; H, 3.74; N, 7.27.

EXAMPLE 46

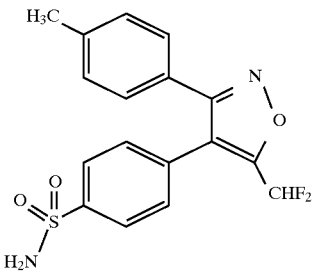

4-[5-Difluoromethyl-3-(4-methylphenyl)isoxazol-4-yl]benzenesulfonamide

Step 1. Preparation of 1-(4-methylphenyl)-2-phenyl-ethan-1-one.

4-Tolualdehyde (12.01 g, 100 mol), dichloromethane (200 mL) and zinc iodide (10 mg) were stirred at 0° C. under nitrogen and treated with trimethylsilylcyanide (10.91 g, 110 mmol). The reaction was stirred for 4 hours, when water (5 mL) was added dropwise. The mixture was washed with brine (2×50 mL), dried over MgSO$_4$, and concentrated under high vacuum. The resulting oily residue was dissolved in tetrahydrofuran (200 mL) and cooled to −78° C. under nitrogen. Lithium diisopropylamide (2.0M solution in heptane/tetrahydrofuran/ethylbenzene, 55 mL, 110 mmol) was added dropwise, maintaining the temperature below −60° C. The solution was stirred for 1 hour and benzyl bromide (18.8 g, 110 mmol) was added. The mixture was warmed to −10° C. then the solution was poured into a stirred solution of 1N hydrochloric acid (150 mL) and trifluoroacetic acid (10 mL). After stirring for 1 hour, the mixture was extracted with ethyl acetate (2×100 mL). The combined extract was washed with brine (2×50 mL) and concentrated. Sodium hydroxide (2.5N, 75 mL) was added and a yellow solid formed which was isolated by filtration. The yellow solid was dissolved in boiling acetone/ethanol and crystallized by the dropwise addition of water. A light yellow solid was collected by filtration (16.7 g, 79%) : mp 109.6°–112.0° C. $^1$H NMR (acetone-d$_6$/300 MHz) 8.0 (d, J=8.1 Hz, 2H), 7.3 (m, 7H), 4.3 (s, 2H), 2.4 (s, 3H). Anal. Calc'd. for C$_{15}$H$_{14}$O: C, 85.68; H, 6.71. Found: C, 85.77; H, 6.70.

Step 2. Preparation of 1-(4-methylphenyl)-2-(4-aminosulfonylphenyl)-ethan-1-one.

Chlorosulfonic acid (30 mL) was cooled to −78° C. and 1-(4-methylphenyl)-2-phenyl-ethan-1-one from Step 1 (4.0 g, 18 mmol) was added. The mixture was warmed to 0° C. and stirred for 2 hours, then added dropwise to ice water (500 mL). Ammonium hydroxide (100 mL) and ethyl acetate (100 mL) were added and the mixture was stirred for 16 hours. A white solid formed which was isolated by filtration. The crude ketone was dissolved in boiling acetone/ethanol/water and let stand overnight, whereupon a white solid formed which was collected by filtration (4.2 g, 31%): mp 250.4°–255.2 ° C. $^1$H NMR (DMSO-d$_6$/300 MHz) 8.0 (d, J=8.1 Hz, 2H), 7.7 (d, J=8.4 Hz, 2H), 7.4 (d, J=8.1 Hz, 2H), 7.3 (d, J=7.8 Hz, 2H), 7.2 (bs, 2H), 4.5 (s, 2H), 2.4 (s, 3H). High resolution mass spectrum calc'd. for C$_{15}$H$_{15}$NO$_3$S: 290.0851. Found: 290.0834.

Step 3. Preparation of 1-(4-methylphenyl)-2-(4-aminosulfonylphenyl-ethan-1-one oxime.

1-(4-Methylphenyl)-2-(4-aminosulfonylphenyl)-ethan-1-one from Step 2 (3.5 g, 12 mmol), ethanol (100 mL), water (10 mL), hydroxylamine hydrochloride (1.67 g, 24 mmol), and sodium acetate (1.97 g, 24 mmol) were combined and heated to 75° C. for 2 hours. The mixture was added to water (100 mL) and the material was isolated by filtration to afford a white solid (2.1 g, 57%): mp 163.4°–165.8° C.

Step 4. Preparation of 4-[5-difluoromethyl-3-(4-methylphenyl)isoxazol-4-yl]benzenesulfonamide.

1-(4-Methylphenyl)-2-(4-aminosulfonylphenyl-ethan-1-one oxime from Step 3 (2.0 g, 6.6 mmol), tetrahydrofuran (100 mL), and triethylamine (0.67 g, 6.6 mmol) were stirred at room temperature and treated with bis(1,2-chlorodimethylsilyl)ethane (1.42 g, 6.6 mmol). The solution was cooled to −78° C. under nitrogen. Lithium diisopropylamide (2.0M solution in heptane/tetrahydrofuran/ethylbenzene, 10.9 mL, 21.8 mmol) was added dropwise, and the cooling bath was removed. When the temperature reached −15° C., ethyl difluoroacetate (0.82 g, 6.6 mmol) was added all at once. After stirring for 0.5 hour, trifluoroacetic acid (30 mL) and water (10 mL) were added. The resulting dark mixture was heated to reflux for 20 hours, concentrated, dissolved in ethyl acetate (100 mL), washed with brine, saturated aqueous NaHCO$_3$, and water, dried over MgSO$_4$, and concentrated. A dark oily solid was purified by flash column chromatography eluting with ethyl acetate:hexane (1:1). The appropriate fractions were concentrated and crystallized from ethyl acetate/hexane to yield a white solid (0.23 g, 10%): mp 169.0°–172.3° C. $^1$H NMR (acetone-d$_6$/300 MHz) 8.0 (d, J=8.4 Hz, 2H), 7.5 (d, J=8.1 Hz, 2H), 7.3 (d, J=8.1 Hz, 2H), 7.2 (d, J=8.1 Hz, 2H), 7.1 (t, J=51.9 Hz, 1H), 6.7 (bs, 2H), 2.4 (s, 3H). High resolution mass spectrum calc'd. for C$_{17}$H$_{15}$F$_2$N$_2$O$_3$S(M+H): 365.0771. Found: 365.0779.

EXAMPLE 4

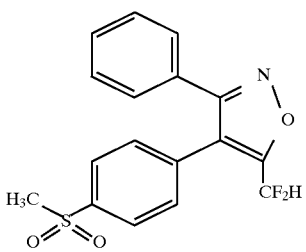

5-Difluoromethyl-4-(4-methylsulfonylphenyl)-3-phenylisoxazole

Step 1. Preparation of 2-phenylpropenoic acid.

Phenylacetic acid (45.46 g, 334 mmol), 4-(methylthio)benzaldehyde (50.35 g, 331 mmol), triethylamine (34.54 g, 341 mmol) and acetic anhydride (200 mL) were heated to reflux for 0.9 hours. The reaction was cooled to 90° C. and water (200 mL) was added slowly. A yellow precipitate formed, and after cooling to room temperature, the solid was collected by filtration and recrystallized from toluene to give the diarylpropenoic acid as yellow needles (48.04 g, 61%): mp 164°–168° C. $^1$H NMR (acetone-$d_6$) 300 MHz 7.82 (s, 1H) 7.38 (m, 3H) 7.26 (m, 2H) 7.05 (m, 4H) 2.45 (s, 3H).

Step 2. Preparation of 2-(4-methylthiophenyl)-1-phenylethanone

The diarylpropenoic acid from Step 1 (54.10 g, 200 mmol) and triethylamine (22.92 g, 226 mmol) were dissolved in toluene (260 mL), cooled to 0° C. and treated with diphenylphosphorylazide (55.35 g, 201 mmol). The reaction was stirred at room temperature 4.4 hours, poured into water, extracted with ether, dried over MgSO$_4$, and concentrated in vacuo. The solution was heated to reflux and a vigorous evolution of gas occurred. After 1.67 hours, tert-butyl alcohol (10 mL, 120 mmol) was added to the reaction. After an additional 1.0 hour, concentrated hydrochloric acid (16.5 mL) was added and the reaction was heated at 75° C. overnight (14 hours). After cooling, a white precipitate formed. The precipitate was filtered, washed with water and ethyl acetate, and dried to give the ketone. The filtrate was washed with water, and brine, dried over MgSO$_4$, concentrated in vacuo and recrystallized from ethyl acetate/hexane to give additional ketone as a yellow powder (33.58 g, 69%): mp 123°–127° C. $^1$H NMR (acetone-$d_6$) 300 MHz 8.06 (d, J=8.1 Hz, 2H) 7.51–7.62 (m, 3H) 7.25 (m, 4H) 4.35 (s, 2H) 2.46 (s, 3H).

Step 3. Preparation of 2-(4-methylthiophenyl)-1-phenylethanone oxime.

Hydroxylamine hydrochloride (9.76 g, 140 mmol) was dissolved in ethanol (40 mL) and stirred at room temperature with potassium hydroxide (7.98 g, 142 mmol) for 0.67 hours. Toluene (200 mL) and the ketone from Step 2 (33.58 g, 139 mmol) were added and the reaction was heated to reflux for 4.0 hours. The reaction mixture was filtered while hot, and upon cooling to room temperature, gave a white precipitate which was filtered and dried to give the oxime as a white powder (20.19 g, 57%): mp 122°–123.5° C. $^1$H NMR (acetone-$d_6$) 300 MHz 10.61 (s, 1H) 7.70 (m, 2H) 7.31 (m, 3H) 7.23 (d, J=8.3 Hz, 2H) 7.18 (d, J=8.3 Hz, 2H) 4.21 (s, 2H) 2.43 (s, 3H).

Step 4. Preparation of 5-difluoromethyl-4-(4-methylthiophenyl)-3-phenylisoxazole The oxime from Step 3 (14.13 g, 54.9 mmol) was dissolved in tetrahydrofuran (150 mL), cooled to –78° C., and treated with 2.1 equivalents of n-butyllithium. The reaction was warmed to 10° C. over 1.9 hours, treated with ethyl difluoroacetate (7.03 g, 56.7 mmol) and stirred at room temperature for 3.2 hours. The reaction was quenched with water, extracted with ethyl acetate, washed with saturated NaHCO$_3$, and brine, dried over MgSO$_4$, and concentrated in vacuo to give a brown oil (12.17 g). The oil was dissolved in tetrahydrofuran (50 mL) along with triethylamine (8.02 g, 79.2 mmol), dimethylaminopyridine (1.13 g, 9.2 mmol), and toluenesulfonyl chloride (7.72 g, 40.5 mnmol). The solution was heated to reflux for 1.8 hours, ethyl acetate was added and the reaction mixture was washed with 3N HCl, saturated NaHCO$_3$, and brine, dried over MgSO$_4$, and concentrated in vacuo. The material was purified (silica gel eluting with 25% ethyl acetate/hexane) to give the isoxazole as a brown oil (6.12 g, 35%): $^1$H NMR (CDCl$_3$) 300 MHz 7.32–7.45 (m, 5H) 7.24 (d, J=–8.5 Hz, 2H) 7.16 (d, J=8.5 Hz, 2H) 6.63 (t, J=52.4 Hz, 1H) 2.51 (s, 3H). $^{19}$F NMR (acetone-$d_6$) 282 MHz –116.26 (d). Mass spectrum: M+=317.

Step 5. Preparation of 5-difluoromethyl-4-(4-methylsulfonyl-phenyl)-3-phenylisoxazole The isoxazole from Step 4 (6.29 g, 19.8 mmol) was dissolved in a mixture of tetrahydrofuran, ethanol, and water (1:1:1, 60 mL). The reaction was treated with OXONE(®) (24.43 g, 39.7 mmol), stirred at room temperature for 1.25 hours, filtered and concentrated in vacuo. The residue was dissolved in ethyl acetate, washed with saturated NaHCO$_3$, and brine, dried over MgSO$_4$, concentrated in vacuo and passed through a column of silica gel eluting with 50% ethyl acetate/hexane to give the sulfone as a white solid (4.74 g, 68%): mp 126°–128° C. $^1$H NMR (acetone-$d_6$) 300 MHz 8.02 (d, J=8.7 Hz, 2H) 7.64 (d, J=8.5 Hz, 2H) 7.42–7.46 (m, 5H) 7.18 (t, J=52.0 Hz, 1H) 3.18 (s, 3H). $^{19}$F NMR (acetone-$d_6$) 282 MHz –118.36 (d). High resolution mass spectrum calc'd. for $C_{17}H_{14}F_2NO_3S$: 350.0662. Found: 350.0664.

EXAMPLE 48

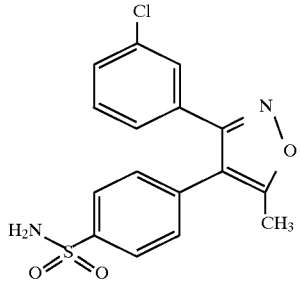

4-[3-(3-Chlorophenyl)-5-methylisoxazol-4-yl]benzenesulfonamide

Step 1. Preparation of 1-(3-chlorophenyl)-2-phenyl-ethan-1-one.

Cyanotrimethylsilane (13.36 mL, 105.6 mmol) was added to a stirred mixture of 3-chlorobenzaldehyde (15.0 g, 108.3 mmol) and zinc iodide (0.75 g) in anhydrous dichloromethane (100 mL) under nitrogen at 10° C. The reaction mixture was stirred for 90 minutes and poured into aqueous sodium bicarbonate (200 mL). The organic layer was washed with brine (200 mL), dried and concentrated to afford the cyanohydrin. A solution of tetrahydrofuran (100 mL) and lithium hexamethyldisilylamide (96.4 mL, 1N, 96.4 mmol) was cooled to –78° C. The cyanohydrin in tetrahydrofuran (50 mL) was added slowly to the above mixture. After 15 minutes at –78° C., benzylbromide (15.11 g 88.4 mmol) was added. The reaction mixture was stirred for 1 hour and was warmed to room temperature. The mixture was poured into trifluoroacetic acid (200 mL) containing 10% water and stirred for 2 hours. The mixture was neutralized with solid Na$_2$CO$_3$, extracted with ethyl acetate (300 mL), washed with brine (200 mL), dried and concentrated. The residue was stirred with aqueous NaOH (2N, 200 mL). The solid formed was filtered, washed with water, dried and recrystallized from hexane to afford the desired ketone (19.5 g, 78%): mp 153°–156° C. $^1$H NMR (CDCl$_3$) 7.99–7.82 (m, 4H), 7.51–7.19 (m, 5H), 4.03 (s, 2H).

Step 2. Preparation of 1-(3-chlorophenyl)-2-phenyl-ethan-1-one oxime.

A mixture of 1-(3-chlorophenyl)-2-phenyl-ethan-1-one from Step 1 (9.3 g, 40.4 mmol), hydroxylamine hydrochloride (7.29 g, 105.0 mmol), sodium acetate (20.6 g, 251 mmol), ethanol (90 mL) and water (90 mL) was heated to reflux for 4 hours, diluted with water (200 mL) and cooled. The precipitate formed was filtered, dried and recrystallized from hexane/ethyl acetate to afford the desired oxime (8.2 g, 83%): mp 120°–121° C. $^1$H NMR (CDCl$_3$) 7.62–7.21 (m, 9H), 4.20 (s, 2H).

Step 3. Preparation of 4-[5-methyl-3-(3-chlorophenyl) isoxazol-4-yl]benzenesulfonamide.

Butyllithium (11.8 mL, 1.6N, 18.9 mmol) was added to a solution of 1-(3-chlorophenyl)-2-phenyl-ethan-1-one oxime from Step 2 (2.11 g, 8.60 mmol) in dry tetrahydrofuran (45 mL) at −78° C. The reaction mixture was stirred for 30 minutes at −78° C., warmed to 0° C., then cooled again to −78° C. Ethyl acetate (0.832 g, 9.45 mmol) was added to the reaction mixture and warmed to room temperature. The reaction mixture was quenched with saturated NH$_4$Cl, extracted with ethyl acetate, dried over MgSO$_4$, filtered and concentrated in vacuo. Chromatographic purification of the residue (silica gel flash chromatography, hexane:ethyl acetate (2:1)) afforded the desired hydrate. The hydrate was added to chlorosulfonic acid (10 mL) at 0° C. and stirred for 3 hours. The reaction was diluted with dichloromethane (25 mL), then poured carefully into an ice-water mixture. The quenched reaction mixture was extracted with dichloromethane (200 mL). The organic layer was added to ammonium hydroxide (200 mL) and stirred for 18 hours. The organic layer was separated, washed with brine (100 mL), dried (MgSO$_4$) and concentrated. Flash chromatography on silica gel (1:1 ethyl acetate, hexane) of the residue afforded the desired product as a crystalline material (0.40 g): mp 72°–83° C. $^1$H NMR (CDCl$_3$) 7.93 (d, 2H, J=8.5 Hz), 7.46–7.13 (m, 6H), 5.4 (s, 2H), 2.46 (s, 3H). FABMS Calc'd. for C$_{16}$H$_{13}$ClN$_2$O$_3$S: 348 (M+). Found 348.

EXAMPLE 49

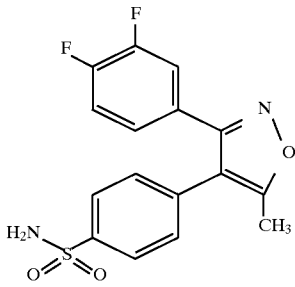

4-[3-(3,4-Difluorophenyl)-5-methylisoxazol-4-yl] benzenesulfonamide

Step 1. Preparation of 1-(3,4-difluorophenyl)-2-phenyl-ethan-1-one.

Cyanotrimethylsilane (13.36 mL, 105.6 mmol) was added to a stirred mixture of 3,4-difluorobenzaldehyde (15.0 g, 105.6 mmol) and zinc iodide (0.90 g) in anhydrous dichloromethane (100 mL) under nitrogen at 10° C. The mixture was stirred for 90 minutes and was poured into aqueous NaHCO$_3$ (200 mL). The organic layer was washed with brine (200 mL), dried over MgSO$_4$, filtered and concentrated to afford the cyanohydrin. A solution of tetrahydrofuran (100 mL) and lithium hexamethyldisilylamide (118.0 mL, 1N, 118.0 mmol) was cooled to −78° C. The cyanohydrin in tetrahydrofuran (50 mL) was added slowly to the above mixture. After 15 minutes at −78° C., benzylbromide (18.06 g 106.67 mmol) was added. The mixture was stirred for 1 hour and warmed to room temperature. The mixture was poured into trifluoroacetic acid (90%), stirred for 2 hours, and neutralized with solid Na$_2$CO$_3$. The mixture was extracted with ethyl acetate (300 mL), washed with brine (200 mL), dried, and concentrated. The residue was stirred with aqueous NaOH (2N, 200 mL). The solid formed was filtered, washed with water, dried and recrystallized from hexane to afford the desired ketone (13.55 g, 55%): mp 116°–121° C. $^1$H NMR (CDCl$_3$) 7.86–75 (m, 2H), 7.37–7.18 (m, 7H), 4.23 (s, 2H).

Step 2. Preparation of 1-(3,4-difluorophenyl)-2-phenyl-ethan-1-one oxime.

A mixture of 1-(3,4-difluorophenyl)-2-phenyl-ethan-1-one from Step 1 (12.5 g, 53.88 mmol), hydroxylamine hydrochloride (9.4 g, 135.4 mmol) and sodium acetate (268.5 mmol) in ethanol/water (1:1, 250 mL) was heated to reflux for 4 hours. Upon addition of water (200 mL) a precipitate formed. The precipitate was filtered, dried and recrystallized from hexane to afford the desired oxime (10 g, 75%): mp 81°–82° C. $^1$H NMR (CDCl$_3$) 7.5–7.06 (m, 9H), 4.18 (s, 2H).

Step 3. Preparation of 4-[5-methyl-3-(3,4-difluorophenyl) isoxazol-4-yl]benzenesulfonamide.

Butyllithium (18.1 mL, 1.6N, 45 mmol) was added to a solution of 1-(3,4-difluorophenyl)-2-phenyl-ethan-1-one oxime from Step 2 (5.505 g, 20.5 mmol) in dry tetrahydrofuran (200 mL) at −78° C. The reaction mixture was stirred for 30 minutes at −78° C., warmed up to 0° C., then cooled to −78° C. Ethyl acetate (1.801 g, 20.45 mmol) was added to the reaction mixture and the mixture was warmed to room temperature. The reaction mixture was quenched with saturated ammonium chloride solution, extracted with ethyl acetate, dried over MgSO$_4$ and concentrated in vacuo. The desired hydrate was obtained by purifying the residue (silica gel flash chromatography, hexane:ethyl acetate (2:1)). The hydrate was added to chlorosulfonic acid (10 mL) at 0° C. and stirred for 3 hours. The mixture was diluted with dichloromethane (25 mL), then poured carefully in to ice-water mixture. The mixture was extracted with dichloromethane (200 mL) and the organic layer was added to ammonium hydroxide (200 mL) and stirred for 18 hours. The organic layer was separated, washed with brine (100 mL), dried over MgSO$_4$ and concentrated in vacuo. Flash chromatography on silica gel (1:1 ethyl acetate/hexane) of the residue afforded the desired product as a crystalline material (0.360 g): mp 149°–153° C. $^1$H NMR (CDCl$_3$) 7.88 (d, 2H, J=7.85 Hz), 7.25 (d, 2H, J=8.25 Hz), 7.04–7.19 (m, 3H), 3.28 (s, 2H) , 2.41 (s, 3H). FABMS Calc'd for C$_{16}$H$_{12}$F$_2$N$_2$O$_3$S: 350 (M+). Found=350.

EXAMPLE 50

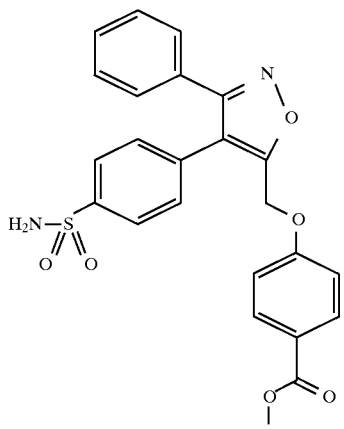

Methyl 4-[[4-[4-(aminosulfonyl)phenyl]-3-phenylisoxazol-5-yl]methoxy]benzoate

Methyl 4-hydroxybenozate (152.0 mg, 1.00 mmol), 4-[5-chloromethyl-3-phenylisoxazol-4-yl]-benzenesulfonamide [EXAMPLE 1(k), 300.0 mg, 0.86 mol], and potassium carbonate (200 mg, 1.44 mmol) were mixed together in dimethylformamide (5.0 mL) for 168 hours at room temperature. The solution was poured into ethyl acetate (100 mL), and washed with saturated aqueous $NaHCO_3$ (2×50 mL) and brine (2×50 mL). The organic phase was dried over $MgSO_4$, filtered and concentrated in vacuo. The crude product was purified by flash chromatography over silica gel, eluting with hexanes and ethyl acetate. The appropriate fractions were combined and concentrated to afford methyl 4-[[4-[4-(aminosulfonyl)phenyl]-3-phenylisoxazol-5-yl]methoxy]benzoate as a white foam (149 mg, 37%): $^1H$ NMR ($CDCl_3$) 3.90 (s, 3H), 4.87 (bs, 2H), 5.17 (s, 2H) 6.96 (d, 2H, J=8.7 Hz), 7.35–7.44 (m, 7H), 7.91 (d, 2H, J=8.7 Hz), 7.98 (d, 2H, J=9.1 Hz). Mass spectrum calc'd. for $C_{24}H_{20}N_2O_6S$: 464. Found: 465 (m+H$^+$).

EXAMPLE 51

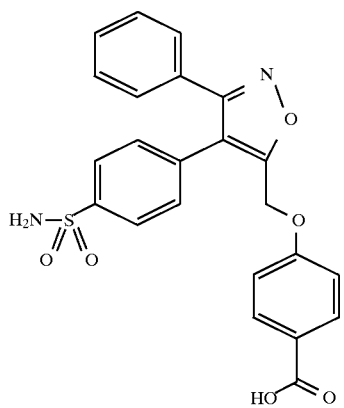

4-[[4-[4-(Aminosulfonyl)phenyl]-3-phenylisoxazol-5-yl]methoxy]benzoic acid

Methyl 4-[[4-[4-(aminosulfonyl)phenyl]-3-phenylisoxazol-5-yl]methoxy]benzoate (Example 50) (65.0 mg, 0.14 mmol) was dissolved in tetrahydrofuran/methanol/water (5.0 mL 7:2:1) and lithium hydroxide (10 mg, 0.250 mmol) was added. The solution was heated to reflux for 4 hours and cooled to room temperature. The solvent was removed in vacuo and the crude product was purified by preparative high pressure liquid chromatography using a $C_{18}$ reverse phase column. The appropriate factions were combined and concentrated to afford pure 4-[[4-[4(aminosulfonyl)phenyl]-3-phenylisoxazol-5-yl]methoxy] benozoic acid as a white crystalline material (38 mg, 60%): mp 206.4°–207.9° C. $^1H$ NMR $CD_3OD$ 5.29 (S, 2H), 7.01 (d, 2H, 8.4 Hz), 7.25–7.45 (m, 7H), 7.84–7.97 (m, 4H). Mass spectrum calc'd. for $C_{23}H_{18}N_2O_6S$: 450. Found: 451 (m+H$^+$).

EXAMPLE 52

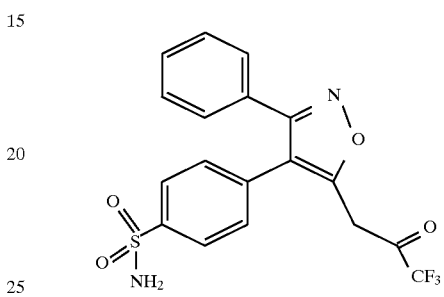

4-[3-Phenyl-5-(3,3,3-trifluoro-2-oxopropyl)isoxazol-4-yl]benzenesulfonamide

Step 1: Preparation of [[4-(5-methyl-3-phenylisoxazol-4-yl)phenyl]sulfonyl]-carbamic acid, 1,1-dimethylethylester To a stirred suspension of 4-[5-methyl-3-phenylisoxazol-4-yl]benzenesulfonamide (Example 1) (10.42 g, 33.1 mmol) in dichloromethane (100 mL) was added di-tert-butyldicarbonate (7.59 g, 34.80 mmol), dimethylaminopyridine (0.202 g, 1.66 mmol) and triethylamine (5.07 mL, 3.68 g, 36.4 mmol). The resulting homogeneous solution was stirred overnight. The reaction was diluted with ethyl acetate and dichloromethane, washed with $KHSO_4$ solution (0.25M), brine, dried over $MgSO_4$, filtered and concentrated in vacuo yielding a white powder. The powder was dissolved in hot ethyl acetate and diluted with isooctane, yielding [[4-(5-methyl-3-phenylisoxazol-4-yl)phenyl]sulfonyl]-carbamic acid, 1,1-dimethylethylester as a fine white powder (9.94 g, 72%): mp 167.6°–170.5° C. $^1H$ NMR ($CDCl_3$) 8.01 (d, J=8.66 Hz, 2H), 7.51 (s, 1H), 7.46–7.30 (m, 7H), 2.50 (s, 3H), 1.40 (s, 9H). LRMS M+H obs at m/z 415. Anal. Calc'd. for $C_{21}H_{22}N_2O_5S$: C, 60.86; H, 5.35; N, 6.76. Found: C, 60.79; H, 5.40; N, 6.75.

Step 2. Preparation of [[4-[3-phenyl-5-(3,3,3-trifluoro-2-oxopropyl)isoxazol-4-yl]phenyl]sulfonyl]carbamic acid, 1,1-dimethylethylester A chilled (−78° C.), stirred solution of [[4-(5-methyl-3-phenylisoxazol-4-yl)phenyl]sulfonyl]-carbamic acid, 1,1-dimethylethylester from Step 1 (2.344 g, 5.655 mmol) in THF (50 mL) was treated with n-butyllithium (7.8 mL of 1.6M in hexanes, 12.44 mmol). The resulting red solution was warmed to 0° C., cooled to −24° C., treated with ethyl trifluoroacetate (0.34 mL, 0.40 g, 2.83 mmol) and warmed to room temperature. The reaction was quenched with saturated $NH_4Cl$ solution and adjusted to pH 2 with 1N HCl. The mixture was extracted with ethyl acetate, dried over $MgSO_4$¸ filtered and concentrated in vacuo. The crude product was purified by flash chromatography yielding [[4-[3-phenyl-5-(3,3,3-trifluoro-2-oxopropyl)isoxazol-4-yl]phenyl]sulfonyl]-carbamic acid, 1,1-dimethylethylester (1.38 g, 48%) as a viscous oil of suitable purity for further elaboration.

Step 3. Preparation of 4-[3-phenyl-5-(3,3,3-trifluoro-2-oxopropyl)isoxazol-4-yl]benzenesulfonamide The [[4-[3-phenyl-5-(3,3,3-trifluoro-2-oxopropyl)isoxazol-4-yl]phenyl]sulfonyl]-carbamic acid, 1,1-dimethylethylester from Step 2 was dissolved in trifluoroacetic acid (25 mL) and water (2 mL). After 4 hours, the reaction was concentrated under high vacuum, toluene was added and the mixture reconcentrated to remove trace trifluoroacetic acid. The resulting white semi-solid was dissolved in hot ethyl acetate, isooctane was added and the mixture was partially concentrated, yielding a crystalline solid. Vacuum filtration of the suspension yielded 4-[3-phenyl-5-(3,3,3-trifluoro-2-oxopropyl)isoxazol-4-yl]benzenesulfonamide as a white powder (0.302 g, 29%): mp 132.1°–138.7 ° C. $^1$H NMR (CD$_3$CO$_2$D) 8.01–7.90 (m, 2H), 7.53 (d, J=8.46, 1H), 7.50–7.30 (m, 6H), 6.02 (s, 0.4H), 3.37 (s, 1H). LRMS: M+H obs at m/z 411 and (M—H$_2$O)+H obs. at m/z 429. Anal. Calc'd. for C$_{18}$H$_{13}$N$_2$O$_4$SF.0.5 H$_2$O: C, 51.58; H, 3.45; N, 6.64. Found: C, 51.28; H, 3.45; N, 6.64.

EXAMPLE 53

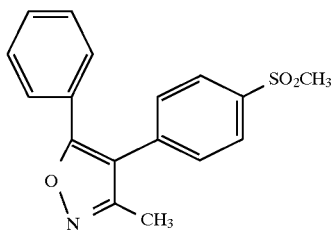

3-Methyl-4-(4-methylsulfonylphenyl)-5-phenylisoxazole

Step 1: Preparation of 1-phenyl-2-(4-methylthiophenyl)-1-buten-3-one

A solution of 1-(4-methylthiophenyl)-2-propanone [G. Y. Lesher, U.S. Pat. No. 4,517,192, May 14, 1985; L. M. Werfel et al, J. Med. Chem., 29, 924–36 (1986)] (11.2 g, 0.062 mol) and benzaldehyde (6.6 g, 0.062 mol) in benzene (75 ml) containing piperidine (200 mg) was heated at reflux for 24 hours. After cooling, the solvent was removed and the residue was purified by chromatography on silica gel using mixtures of ethyl acetate and toluene to give the ketone. This material was recrystallized from ethyl acetate and hexane to give 14 g (82%) of pure ketone as a crystalline solid: mp 91°–93° C. Anal. Calc'd. for C$_{17}$H$_{16}$OS (268.38): C, 76.08; H, 6.01; S, 11.95. Found: C, 76.15; H, 6.08; S, 11.79.

Step 2: Preparation of 1-phenyl-2-(4-methylthiophenyl)-1-buten-3-one oxime

A solution of 1-phenyl-2-(4-methylthiophenyl)-1-buten-3-one (Step 1) (12.85 g, 0.048 mol), sodium acetate (4.75 g, 0.057 moles), and hydroxylamine hydrochloride (4.0 g, 0.057 mol) in ethanol (275 ml) and water (30 ml) was heated at reflux for 4 hours. After cooling, water was added and the precipitate was filtered and air dried. This crude oxime was recrystallized from ethanol and water to give pure oxime (10.4 g, 76%): mp 101°–102° C. Anal. Calc'd. for C$_{17}$H$_{17}$NOS (283.39): C, 72.05; H, 6.05; N, 4.94; S, 11.31. Found: C, 71.95; H, 5.99; N, 4.72; S, 11.50.

Step 3: Preparation of 3-methyl-4-(4-methylthiophenyl)-5-phenylisoxazole

To a stirred solution of 1-phenyl-2-(4-methylthiophenyl)-1-buten-3-one oxime (Step 2) (11.2 g, 0.0395 mol), sodium bicarbonate (13.6 g, 0.162 mol), and potassium iodide (22.95 g, 0.138 mol) in tetrahydrofuran (200 ml) and water (160 ml) was added iodine (10 g, 0.0395 mol). The reaction vessel was covered with aluminum foil and heated at reflux for 4 hours. Thin layer chromatography indicated the reaction was completed. The reaction was cooled to room temperature, sodium bisulfite was added and the reaction was extracted with ethyl acetate. The organic extracts were dried and the solvent was removed to give the crude isoxazole. The crude was purified by chromatography on silica gel using mixtures of ethyl acetate and toluene. The isoxazole was recrystallized from ethyl acetate and hexane to give pure compound as a crystalline solid (8.3 g, 75%): mp 88°–90° C. Anal. Calc'd. for C$_{17}$H$_{15}$NOS (281.38): C, 72.57; H, 5.37; N, 4.98; S, 11.40. Found: C, 72.20; H, 5.27; N, 4.58; S, 11.69.

Step 4: Preparation of 3-methyl-4-(4-methylsulfonylphenyl)-5-phenylisoxazole

To a solution of 3-methyl-4-(4-methylthiophenyl)-5-phenylisoxazole (Step 3) (285 mg, 1 mmol) in tetrahydrofuran and methanol (1:1) was added a solution of Oxone® (900 mg, 1.5 mmol) in water (5 ml). The reaction mixture was stirred rapidly at 25° C. for 3 hours. The reaction mixture was extracted with ethyl acetate and the organic extracts dried. After filtration and solvent removal, the crude residue was recrystallized from ethyl acetate and hexane to give pure product as a crystalline solid (250 mg, 79%): mp 144°–145° C. Anal. Calc'd. for C$_{17}$H$_{15}$NO$_3$S (313.38): C, 65.16; H, 4.82; N, 4.47; S, 10.23. Found: C, 65.26; H, 4.78; N, 3.99; S, 10.22.

EXAMPLE 54

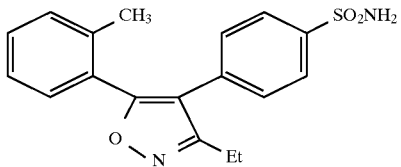

4-[3-Ethyl-5-(2-methylphenyl)isoxazol-4-yl]benzenesulfonamide

This compound was made by the same procedure as described for Example 14: mp 159°–162° C.; Anal. Calc'd. for C$_{18}$H$_{18}$N$_2$O$_3$S: C, 63.14; H, 5.30; N, 8.18; S, 9.36. Found: C, 62.75; H, 4.96; N, 7.85; S, 9.26.

EXAMPLE 55

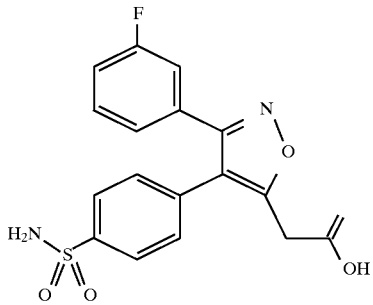

[4-(4-Aminosulfonylphenyl)-3-(3-fluorophenyl)isoxazol-5-yl]acetic acid

A solution of 4-[5-methyl-3-(3-fluorophenyl)isoxazol-4-yl]benzenesulfonamide (Example 4 g) (1.0 g, 2.854 mmol) in tetrahydrofuran (25 mL) was cooled to −78° C. N-Butyllithium (4.0 mL, 1.6M, 6.28 mmol) was added slowly to the reaction mixture. The reaction mixture was warmed to 0° C., cooled again to −78° C. and anhydrous carbon dioxide was slowly bubbled through the reaction mixture. The reaction mixture turned gray and the mixture was warmed up to room temperature. After quenching with saturated ammonium chloride, the reaction mixture was extracted with ethyl acetate. The combined ethyl acetate extracts were washed with sodium bicarbonate. The combined aqueous extracts were cooled and acidified with hydrochloric acid. The precipitate formed was extracted with ethyl acetate. The combined organic layers were dried and concentrated to afford the desired product (0.40 g, 38%): mp 242°–250° C. $^1$H NMR (CDCl$_3$) 7.74 (d, 2H, J=8.3 Hz), 7.27–6.94 (m, 7H), 3.56 (s, 2H). Anal. Calc'd for C$_{17}$H$_{13}$N$_2$O$_5$SF: mol wt, 377.0607 (M+H). Found: mol wt 377.0607 (M+H, HRFABMS).

EXAMPLE 56

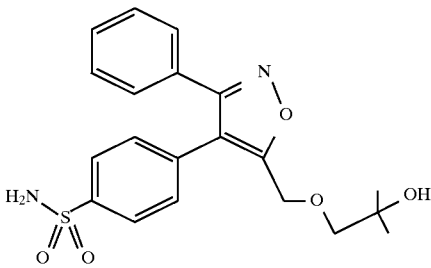

4-[5-(2-Methyl-2-hydroxy-1-n-propyloxymethyl)-3-phenylisoxazol-4-yl]benzenesulfonamide Step 1: Preparation of methyl [[4-[4-(aminosulfonyl)-phenyl]-3-phenylisoxazol-5-yl]methyloxyacetate 5-[4-[4-[N-[2,5-Dimethylpyrrol]-sulfonyl]phenyl]-3-phenylisoxazol-5-yl]]-methyloxyacetic acid (Example 35, step 1) (0.461 g, 0.988 mmol) was stirred in TFA (9 mL) and H$_2$O (3 mL) and heated to 70° C. for 8 hours. Concentration in vacuo yielded a brown foam. This brown solid was dissolved in a carefully prepared solution of thionyl chloride (1 mL) in methanol (20 mL). The resulting black solution was heated to reflux for 3 hours. The reaction was concentrated in vacuo and the residue was redissolved in TFA (9 mL) and H$_2$O (3 mL) and heated to 70° C. for 8 more hours. The reaction was concentrated in vacuo and added to a carefully prepared solution of thionyl chloride (1 mL) in methanol (20 mL). After 3 hours at reflux, the reaction was concentrated in vacuo, and redissolved in methanol. Decolorizing carbon was added and the mix was heated. The suspension was filtered through diatomaceous earth, concentrated in vacuo and purified by flash chromatography yielding methyl [[4-[4-(aminosulfonyl)phenyl]-3-phenylisoxazol-5-yl]methoxy]acetate of sufficient purity to use in the next step.

Step 2: Preparation of 4-[5-(2-methyl-2-hydroxy-1-n-propyloxymethyl)-3-phenylisoxazol-4-yl]benzenesulfonamide To a stirred solution of methyl [[4-[4-(aminosulfonyl)phenyl]-3-phenylisoxazol-5-yl]methoxy]acetate (Step 1) 0.17 g, 0.44 mmol) in THF (5 mL) was added methyl magnesium bromide (0.6 mL of 3.0M solution in Et$_2$O, 1.75 mmol) and the resulting suspension was stirred for 48 hours. The reaction was quenched with 1N HCl and extracted with ethyl acetate. The ethyl acetate phase was washed with brine, dried over MgSO$_4$, filtered and concentrated in vacuo. The resulting crude product was recrystallized from isooctane and dichloromethane yielding 4-[5-(2-methyl-2-hydroxy-1-n-propyloxymethyl)-3-phenylisoxazol-4-yl]benzenesulfonamide as a tan powder (0.068 g, 38%), mp 160°–162° C. $^1$H NMR (CDCl$_3$/300 MHz) 7.89 (d, 2H, J=8.3 Hz), 7.44–7.28 (m, 7H), 5.97 (s, 2H), 4.59 (s, 2H), 3.36 (s, 2H),1.17 (s, 6H). FABLRMS m/z 403 (M+H). FABHRMS m/z 403.1328 (M+H, C$_{17}$H$_{17}$N$_2$O$_5$S requires 403.1328). Anal. Calc'd for C$_{20}$H$_{22}$N$_2$O$_5$S .2.53 wt % H$_2$O: C, 58.18 H, 5.65; N, 6.78. Found: C, 58.17; H, 5.38; N, 6.61.

EXAMPLE 57

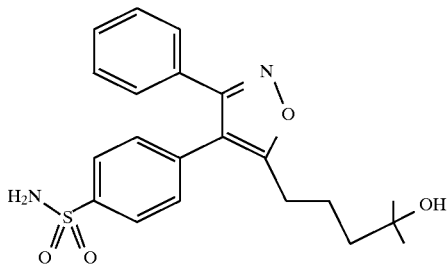

4-[5-(4-Hydroxy-4-methylpentyl)-3-phenylisoxazol-4-yl]benzenesulfonamide

Step 1: Preparation of methyl 4-[4-[4-(aminosulfonyl)phenyl]]-3-phenylisoxazol-5-yl]butanoate Powdered 4-[4-[4-(aminosulfonyl)phenyl]]-3-phenylisoxazol-5-yl]butanoic acid (Example 36) (0.613 g, 1.59 mmol) was added to a carefully prepared solution of thionyl chloride (1.0 mL, 1.63 g, 13.70 mmol) in methanol (20 mL). The resulting clear solution was heated to reflux for 5 hours, concentrated in vacuo yielding a brown solid. This solid was dissolved in ethyl acetate, decolorizing carbon was added, and the mixture was heated to reflux. The resulting suspension was passed through a plug of silica gel using ethyl acetate as eluant. The straw-colored filtrate was diluted with isooctane and concentrated in vacuo yielding methyl 4-[4-[4-(aminosulfonyl)phenyl]]-3-phenylisoxazol-5-yl] butanoate (0.640 g, 100%; as a tan crystalline solid of sufficient purity to be used without further purification: mp 158°–160° C.

Step 2: Preparation of 4-[5-(4-hydroxy-4-methylpentyl)-3-phenylisoxazol-4-yl]benzenesulfonamide To a stirred solution of the methyl 4-[4-[4-(aminosulfonyl)phenyl]]-3-phenylisoxazol-5-yl]butanoate (Step 1) (0.59 g, 1.47 mmol) in THF (15 mL) was added methyl magnesium bromide (2.0 mL, 3.0M in Et$_2$O , 5.89 mmol) via syringe. After 14 hours, the resulting tan suspension was quenched with 1N HCl solution and extracted with ethyl acetate. The ethyl acetate layer was washed with 1N HCl solution, NaHCO$_3$ solution (satd), and with brine, dried over MgSO$_4$, filtered and concentrated in vacuo yielding a tan solid. The solid was recrystallized from isooctane and dichloromethane yielding the desired product (0.262 g, 45%) as a tan powder: mp 184°–185° C. $^1$H NMR (CDCl$_3$/300 MHz) 7.89 (d, 2H, J=8.46 Hz), 7.38–7.22 (m, 7H), 5.89 (s, 2H), 2.77 (t, 2H, J=7.45 Hz), 1.88–1.72 (m, 2H), 1.51–1.43 (m, 2H), 1.17 (s, 6H). FABLRMS m/z 401 (M+H). FABHRMS m/z 401.1551 (M+H, C$_{21}$H$_{25}$N$_2$O$_4$S requires 401.1535). Anal. Calc'd for C$_{21}$H$_{24}$N$_2$O$_4$S.2.49 wt % H$_2$O: C, 61.41 H, 6.17; N, 6.82. Found: C, 61.41; H, 5.97; N, 6.67.

EXAMPLE 58

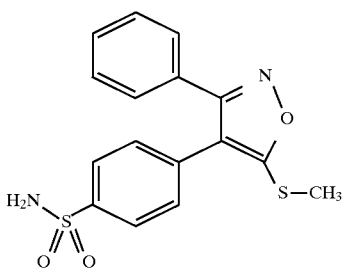

4-[5-Methylthio-3-phenylisoxazol-4-yl]benzenesulfonamide

Step 1. Preparation of 5-chloro-2,3-diphenylisoxazole.

To a stirred suspension of 3,4-diphenylisoxazolin-5-one (10.32 g, 32.62 mmol) in $POCl_3$ (100 mL) in a 250 mL flask was added DMF (1 mL). The reaction was stirred at room temperature for 0.25 hour, then at reflux for 3 hours. The resulting solution was concentrated in vacuo, toluene was added and reconcentrated in vacuo yielding a brown oil. Extraction of the oil with hot hexane yielded upon concentration in vacuo, 5-chloro-2,3-diphenylisoxazole as a pale yellow crystalline solid (1.94 g, 23%): mp 84°–87° C. $^1$H NMR ($CDCl_3$/300 MHz) 7.47–7.22 (m, 10H). FABLRMS m/z 256 (M+H). FABHRMS m/z 256.0548 (M+H, $C_{15}H_{11}ClNO$ requires 256.0529). Anal. Calc'd for $C_{15}H_{10}ClNO$.0.67 wt % $H_2O$: C, 69.98 H, 3.99; N, 5.44. Found: C, 69.99; H, 3.94; N, 5.30.

Step 2. Preparation of 5-methylthio-3,4-diphenylisoxazole.

To a stirred solution of 5-chloro-3,4-diphenylisoxazole (Step 1) (1.75 g, 6.84 mmol) in DMSO (30 mL) was added sodium thiomethoxide (0.58 g, 8.21 mmol). After stirring for 30 hours at room temperature, the reaction was diluted with water and extracted twice with $Et_2O$. The combined ethereal phases were washed with $NaHCO_3$ saturated solution, $KHSO_4$ solution (0.25N), and brine, dried over $MgSO_4$, filtered and concentrated in vacuo yielding 5-methylthio-3,4-diphenylisoxazole (1.53 g, 84%): mp 83°–86° C. $^1$H NMR ($CDCl_3$/300 MHz) 7.50–7.18 (m, 10H), 2.63 (s, 3H). FABLRMS m/z 268 (M+H). FABHRMS m/z 268.0781 (M+H $C_{16}H_{14}NOS$ requires 268.0796). Anal. Calc'd for $C_{16}H_{13}NOS$: C, 71.88; H, 4.90; N, 5.24. Found: C, 71.71; H, 4.95; N, 5.17.

Step 3. Preparation of 4-[5-methylthio-3-phenylisoxazol-4-yl]benzenesulfonamide.

To stirred chlorosulfonic acid (3.0 mL, 45.06 mmol) at room temperature was carefully added solid 5-methylthio-3,4-diphenylisoxazole (Step 2) (0.915 g, 3.42 mmol). After 3 hours at room temperature, the reaction was poured over crushed ice. The resulting suspension was layered with dichloromethane and excess concentrated ammonium hydroxide and was stirred vigorously for 3 hours. The layers were separated and the aqueous layer extracted with ethyl acetate. The organic phases were combined, washed with aqueous $KHSO_4$ solution (0.25N), aqueous $NaHCO_3$ solution, and brine, dried over $MgSO_4$, filtered and concentrated in vacuo yielding an oil. The oil was crystallized by dissolution in dichloromethane followed by the addition of isooctane until slight turbidity was seen. The resulting suspension was vacuum filtered yielding 4-[5-methylthio-3-phenylisoxazol-4-yl]benzenesulfonamide (0.355 g, 30%) as fine needles: mp 135°–137° C. $^1$H NMR ($CDCl_3$/300 MHz) 7.90 (d, 2H, J=8.5 Hz), 7.47–7.31 (m, 7 H), 4.81 (s, 2H), 2.69 (s, 3H). FABLRMS m/z 347 (M+H). FABHRMS m/z 347.0497(M+H, $C_{16}H_{15}N_2O_3S_2$ requires 347.0524). Anal. Calc'd for $C_{16}H_{14}N_2O_3S_2$.1.69 wt % $H_2O$: C, 54.54; H, 4.19; N, 7.95. Found: C, 54.53; H, 4.04; N, 7.87.

EXAMPLE 59

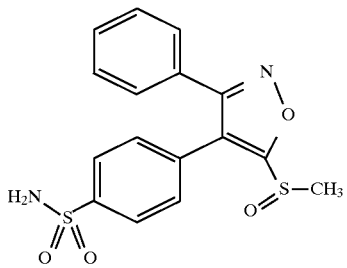

4-[5-Methylsulfinyl-3-phenylisoxazol-4-yl]benzenesulfonamide

To a chilled solution (−78° C.) of 4-[5-methylthio-3-phenylisoxazol-4-yl]benzenesulfonamide (Example 58) (0.256 g, 0.814 mmol) in dichloromethane (8 mL) was added MCPBA (0.234 g of 60% reagent, 0.814 mmol). After 1 hour, the reaction was warmed to 0° C. and held there for an additional hour. Dichloromethane (30 mL) and a solution of $NaHSO_3$ were added and mixed for 5 minutes. The resulting mixture was extracted with ethyl acetate (20 mL) and the layers separated. The organic phase was washed with $NaHSO_3$ solution and with $NaHCO_3$ solution, dried over $MgSO_4$, filtered and concentrated in vacuo yielding 4-[5-methylsulfinyl-3-phenylisoxazol-4-yl]benzenesulfonamide (0.107 g, 36%) as a pale yellow powder: mp 194°–204° C. $^1$H NMR ($CDCl_3$ with $DMSO_6$/300 MHz) 7.98 (d, 2H, 8.46 Hz), 7.53–7.37 (m, 7H), 6.39 (s, 2H), 3.18 (s, 3H). FABLRMS m/z 363 (M+H). FABHRMS m/z 363.0480 (M+H, $C_{16}H_{15}N_2O_4S_2$ requires 363.0473). Anal. Calc'd for $C_{16}H_{14}N_2O_4S_2$: C, 53.03; H, 3.89; N, 7.73. Found: C, 53.24; H, 3.96; N, 7.50.

EXAMPLE 60

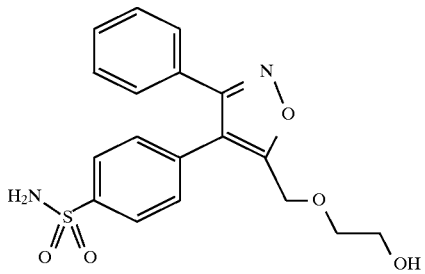

4-[5-(2-Hydroxyethyl)oxymethyl-3-phenylisoxazol-4-yl]benzenesulfonamide

To a chilled (0° C.), stirred solution of 5-[4-[4-[N-[2,5-dimethylpyrrol]-sulfonyl]phenyl]-3-phenylisoxazol-5-yl]]-methyloxyacetic acid (Example 35) (0.66 g, 1.85 mmol) in THF (15 mL) was added borane dimethylsulfide complex (0.28 mL of 10.0M solution, 2.78 mmol) causing the evolution of gas. The reaction was warmed to room temperature and stirred for 72 hours. The reaction was quenched with 1N HCl solution and the layers separated. The aqueous phase was extracted with ethyl acetate and the organic phases were combined, washed with aqueous $KHSO_4$ (0.25M), aqueous NaHCO₃ solution, brine, dried over MgSO₄, filtered and concentrated in vacuo yielding a clear tan oil. This oil was crystallized from dichloromethane, isooctane and acetone yielding 4-[5-(2-hydroxyethyl)oxymethyl-3-phenylisoxazol-4-yl]benzenesulfonamide (0.209 g, 56%) as a tan crystalline powder: mp 110°–121° C. ¹H NMR (CDCl₃/300 MHz) 7.93 (d, 2H, J=8.66 Hz), 7.47–7.29 (m, 7H), 4.87 (s, 2H), 4.64 (s, 2H), 3.83–3.72 (m, 2H), 3.72–3.65 (m, 2H), 1.84 (t, 1H, J=8.4 Hz). FABLRMS m/z 375 (M+H). FABHRMS m/z 375.1014 (M+H, $C_{18}H_{19}N_2O_5S_1$ requires 375.1015).

EXAMPLE 61

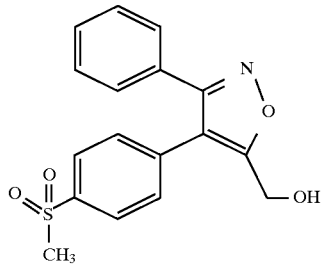

5-Hydroxymethyl-4-(4-methylsulfonyl)phenyl-3-phenyl-isoxazole

Step 1. Preparation of 5-hydroxymethyl-4-(4-thiomethyl)phenyl-5-phenyl isoxazole.

1-Phenyl-2-(4-methylthiophenyl)-ethan-1-one oxime (Example 5, step 2) (3.0 g, 12 mmol) was dissolved in tetrahydrofuran (150 mL). The mixture was cooled to –78° C. with stirring under nitrogen and treated dropwise with lithium diisopropylamine (2.0M, 13 mL, 26 mmol). The cooling bath was removed and when the internal temperature reached –10° C., methyl di-tert-butylmethylsilyl glycolate (2.96 g, 12 mmol) was added all at once. The solution was stirred for 15 minutes poured into a solution of hydrochloric acid (1.0N, 200 mL) and trifluoroacetic acid (10 mL) and stirred for 16 hours. The solution was diluted with ethyl acetate (150 mL) and washed with brine, saturated aqueous NaHCO₃, and water, dried over MgSO₄ and concentrated. The residue was purified by flash chromatography eluting with ethyl acetate:hexanes (1:1). The appropriate fractions were concentrated and dissolved in ethanol (100 mL). IR-120⁺ beads were added and the mixture was heated to reflux for 16 hours. The mixture was filtered and concentrated to a brown oil (0.8 g, 22%): Anal. Calc'd for $C_{17}H_{15}NO_2S+1.66\%$ H₂O: C, 67.53; H, 5.17; N, 4.54. Found: C, 67.53; H, 5.19; N, 4.63.

Step 2. Preparation of 5-hydroxymethyl-4-(4-methylsulfonyl)phenyl-5-phenyl-isoxazole.

5-Hydroxymethyl-4-(4-thiomethyl)phenyl-5-phenyl isoxazole (Step 1) (0.78 g, 2.62 mmol), ethanol (100 mL), water (40 mL), and Oxone® (3.55 g, 5.77 mmol) were stirred at room temperature overnight. The reaction mixture was extracted with ethyl acetate (2×100 mL). The combined extract was washed with water, sodium meta bisulfite, water, dried over MgSO₄ and concentrated. The crude product was purified by flash column chromatography eluting with ethyl acetate:hexanes (1:1). The appropriate fractions were concentrated and recrystallized from ethyl acetate/hexane/dichloromethane to yield 5-hydroxymethyl-4-(4-methylsulfonyl)phenyl-5-phenyl-isoxazole (39%, 0.34 g) as a white solid: mp 161.7°–162.7° C. ¹H NMR (DMSO-d₆/300 MHz) 7.93 (d, 2H, J=8.1 Hz), 7.5–7.3 (m, 7H), 577 (t, 1H, J=5.7 Hz), 4.55 (d, 2H, J=6.0 Hz), 3.25 (s, 3H).

Anal. Calc'd for $C_{18}H_{17}NO_4S$: C, 61.99; H, 4.59; N, 4.25. Found: C, 62.04; H, 4.61; N, 4.17.

The following compounds (Examples 62–65) were prepared according to procedures previously described:

EXAMPLE 62

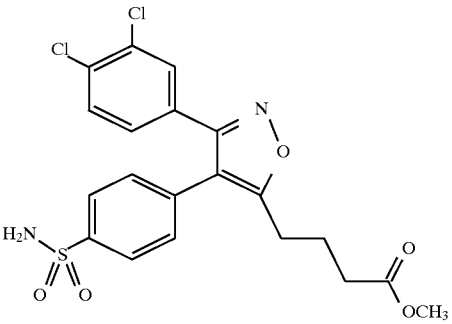

Methyl[4-(4-aminosulfonylphenyl)-3-(3,4-dichlorophenyl)isoxazol-5-yl]butanoate mp 124.7°–126.4° C. Anal. Calc'd for $C_{20}H_{18}Cl_2N_2O_5S*1.40$ H₂O. C, 48.58; H, 4.24; N, 5.66. Found: C, 48.53; H, 3.77; N, 5.50.

EXAMPLE 63

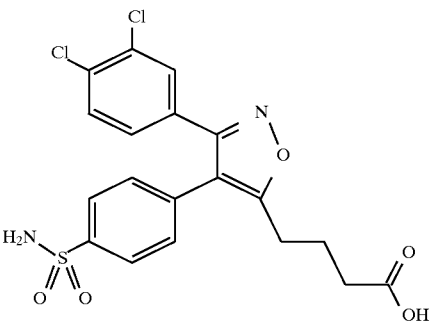

[4- (4-Aminosulfonylphenyl)-3- (3,4-dichlorophenyl)isoxazol-5-yl]butanoic acid mp 152.0°–155.0° C. Anal. Calc'd for $C_{19}H_{16}Cl_2N_2O_5S$: C, 50.12; H, 3.54; N, 6.15. Found: C, 49.89; H, 3.60; N, 5.99.

EXAMPLE 64

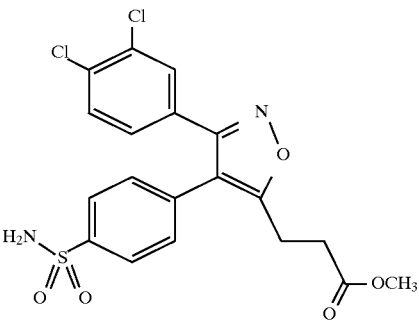

Methyl[4-(4-aminosulfonylphenyl)-3-(3,4-dichlorophenyl)isoxazol-5-yl]propanoate mp 159.2°–164.0° C. Anal. Calc'd for $C_{19}H_{16}Cl_2N_2O_5S$: C, 50.12; H, 3.54; N, 6.15. Found: C, 49.99; H, 3.56; N, 6.09.

EXAMPLE 65

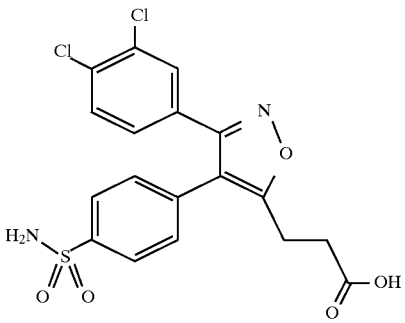

[4-(4-Aminosulfonylphenyl)-3-(3,4-dichlorophenyl)
isoxazol-5-yl]propanoic acid mp 50.4°–54.4° C. Anal. Calc'd for $C_{18}H_{14}Cl_2N_2O_5S$: C, 50.12; H, 354; N, 6.15. Found: C, 49.89; H, 3.60; N, 5.99.

EXAMPLE 66

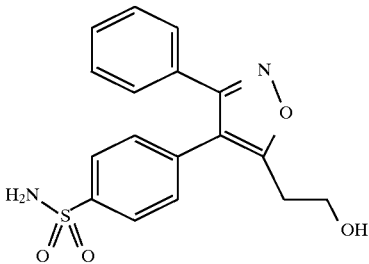

4-[5-(2-Hydroxyethyl)-3-phenylisoxazol-4-yl]
benzenesulfonamide

Step 1: Preparation of [4-[4-(aminosulfonyl)phenyl]-3-phenylisoxazol-5-yl]acetic acid

[4-[4-(Aminosulfonyl)phenyl]-3-phenylisoxazol-5-yl]acetic acid was prepared similar to the method of Example 55 but starting with 4-[5-methyl-3-phenylisoxazol-4-yl]benzenesulfonamide (Example 1): mp 201–202.

Step 2: Preparation of 4-[5-(2-hydroxyethyl)-3-phenylisoxazol-4-yl]benzenesulfonamide To a stirred solution of [4-[4-(aminosulfonyl)phenyl]-3-phenylisoxazol-5-yl]acetic acid (Step 1) (0.85 g, 2.37 mmol) in THF (25 mL) was added borane dimethylsulfide (0.47 mL of 10.0M solution, 4.74 mmol). After stirring at room temperature for 2 days, the reaction was quenched with aqueous $KHSO_4$ (0.25M) and extracted with ethyl acetate. The combined ethyl acetate phases were washed with saturated $NaHCO_3$ solution, brine, dried over $MgSO_4$, filtered and concentrated in vacuo yielding a pale yellow solid. The crude product was dissolved in hot dichloromethane and isooctane was added to induce crystallization. Vacuum filtration of the resulting suspension yielded 4-[5-(2-hydroxyethyl)-3-phenylisoxazol-4-yl]benzenesulfonamide (0.276 g, 34%) as a pale yellow solid: mp 186°–190° C. $^1$H NMR (DMSO d$_6$/300 MHz) 7.81 (d, 2H, J=8.0 Hz), 7.48–7.28 (m, 9H), 4.95 (t, 1H, J=5.0 Hz), 3.70 (q, 2H, J=5.6 Hz), 2.92 (t, 2H, J=6.2 Hz). FABLRMS m/z 345 (M+H). FABHRMS m/z 345.0923 (M+H, $C_{17}H_{17}N_2O_4S$ requires 345.0909). Anal. Calc'd for $C_{17}H_{17}N_2O_4S$·1.66 wt % $H_2O$: C. 58.30; H, 4.79; N, 8.00. Found: C, 58.37; H, 4.89; N, 7.60.

EXAMPLE 67

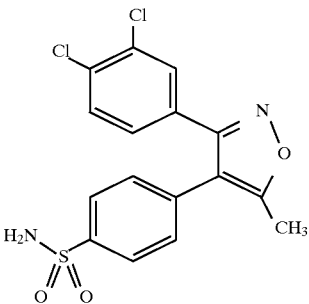

4-[5-Methyl-3-(3,4-dichlorophenyl)isoxazol-4-yl]
benzenesulfonamide

Step 1: Preparation of 1-(3,4-dichlorophenyl)-2-phenyl-ethan-1-one.

Cyanotrimethylsilane (72 mL, 571.4 mmol) was added to a stirred mixture of 3,4-dichlorobenzaldehyde (100.0 g, 571.4 mmol) zinc iodide (4.75 g) in anhydrous dichloromethane (600 mL) under nitrogen at 10° C. The reaction mixture was stirred for 90 minutes and was poured in to a separatory funnel containing aqueous sodium bicarbonate (200 mL). The organic layer was washed with brine (200 mL) and was dried and concentrated to afford the cyanohydrin. Lithium hexamethyldisilylamide (628 mL, 1N, 628 mmol) was added to tetrahydrofuran (400 mL) and the solution was cooled to −78° C. The cyanohydrin in tetrahydrofuran (200 mL) was added slowly to the above mixture over 15 minutes. After 15 minutes at this temperature, benzylbromide (68 mL) was added. The reaction mixture was stirred for 1 hour and was warmed to room temperature. The reaction mixture was poured in to trifluoroacetic acid (500 mL) containing 10% water. Stirred for 2 hours, and was neutralized with solid sodium carbonate. The reaction mixture was extracted with ethyl acetate (300 mL), washed with brine (200 mL) dried and was concentrated. The residue was stirred with aqueous sodium hydroxide (2N, 400 mL). The solid formed was filtered, washed with water, dried and was recrystallized from hexane to afford 108 g (72%) of the desired product in pure form: mp 84°–85° C. 1H NMR (CDCl$_3$) 8.09 (1H, s, J=2.01 Hz), 7.81 (dd, 1H, J=8.4, 2.0 Hz), 7.52 (d, 1H, J=8.4 Hz)), 7.38–7.24 (m, 5H), 4.25 (s, 2H). Anal. Calc'd for $C_{14}H_{10}OCl_2$: C, 63.42; H, 3.80. Found: C, 63.34; H, 3.82.

Step 2: Preparation of 1-(3,4-dichlorophenyl)-2-phenyl-ethan-1-one oxime.

A mixture of 1-(3,4-dichlorophenyl)-2-phenyl-ethan-1-one (Step 1) (12.5 g, 53.88 mmol), hydroxylamine hydrochloride (9.4 g, 135.4 mmol) and sodium acetate (268.5 mmol) in ethanol water (1:1, 250 mL) was heated at reflux for 4 hours, then was diluted with water (200 mL). The precipitate formed was filtered, dried and was recrystallized from hexane to afford 10 g (75%) of the desired product: mp 81°–82° C. $^1$H NMR (CDCl$_3$) 7.50–7.06 (m, 9H), 4.18 (s, 2H). Found: Anal. Calc'd for $C_{14}H_{11}NOCl_2$:

Step 3: Preparation of 4-[5-methyl-3-(3,4-dichlorophenyl) isoxazol-4-yl]benzenesulfonamide.

Butyllithium (18.1 mL, 1.6N, 44.99 mmol) was added to a solution of 1-(3,4-dichlorophenyl)-2-phenyl-ethan-1-one oxime (Step 2) (5.505 g, 20.45 mmol) in dry tetrahydrofuran (200 mL) at −78° C. The reaction mixture was stirred for 30 minutes at this temperature and was warmed up to 0° C., then was cooled again to −78° C. Ethyl acetate (1.801 g, 20.45 mmol) was added to the reaction mixture and was slowly warmed up to room temperature. The reaction mixture was quenched with saturated ammonium chloride solution, extracted with ethyl acetate, dried (MgSO₄) and was concentrated. The desired hydrate was obtained by purifying the residue. The hydrate was added chlorosulfonic acid (10 mL) at 0° C. and was stirred for 3 hours. Diluted with dichloromethane (25 mL), then poured carefully in to ice-water mixture. This was then extracted with dichloromethane (200 mL) and the organic layer was added to ammonium hydroxide (200 mL) and was stirred for 18 hours. The organic layer was separated, washed with brine (100 mL), dried (MgSO₄) and was concentrated. Chromatography (1:1 ethyl acetate, hexane of the residue afforded 0.360 g of the desired product as a crystalline material: mp 66°–71 ° C. ¹H NMR (CDCl₃) 7.97 (d, 2H, J=8.5 Hz), 7.60 (d, 1H, J=1.8 Hz), 7.39 (d, 1H, J=8.5 Hz), 7.31 (d, 2H, J=8.5 Hz), 7.11 (dd, 1H, J=8.4, 2.0 Hz). Anal. Calc'd for: C₁₆H₁₂N₂O₃SCl₂: C, 50.14; H, 3.16; N, 7.31. Found: C, 50.00; H, 3.20; N. 7.26.

EXAMPLE 68

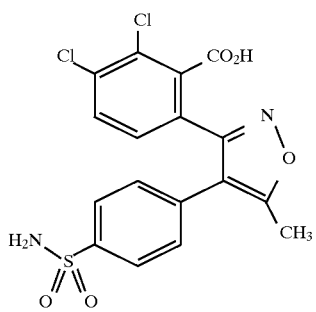

6-[4-[4-(Aminosulfonyl)phenyl]-5-methylisoxazol-]-yl]-2,3-dichlorobenzoic acid

A solution of 4-[5-methyl-3-(3,4-dichlorophenyl) isoxazol-4-yl]benzenesulfonamide (Example 67) (0.35 g, 0.9132 mmol) in tetrahydrofuran (20 mL) was cooled to −78° C. and butyllithium (1.25 mL, 1.6M, 2.01 mmol) was slowly added. Dry carbon dioxide was slowly bubbled into the reaction mixture at −78° C. The reaction mixture turned gray and the reaction mixture was warmed to room temperature. After quenching with saturated ammonium chloride, the reaction mixture was extracted with ethyl acetate (3×50 mL). The combined ethyl acetate extracts were washed with sodium bicarbonate. The combined aqueous extracts were cooled and was acidified with hydrochloric acid. The precipitate formed was extracted with ethyl acetate. The combined organic layers were dried and was concentrated to afford residue which was chromatographed (20% methanol in dichloromethane) to afford 0.15 g (39%) of the desired product: mp >250° C. ¹H NMR (CDCl₃) 7.73 (d, 2H, J=8.4 Hz), 7.31 (d, 2H, J=8.3 Hz), 7.15 (d, 2H, J=8.5 Hz), 6.80 (d, 2H, J=8.5 Hz), 2.39 (s, 3H). Anal. Calc'd for C₁₇H₁₂N₂O₅SCl₂: mol wt, 426.9922 (M+H). Found: mol wt, 426.9920 (M+H, HRFABMS).

EXAMPLE 69

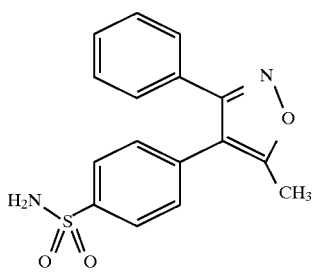

4-[5-Methyl-3-phenylisoxazol-4-yl] benzenesulfonamide

Step 1. Preparation of deoxybenzoin oxime.

A solution of deoxybenzoin (407.4 g, 2.076 mol) in 2 L of absolute ethanol and 600 mL of water was treated with hydroxylamine hydrochloride (288 g, 4.15 mol) and sodium acetate trihydrate (564 g, 4.15 mol). The solution was then warmed to reflux for 2 hours. The reaction mixture was then diluted with 1000 mL of 30% aqueous ethanol and allowed to cool to room temperature whereupon crystals of pure oxime formed which were isolated by filtration and air dried to afford 415.4 g, 95%, mp 94°–96° C. of pure deoxybenzoin oxime.

Step 2. Preparation of 5-hydroxy-5-methyl-3,4-diphenylisoxazoline.

A solution of deoxybenzoin oxime (300.0 g, 1.42 mol) was dissolved in 720 mL of anhydrous tetrahydrofuran and cooled to −20° C. in a dry ice/methanol bath. The solution was then treated with n-butyllithium (10M, 305 mL, 3.053 mol) over a period of 0.5 hour. The cooling bath was removed and the solution warmed to 0° C. and then ethyl acetate (298 mL, 269 g, 3.053 mol) was added over 0.5 hour. The solution was allowed to warm to room temperature and the reaction mixture diluted with 300 mL of ethyl acetate and then was treated with 1.2 L of water. The phases were separated and the aqueous phase was extracted with ethyl acetate and the combined ethyl acetate solution was dried over anhydrous MgSO₄, filtered and concentrated in vacuo to afford a white solid. The crude solid was then crystallized from 300 mL of a 1:1 mixture of ethyl acetate:hexanes to afford 132 g, 38%, mp 157.6°–162.6° C. of pure product.

Step 3. Preparation of 4-[(5-methyl-3-phenyl)-4-isoxazolyl] benzenesulfonamide.

Chlorosulfonic acid (355 mL, 587 g, 5.04 mol) was cooled in an ice/salt bath and then 5-hydroxy-5-methyl-3, 4-diphenylisoxazoline (142.2 g, 0.56 mol) was added at such a rate that the temperature was maintained between 10°–15° C. (ca. 35 minutes). The ice bath was removed and the solution stirred at room temperature for 16 hours. The mixture was then diluted with 250 mL of dichloromethane and the solution was slowly added to ice water with stirring. The mixture was diluted with an additional 1 L portion of dichloromethane and the phases were separated. The dichloromethane solution was dried over anhydrous MgSO₄, filtered and concentrated in vacuo to afford 144.1 g of white solid. This solid was dissolved in 600 mL of dichloromethane, cooled to 5° C. and was then treated with 600 mL of conc. NH₄OH and stirred at 15° C. for 15 minutes. The mixture was extracted with dichloromethane, dried over anhydrous MgSO₄, filtered and concentrated in vacuo to afford 131 g of a white solid. The crude solid was dissolved in 300 mL of boiling methyl ethyl ketone (2-butanone) and diluted with 300 mL of 10% aqueous isopropyl alcohol (prepared from 270 mL anhydrous isopropyl alcohol and 30 mL of water) and allowed to cool to room temperature whereupon crystals of pure 4-[(5-methyl-3-phenyl)-4-isoxazolyl]benzenesulfonamide formed which were isolated by filtration and dried in a vacuum drying oven at 10 mm Hg, 100° C. to afford 112.95 g, 65% of pure product, mp 172°–173° C.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs, in Non-steroidal Anti-Inflammatory Drugs*, (J. Lombardino, ed. 1985)). The % inhibition shows the % decrease from control paw volume determined in this procedure and the data for selected compounds in this invention are summarized in Table I.

Rat Carrageenan-induced Analgesia Test

The rat carrageenan analgesia test was performed with materials, reagents and procedures essentially as described by Hargreaves, et al., (*Pain*, 32, 77 (1988)). Male Sprague-Dawley rats were treated as previously described for the Carrageenan Foot Pad Edema Test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as scribed by Gierse et al, [*J. Biochem.*, 305, 479–84 (1995)]. A 2.0 kb fragment containing the coding region of either human or murine COX-1 or human or murine COX-2 was cloned into a BamHI site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$–$10^8$ pfu/mL) stocks of virus were prepared. For large scale production, SF9 insect cells were infected in 10 liter fermentors ($0.5 \times 10^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The nomogenate was centrifuged at 10,000×G for 30 minutes, and the resultant supernatant was stored at −80° C. before being assayed for COX activity.

b. Assay for COX-1 and COX-2 activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE I

| Example | RAT PAW EDEMA % Inhibition @ 10 mg/kg body weight | ANALGESIA % Inhibition @ 10 mg/kg body weight |
|---|---|---|
| 1 | 29 | 33 |
| 1(j) | 37 | 28 |
| 14 |  | 27* |
| 10 | 57 | 74 |
| 47 | 24 |  |
| 56 | 29* | 27* |
| 57 | 23* | 5* |
| 66 | 43* | 49* |

*@ 30 mg/kg

TABLE II

| Example | COX-2 IC50 μM | COX-1 IC50 μM |
|---|---|---|
| 1 | <0.1 | >100 |
| 1a | <0.1 | 17.4 |
| 1b | <0.1 | 13.2 |
| 1c | <0.1 | 6.2 |
| 1d | <0.1 | 25.8 |
| 1e | <0.1 | 37.7 |
| 1f | 0.2 | 54 |
| 1g | <0.1 | >100 |
| 1h | <0.1 | 4.7 |
| 1i | <0.1 | 8.6 |
| 1j | <0.1 | >100 |
| 1k | <0.1 | 50.7 |
| 1l | 1.5 | >100 |
| 1m | 51 | >100 |

TABLE II-continued

| Example | COX-2 IC50 μM | COX-1 IC50 μM |
|---|---|---|
| 1n | <0.1 | >100 |
| 1o | 0.1 | >100 |
| 2 | 0.9 | 17.4 |
| 3 | 2.6 | 0.6 |
| 4 | 3 | >100 |
| 4a | <0.1 | 90.5 |
| 4b | <0.1 | >100 |
| 4c | <0.1 | 66.5 |
| 4d | <0.1 | 44 |
| 4e | 2 | >100 |
| 4f | >100 | >100 |
| 5 | 4.0 | >100 |
| 6 | 35.7 | >100 |
| 7 | 86.7 | >100 |
| 8 | >100 | >100 |
| 9 | 1.4 | >100 |
| 10 | 0.2 | >100 |
| 11 | 35 | |
| 12 | 2.5 | >100 |
| 13 | <0.1 | 6.4 |
| 14 | <0.1 | 100 |
| 15 | 0.1 | 59 |
| 16 | 3.1 | >100 |
| 17 | 2.1 | >100 |
| 18 | 0.6 | >100 |
| 19 | 8.7 | >100 |
| 20 | 4.7 | >100 |
| 21 | 5.2 | >100 |
| 22 | 5.3 | >100 |
| 23 | 0.2 | 56 |
| 24 | 8.4 | >100 |
| 25 | 79 | >100 |
| 26 | 69.5 | >100 |
| 27 | 46 | >100 |
| 28 | 0.1 | >100 |
| 29 | 0.3 | >100 |
| 30 | <0.1 | 41 |
| 31 | 1.3 | >100 |
| 32 | 0.5 | 76 |
| 33 | <0.1 | 26 |
| 34 | 3.5 | >100 |
| 35 | 5.1 | >100 |
| 36 | 1.5 | >100 |
| 37 | 20 | >100 |
| 38 | <0.1 | >100 |
| 39 | 0.9 | >100 |
| 40 | 91 | 2.3 |
| 41 | 57.5 | 81 |
| 42 | 22.5 | >100 |
| 43 | 0.6 | >100 |
| 44 | 1.7 | >100 |
| 45 | <0.1 | 16 |
| 46 | 0.5 | 100 |
| 47 | <0.1 | >100 |
| 48 | 0.3 | 93 |
| 49 | 1.0 | >100 |
| 50 | <0.1 | >100 |
| 51 | 19 | >100 |
| 52 | 0.2 | 93 |
| 53 | 46 | >100 |
| 54 | 1.8 | >100 |
| 55 | <0.1 | >100 |
| 56 | 0.2 | >100 |
| 57 | 0.1 | >100 |
| 58 | <0.1 | 14 |
| 59 | <0.1 | >100 |
| 60 | 0.2 | >100 |
| 61 | 0.2 | >100 |
| 62 | 1.6 | >100 |
| 63 | 0.2 | >100 |
| 64 | 0.5 | >100 |
| 65 | 0.1 | 4.8 |
| 66 | <0.1 | >100 |
| 67 | 0.3 | 36 |
| 68 | 0.4 | >100 |

Biological paradigms for testing the cytokine-inhibiting activity of these compounds are found in WO95/13067, published 18 May 1995.

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

The phrase "co-therapy" (or "combination-therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

All mentioned references are incorporated by reference as if here written.

Although this invention has been described with respect to specific embodiments, the details of these embodiments are not to be construed as limitations.

What is claimed is:

1. A method of preparing compounds of Formula II

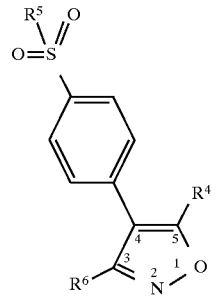

wherein $R^4$ is selected from hydroxyl, lower alkyl, carboxyl, halo, lower carboxyalkyl, lower alkoxycarbonylalkyl, lower aralkyl, methoxy, ethoxy, butoxy, lower alkylthio, lower alkoxyalkyl, lower aryloxyalkyl, lower arylthioalkyl, lower haloalkyl, lower hydroxylalkyl, lower aralkoxyalkyl, lower aryl (hydroxylalkyl), lower carboxyalkoxyalkyl, lower carboxyaryloxyalkyl, lower alkoxycarbonylaryloxyalkyl, lower cycloalkyl and lower cycloalkylalkyl; wherein $R^5$ is amino; and wherein $R^6$ is phenyl; wherein $R^6$ is optionally substituted at a substitutable position with one or more radicals independently selected from lower alkylsulfinyl, lower alkyl, cyano, carboxyl, lower alkoxycarbonyl, lower haloalkyl, hydroxyl, lower hydroxyalkyl, amino, lower haloalkoxy, lower alkylamino, phenylamino, lower aminoalkyl, nitro, halo, lower alkoxy, methylenedioxy, aminosulfonyl, and lower alkylthio; or a pharmaceutically-acceptable salt thereof, the method comprising the steps of forming a diphenylethanone derivative oxime by treatment of a diphenylethanone derivative with hydroxylamine, treating said oxime with base and an acylating agent to form a diphenylisoxazoline derivative, and forming the (isoxazol-4-yl)benzenesulfonamide by treatment of the isoxazoline with chlorosulfonic acid and ammonia.

2. The method of claim 1 wherein $R^4$ is selected from hydroxyl, methyl, ethyl, propyl, isopropyl, butyl, tert-butyl, isobutyl, pentyl, isopentyl, neopentyl, hexyl, chloro, carboxyl, carboxypropyl, carboxymethyl, carboxyethyl, carboxybutyl, carboxypentyl, methoxycarbonylmethyl, methoxycarbonylethyl, methoxycarbonylpropyl, methoxy, ethoxy, butoxy, methoxymethyl, phenoxymethyl, 4-fluorophenoxymethyl, pyridinylthiomethyl, methylthio, ethylthio, butylthio, ethylsulfinyl, butylsulfinyl, phenylsulfinyl, methoxyethyloxymethyl, benzyloxymethyl, phenylethoxymethyl, fluoromethyl, difluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxylmethyl, hydroxylpropyl, hydroxylethyl, 2-hydroxy-2-methylpentyl, cyclohexyl, cyclobutyl, cyclopentyl, cycloheptyl, cyclohexylmethyl, cyclohexylethyl, cyclobutylethyl, cyclopentylmethyl, cycloheptylpropyl, and lower aralkyl selected from benzyl and phenylethyl, wherein the phenyl ring is optionally substituted at a substitutable position with fluoro, chloro, bromo, iodo, methyl, and methoxy; and wherein $R^6$ is phenyl; wherein $R^6$ is optionally substituted at a substitutable position with one or more radicals independently selected from trifluoromethoxy, methylsulfinyl, ethylsulfinyl, methyl, ethyl, isopropyl, butyl, tert-butyl, isobutyl, pentyl, hexyl, cyano, carboxyl, methoxycarbonyl, fluoromethyl, difluoromethyl, trifluoromethyl, chloromethyl, dichloromethyl, fluoromethyl, difluoroethyl, difluoropropyl, dichloroethyl, dichloropropyl, hydroxyl, hydroxymethyl, fluoro, chloro, bromo, iodo, methoxy, ethoxy, propoxy, n-butoxy, pentoxy, hexyloxy, methylenedioxy, methylthio, ethylthio, butylthio, and hexylthio; or a pharmaceutically-acceptable salt thereof.

3. The method of claim 2 wherein the compound is selected from compounds, or a pharmaceutically acceptable salt thereof, of the group consisting of
4-[5-ethyl-3-phenylisoxazol-4-yl]benzenesulfonamide;
4-[3-phenyl-5-propylisoxazol-4-yl]benzenesulfonamide;
4-[5-isopropyl-3-phenylisoxazol-4-yl]benzenesulfonamide;
4-[5-butyl-3-phenylisoxazol-4-yl]benzenesulfonamide;
4-[5-isobutyl-3-phenylisoxazol-4-yl]benzenesulfonamide;
4-[5-cyclohexyl-3-phenylisoxazol-4-yl]benzenesulfonamide;
4-[5-neopentyl-3-phenylisoxazol-4-yl]benzenesulfonamide;
4-[5-cyclohexylmethyl-3-phenylisoxazol-4-yl]benzenesulfonamide;
4-[5-(4-chlorophenyl)methyl-3-phenylisoxazol-4-yl]benzenesulfonamide;
4-[5-difluoromethyl-3-phenylisoxazol-4-yl]benzenesulfonamide;
4-[5-chloromethyl-3-phenylisoxazol-4-yl]benzenesulfonamide;
4-[5-methoxymethyl-3-phenylisoxazol-4-yl]benzenesulfonamide;
4-[5-(3-hydroxypropyl)-3-phenylisoxazol-4-yl]benzenesulfonamide;
4-[3-(4-chlorophenyl)-5-methyl-isoxazol-4-yl]benzenesulfonamide;
4-[3-(4-fluorophenyl)-5-methyl-isoxazol-4-yl]benzenesulfonamide;
4-[3-(3-fluoro-4-methylphenyl)-5-methyl-isoxazol-4-yl]benzenesulfonamide;
4-[3-(3-chloro-4-methylphenyl)-5-methyl-isoxazol-4-yl]benzenesulfonamide;
4-[3-(3-fluorophenyl)-5-methyl-isoxazol-4-yl]benzenesulfonamide;
4-[5-hydroxymethyl-3-phenylisoxazol-4-yl]benzenesulfonamide;
[4-[4-(aminosulfonyl)phenyl]-3-phenylisoxazol-5-yl]carboxylic acid;
4-[5-hydroxy-3-phenyl-4-isoxazolyl]benzenesulfonamide;
4-[5-methyl-3-phenyl-isoxazol-4-yl]benzenesulfonamide;
4-[3-(3-fluoro-4-methoxyphenyl)-5-methyl-isoxazol-4-yl]benzenesulfonamide;
4-[3-phenyl-5-(3,3,3-trifluoro-2-oxopropyl)isoxazol-4-yl]benzenesulfonamide;
[4-[4-(aminosulfonyl)phenyl]-3-phenyl-isoxazol-5-yl]acetic acid;
[4-[4-(aminosulfonyl)phenyl]-3-phenyl-isoxazol-5-yl]propanoic acid;
ethyl [4-[4-(aminosulfonyl)phenyl]-3-phenyl-isoxazol-5-yl]propanoate; and
[4-[4-(aminosulfonyl)phenyl]-3-(3-fluoro-4-methoxyphenyl)isoxazol-5-yl]propanoic acid.

4. The method of claim 2 wherein the compound is 4-[5-methyl-3-phenylisoxazol-4-yl]benzenesulfonamide.

5. The method of claim 1 wherein the acylating agent is selected from anhydrides, acyl imidazoles and esters.

6. The method of claim 5 wherein the acylating agent is methyl acetate.

7. The method of claim 1 wherein the base is lithium diisopropylamide or butyllithium.

8. The method of claim 1 wherein the ammonia is concentrated ammonium hydroxide.

* * * * *